(12) United States Patent
Giese et al.

(10) Patent No.: US 9,790,505 B2
(45) Date of Patent: *Oct. 17, 2017

(54) INTERFERING RNA MOLECULES

(71) Applicant: Silence Therapeutics GMBH, Berlin (DE)

(72) Inventors: Klaus Giese, Berlin (DE); Jörg Kaufmann, Berlin (DE); Anke Klippel-Giese, Berlin (DE)

(73) Assignee: Silence Therapeutics GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,438

(22) Filed: May 12, 2017

(65) Prior Publication Data

US 2017/0247707 A1    Aug. 31, 2017

Related U.S. Application Data

(63) Continuation of application No. 14/977,710, filed on Dec. 22, 2015, now Pat. No. 9,695,423, which is a continuation of application No. 14/578,636, filed on Dec. 22, 2014, now Pat. No. 9,222,092, which is a continuation of application No. 13/692,178, filed on Dec. 3, 2012, now Pat. No. 8,933,215, which is a continuation of application No. 12/986,389, filed on Jan. 7, 2011, now Pat. No. 8,324,370, which is a continuation of application No. 12/200,296, filed on Aug. 28, 2008, now Pat. No. 7,893,245, which is a continuation of application No. 10/633,630, filed on Aug. 5, 2003, now Pat. No. 7,452,987.

(60) Provisional application No. 60/402,541, filed on Aug. 12, 2002.

(30) Foreign Application Priority Data

Aug. 5, 2002 (EP) .................................... 02017601
Apr. 10, 2003 (EP) .................................... 03008383

(51) Int. Cl.
C07H 21/04    (2006.01)
C12N 15/113   (2010.01)

(52) U.S. Cl.
CPC ........ *C12N 15/1137* (2013.01); *C12N 15/113* (2013.01); *C12N 2310/14* (2013.01); *C12N 2310/321* (2013.01); *C12N 2310/53* (2013.01)

(58) Field of Classification Search
None
See application file for complete search history.

(56) References Cited

U.S. PATENT DOCUMENTS

| | | | |
|---|---|---|---|
| 4,217,294 A | 8/1980 | Petty | |
| 5,466,786 A | 11/1995 | Buhr et al. | |
| 5,514,546 A | 5/1996 | Kool | |
| 5,589,389 A | 12/1996 | Pages et al. | |
| 5,670,633 A | 9/1997 | Cook et al. | |
| 5,792,847 A | 8/1998 | Buhr et al. | |
| 5,872,232 A | 2/1999 | Cook et al. | |
| 5,898,031 A | 4/1999 | Crooke | |
| 5,914,396 A | 6/1999 | Cook et al. | |
| 5,955,589 A | 9/1999 | Cook et al. | |
| 6,005,087 A | 12/1999 | Cook et al. | |
| 6,107,094 A | 8/2000 | Crooke | |
| 6,129,912 A | 10/2000 | Hortin et al. | |
| 6,133,246 A * | 10/2000 | McKay ................. | C07H 21/00 435/183 |
| 6,153,737 A | 11/2000 | Manoharan et al. | |
| 6,165,772 A | 12/2000 | Bertling | |
| 6,239,272 B1 | 5/2001 | Beigelman et al. | |
| 6,262,036 B1 * | 7/2001 | Arnold, Jr. ......... | C12N 15/1131 435/6.14 |
| 6,284,267 B1 | 9/2001 | Aneja | |
| 6,476,205 B1 | 11/2002 | Buhr et al. | |
| 6,506,559 B1 | 1/2003 | Fire et al. | |
| 6,531,584 B1 | 3/2003 | Cook et al. | |
| 6,617,438 B1 | 9/2003 | Beiqelman et al. | |
| 6,812,204 B1 | 11/2004 | McHale et al. | |
| 7,056,704 B2 | 6/2006 | Tuschl et al. | |
| 7,074,863 B2 | 7/2006 | Ekholm et al. | |
| 7,078,196 B2 | 7/2006 | Tuschl et al. | |
| 7,138,517 B2 | 11/2006 | Cook et al. | |
| 7,148,342 B2 | 12/2006 | Tolentino et al. | |

(Continued)

FOREIGN PATENT DOCUMENTS

CA    2476112 A1    8/2003
DE    19618797 A1   11/1997

(Continued)

OTHER PUBLICATIONS

U.S. Appl. No. 60/352,873, dated Feb. 1, 2002, Damha et al.
U.S. Appl. No. 60/358,580, dated Feb. 20, 2002, Beiqelman et al.
U.S. Appl. No. 60/363,124, dated Mar. 11, 2002, Beigelman et al.
U.S. Appl. No. 60/386,782, dated Jun. 6, 2002, Beigelman et al.
Amarzguioui, M. et al. "Tolerance for mutations and chemical modifications in a siRNA", Nucleic Acids Research, 2003, pp. 589-595, vol. 31, No. 2.
Andrew Fire. et al., Potent and specific genetic interference by double-stranded RNA in Caenorhabditis elegans, Nature Macmilian Publishers Ltd. 1993, vol. 391/191, pp. 806-811.
Andrew J. Hamilton and David C. Balcombe, Species of Small Antisense RNA in Posttranscriptional Gene Silencing in Plants, Sci Ence, vol. 286. Dec. 1999, pp. 950-951.

(Continued)

*Primary Examiner* — Kimberly Chong
(74) *Attorney, Agent, or Firm* — Morrison & Foerster LLP

(57) ABSTRACT

The present invention is related to a ribonucleic acid comprising a double stranded structure whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides whereby said second stretch is at least partially identical to a target nucleic acid, and whereby the double stranded structure is blunt ended.

23 Claims, 29 Drawing Sheets

(56) References Cited

U.S. PATENT DOCUMENTS

| | | |
|---|---|---|
| 7,196,184 B2 | 3/2007 | Heidenreich et al. |
| 7,348,314 B2 | 3/2008 | John et al. |
| 2003/0027783 A1 | 2/2003 | Zernicka-Goetz et al. |
| 2003/0108923 A1 | 6/2003 | Tuschl et al. |
| 2003/0135033 A1 | 7/2003 | Klippel-Giese et al. |
| 2003/0190635 A1 | 10/2003 | McSwiggen |
| 2004/0053875 A1 | 3/2004 | Kreutzer et al. |
| 2004/0072779 A1 | 4/2004 | Kreutzer et al. |
| 2004/0102408 A1 | 5/2004 | Kreutzer et al. |
| 2004/0106569 A1 | 6/2004 | Klippel-Giese et al. |
| 2004/0175703 A1 | 9/2004 | Kreutzer et al. |
| 2004/0180351 A1 | 9/2004 | Giese et al. |
| 2004/0229266 A1 | 11/2004 | Tuschl et al. |
| 2005/0043263 A1 | 2/2005 | Giese et al. |
| 2005/0100907 A1 | 5/2005 | Kreutzer et al. |
| 2005/0142535 A1* | 6/2005 | Damha .......... C07H 21/00 435/5 |
| 2006/0094678 A1 | 5/2006 | Vornlocher et al. |
| 2006/0142226 A1 | 6/2006 | Polisky et al. |
| 2006/0217329 A1 | 9/2006 | Feinstein |
| 2006/0240022 A1 | 10/2006 | Klippel-Giese et al. |
| 2007/0027097 A1 | 2/2007 | Lewis |
| 2007/0093445 A1 | 4/2007 | Tuschl et al. |
| 2007/0135372 A1 | 6/2007 | Maclachlan et al. |
| 2007/0265220 A1 | 11/2007 | Rossi et al. |
| 2014/0220676 A1 | 8/2014 | Kreutzer et al. |

FOREIGN PATENT DOCUMENTS

| | | |
|---|---|---|
| DE | 19903713 | 1/1999 |
| DE | 19956568 A1 | 8/2000 |
| EP | 0586520 B1 | 4/2000 |
| EP | 0618925 B1 | 8/2001 |
| EP | 1214945 A2 | 6/2002 |
| EP | 1144623 B1 | 8/2002 |
| EP | 020185724 | 8/2002 |
| EP | 1230375 B1 | 7/2005 |
| EP | 1550719 A1 | 7/2005 |
| EP | 1527176 B1 | 1/2007 |
| EP | 1798285 A1 | 6/2007 |
| EP | 1407044 B1 | 9/2007 |
| GB | 992744 A | 5/1965 |
| GB | 2417727 B | 1/2008 |
| WO | WO-92/07065 A1 | 4/1992 |
| WO | WO-92/19732 A1 | 11/1992 |
| WO | WO-92/20823 A1 | 11/1992 |
| WO | WO-93/13121 A1 | 7/1993 |
| WO | WO-94/01550 A1 | 1/1994 |
| WO | WO-95/13834 A1 | 5/1995 |
| WO | WO-96/18376 A1 | 6/1996 |
| WO | WO-96/18736 A2 | 6/1996 |
| WO | WO-97/41141 A1 | 11/1997 |
| WO | WO-97/46570 A1 | 12/1997 |
| WO | WO-98/05770 A2 | 2/1998 |
| WO | WO-98/53083 A1 | 11/1998 |
| WO | WO-99/15682 A2 | 4/1999 |
| WO | WO-99/32619 A1 | 7/1999 |
| WO | WO-99/49029 A1 | 9/1999 |
| WO | WO-99/53050 A1 | 10/1999 |
| WO | WO-99/55857 A2 | 11/1999 |
| WO | WO-99/61631 A1 | 12/1999 |
| WO | WO-00/01846 A2 | 1/2000 |
| WO | WO-00/44495 A1 | 8/2000 |
| WO | WO-00/44895 A1 | 8/2000 |
| WO | WO-00/44914 A1 | 8/2000 |
| WO | WO-00/63364 A2 | 10/2000 |
| WO | WO-01/36646 A1 | 5/2001 |
| WO | WO-01/75164 A2 | 10/2001 |
| WO | WO-02/16620 A2 | 2/2002 |
| WO | WO-02/44321 A2 | 6/2002 |
| WO | WO-02/055693 A2 | 7/2002 |
| WO | WO-02/097114 A2 | 12/2002 |
| WO | WO-03/064441 A2 | 8/2003 |
| WO | WO-03/070895 A2 | 8/2003 |
| WO | WO-03/070912 A2 | 8/2003 |
| WO | WO-03/070918 A2 | 8/2003 |
| WO | WO-2004/015107 A3 | 2/2004 |
| WO | WO-2004/019973 A1 | 3/2004 |
| WO | WO-2004/035615 A2 | 4/2004 |
| WO | WO-2005/000320 A2 | 1/2005 |
| WO | WO-2005/105152 A2 | 11/2005 |
| WO | WO-2006/023544 A2 | 3/2006 |
| WO | WO-2006/069782 A2 | 7/2006 |
| WO | WO-2007/048244 A2 | 5/2007 |
| WO | WO-2007/084684 A2 | 7/2007 |

OTHER PUBLICATIONS

Antonio Regalado, Turning Off Genes Sheds New Light On How They Work, The Wall Street Journal, Aug. 2002.

Antti Nykanen et al., "ATP Requirements and Small Interfering RNA Structure in the RNA Interference Pathway", Cell, Nov. 2, 2001, pp. 309-321, vol. 107.

Applicant's Response to the Written Opinion in the Examination proceedings Mar. 28, 2001.

Barawkar, D.A. et al., Synthesis, Biophysical Properties, and Nuclease Resistance Properties of Mixed Backbone Oligodeoxynucleotides Containing Cationic Internucleoside Guanidinium Linkages: Deoxynucleic Guanidine DNA Chimeras, Proc. R165 Natl. Acad. Sci. USA, vol. 95, pp. 11047-11052, Sep. 1998 Chemistry, Biochemistry.

Barber, GN et al., Mol. and Cell. Biol. (1995), vol. 15, No. 6, p. 3138-3146.

Behlke, M.A. (Dec. 2008). "Chemical modification of siRNAs for in vivo use," *Oligonucleotides* 18(4):305-320.

Bertrand, J. et al. "Comparison of antisense oligonucleotides and siRNAs in cell culture and in vivo", Biochemical and Biophysical Research Communications, 2002, pp. 1000-1004, vol. 296.

Bevilacqua and Cech; "Minor-Groove Recognition of Double-Stranded RNA by the Double-Stranded RNA-Binding;" Biochemistry 1996, 35, pp. 9983-9994.

Bhan et al., Nucleic Acid Research, vol. 25, 1997, p. 3310.

Billy, E. et al. "Specific interference with gene expression induced by long, doublestranded RNA in mouse embryonal teratocarcinoma cell lines", PNAS, Dec. 4, 2001, pp. 14428-14433, vol. 98, No. 25.

Borecky L, et al., Therapeutic Use of Double-Stranded RNAs in man, Tex Rep Bio Med 1981-1982, vol. 41, pp. 575-581.

Boutla, A et al. "Short 5'-phosphorylated double-stranded RNAs induce RNA interference in Drosophila", Current Biology, Nov. 13, 2001, pp. 1776-1780, vol. 11.

Braasch, DA et al. "RNA Interference in Mammalian Cells by Chemically-Modified RNA", Biochemistry, 2003, pp. 7967-7975, vol. 42.

Brennicke et al., FEMS Microbiol. Rev., vol. 23, p. 297-316 1999.

Brief Communication (Interlocutory decision) in EPO Patent No. 1 527 176 (EP 03 784183.0) dated Mar. 15, 2010, pp. 1-75.

Brown, K. M. et al. "Target accessibility dictates the potency of human RISC", Nature Structural & Molecular Biology, May 2005, pp. 469-470, vol. 12, No. 5.

Byrom, MW., et al., TechNotes 10(1), Ambion, http://www.ambion.com, Mar. 2003.

Caplen et al; "Specific inhibition of gene expression by small double-stranded RNAs in invertebrate and vertebrate systems" Proc Natl Acad Sci U SA. Aug. 14, 2001;98(17):9742-7.

Chien, et al., Cancer Gene Therapy, 1-8, 2004.

Chiu et al. "siRNA function in RNAi: a chemical modification analysis." RNA. 2003 ep;9(9): 1034-48.

Chiu, Y. et al. "RNAi in Human Cells: Basic Structural and Functional Features of Small Interfering RNA", Molecular Cell, Sep. 2002, pp. 549-561, vol. 10.

Chiu, Y. et al. (Sep. 2003). "siRNA function in RNAi: A chemical modification analysis" *RNA* 9(9):1034-1048.

Choung et al "Chemical modification of siRNAs to improve serum stability without loss of efficacy." Biochem Biophys Res Commun., Apr. 14, 2006;342(3):919-27.

(56) References Cited

OTHER PUBLICATIONS

Christian Cazenave et al., "Rate of degradation of [a]—and LB —oligodeoxynucleotides in Xenopus oocytes. implications for anti-messenger strategies", Nucleic Acids Research, 1987, DD. 10507-10521, vol. 15, No. 24.

Clayton, J. "The Silent Treatment", Nature, Sep. 30, 2004, pp. 599-605, vol. 431.

Clemens, J.C. et al. "Use of double-stranded RNA interference in Drosophilia cell lines to dissect signal transduction pathways", PNAS, Jun. 6, 2000, pp. 6499-6503, vol. 97, No. 12.

Clemens, M. J. "PKR—A Protein Kinase Regulated by Double-stranded RNA", Int. J Biochem. Cell Biol., 1997, pp. 945-949, vol. 29, No. 7.

Collingwood MA (Jun. 2008). "Chemical modification patterns compatible with high potency dicer-substrate small interfering RNAs," Olingonculeotides, 18(2):187-200.

Comparative Figure: D10 (Pachuk) v. Opposed Patent, Feb. 2, 2007.

Comparative Figure: D60 (Agrawal) v. Opposed Patent, Feb. 2, 2007.

Conklin, D., et al., "Association of nucleotide patterns with gene function classes: application to human 3' untranslated sequences," Bioinformatics, 2002, vol. 18, No. 1, pp. 182-189.

Conrad et al. "Ribonuclease III: new sense from nuisance." Int J Biochem Cell Biol. Feb. 2002; 34(2): 116-29.

Crooke, R. M. et al. "Metabolism of Antisense Oligonucleotides in Rat Liver Homogenates", The Journal of Pharmacology and Experimental Therapeutics, 2000, pp. 140-149, vol. 292.

Czauderna, F. et al. "Functional Studies of the PI(3)-kinase signaling pathway employing synthetic and expressed siRNA", Nucleic Acids Research, 2003, pp. 670-682, vol. 31, No. 2.

David C. Baulcombe, "Fast forward genetics based on virus-induced gene silencing", Current Opinion in Plant Biology, 1999, pp. 109-113, vol. 2.

Declaration of Professor Dr. Michael Gait, filed Aug. 5, 2003, 76pages.

Delivery Note, 2 pages, Dec. 20, 2001.

Doench, J. G. et al., siRNAs Can Function as miRNAs, Genes & Development, vol. 17, pp. 438-442, 2003.

Dorsett, Y. et al. "siRNAs: Applications in Functional Genomics and Potential as Therapeutics", Drug Discovery, Apr. 2004, pp. 318-329, vol. 3.

Elayadi, A N. et al. "Application of PNA and LNA oligomers to chemotherapy" Current Opinion in Investigational Drugs, 2001, pp. 558-561, vol. 2, No. 4.

Elbashir SM, et al., Duplexes of 21-Nucleotide RNAs Mediate RNA Interference in Cultured Mammalian Cells, Nature, vol. 411, pp. 494-498, May 2001.

Elbashir, et al., RNA Interference Is Mediated by 21- and 22-Nucleotide RNAs, Genes & Development vol. 15, pp. 188-200, Jan. 2001.

Emily Bernstein et al., "Role for a bidentate ribonuclease in the initiation step of RNA interference", Nature, Jan. 18, 2001, p. 363-366, vol. 409.

EPO Register extract for WO 03/070895, Dec. 9, 2007, pp. 1-2.

EPO Register extract for WO 03/070918, Nov. 9, 2007, pp. 1-4.

Eric Billy et al., "Specific Interference with Gene Expression Induced by Long, Double-Stranded RNA in Mouse Embryonal Teratocarcinoma Cell Lines", Proceedings of the National Academy of Sciences of the United States of America, Dec. 4, 2001, pp. 14428-14433, vol. 98, No. 25.

Eric G. Moss, et al, The Cold Shock Domain Protein Lin-28 Controls Developmental Timing in C. Elegans and is Regulated by the Lin-4 RNA, Cell, vol. 86, pp. 637-646, Mar. 7, 1997.

Eric Wickstrom, "Oligodeoxynucleotide stability in subcellular extracts and culture media", Journal of Biochemical and Biophysical Methods, 1986, pp. 97-102, vol. 13.

Eugen Uhlmann, et al.. Antisense Oligonucleotides: A New Therapeutic Principle, vol. 90, No. 4, pp. 553-584, Jun. 1990.

Extract from Hackh's Chemical Dictionary, Fourth Edition, 1969, McGraw-Hill, p. 492.

Extract from McGraw-Hill Dictionary of Scientific and Technical Terms, Fifth Edition, 2003, p. 1457.

Extract from Shorter Oxford English Dictionary, 51th ed., 2003, relating to "pattern", pp. 1-3.

Fire, "RNA-triggered gene Silencing;" TIG, pp. 358-363, vol. 15, No. 9, Sep. 1999.

Florence Wianny, et al. Specific Interference with Gene Function by Double-Stranded RNA in Early Mouse Development, Nature Cell Biology, vol. 2, Feb. 2000, pp. 70-75.

Frank Czauderna, et al., Structural Variations and Stabilising Modifications of Synthetic siRNAs in Mammalian Cells, Nucleic Acids Research, 2003, vol. 31, No. 11, pp. 2705-2716.

Friedrich Lottspeich I Haralabos Zorbas: Bioanalytics, 1998, pp. 785, 794.

Gary, D. J. et al. "Polymer-based siRNA delivery: Perspectives on the fundamental and phenomenological distinctions from polymer-based DNA delivery", Journal of Controlled Release, 2007, pp. 64-73, vol. 121.

Glenn D. Hoke et al., Effects of Phosphorothioate Capping on Antisense Oligonucleotide Stability, Hybridization and Antiviral Efficacy Versus Herpes Simplex Virus Infection, Nucleic Acids Research,1991, vol. 19, No. 20, pp. 5743-5748.

Good, P. D. et al. "Expression of small, therapeutic RNAs in human cell nuclei" Gene Therapy, 1997, pp. 45-54, vol. 4.

Grasby, J. A. et al., Purine Functional Groups in Essential Residues of the Hairpin Ribozyme Required for Catalytic Cleavage of RNA, Biochemistry 1995, vol. 34, pp. 4068-4076.

Griffey, R. H. et al., 2'-0-Aminoprophyl Ribonucleotides; A Zwitterionic Modification that Enhances the Exonuclease Resistance and Biological Activity of R156 Antisense Oligonucleotides, J. Med. Chem, 1996, vol. 39, pp. 5100-5109.

Grounds of Appeal filed on behalf of Alcon Laboratories, Inc. in EPO Patent No. 1 527 176 (EP Patent Application No. 03. 784183.0) dated Jul. 26, 2010, pp. 1-63.

Grunweller et al. "Comparison of different antisense strategies in mammalian cells using locked nucleic acids, 2'-0-methyl RNA, phosphorothioates and small interfering RNA" Nucleic Acids Res. Jun. 15, 2003;31(12):3185-93.

Guan, K. L. et al. "Eukaryotic Proteins Expressed in *Escherichia coli*: An Improved Thrombin Cleavage and Purification Procedure of Fusion Proteins with Glutathione S-Transferase" Analytical Biochemistry, 1991, pp. 262-267, vol. 129.

Hall, I. M. et al. "Establishment and Maintenance of a Heterochromatin Domain", Science, Sep. 27, 2002, pp. 2232-2237, vol. 297.

Hammond, S. M. et al. "Argonaute2, a Link Between Genetic and Biochemical Analyses ofRNAi", Science, Aug. 10, 2001, pp. 1146-1150, vol. 293.

Hammond, S.M. et al. "An RNA-directed nuclease mediates post-transcriptional gene silencing in Drosophila cells", Nature, Mar. 16, 2000, pp. 293-296, vol. 404.

Hannon, G. J. "RNA interference", Nature, Jul. 11, 2002, pp. 244-251, vol. 418.

Harborth, et al.,"Identification of essential genes in cultured mammalian cells using small interfering RNAs;" J Cell Science; 114: pp. 4557-4565; (2001).

Harborth, J. et al. "Sequence, Chemical, and Structural Variation of Small Interfering RNAs and Short Hairpin RNAs and the Effect on Mammalian Gene Silencing", Antisense and Nucleic Acid Drug Development, 2003, pp. 83-105, vol. 13.

Hoerter, J. A. et al. "Chemical Modification Resolves the Asymmetry of siRNA Strand Degradation in Human Blood Serum", RNA, 2007, pp. 1-7, vol. 13.

Holen, T. et al. "Positional Effects of Short Interfering RNAs targeting the human coagulation trigger Tissue Factor", Nucleic Acids Research, 2006, pp. 1757-1766, vol. 30, No. 8.

Hornung et al., Nature Medicine, vol. 11, No. 3, pp. 263-270, Mar. 2005.

Hu, X. et al. "Relative gene-silencing efficiencies of small interfering RNAs targeting sense and antisense transcripts from the same genetic locus", Nucleic Acids Research, 2004, pp. 4609-4617, vol. 32, No. 15.

(56) References Cited

OTHER PUBLICATIONS

Hu-Lieskovan, et al, Cancer Res., vol. 65, No. 19, pp. 8984-8992, Oct. 1, 2005.
Hunter, et al., JBC, vol. 250, No. 2, pp. 409-417, Jan. 25, 1975.
Ilho HA et al., A Bulged Lin-4/1 in-14 RNA Duplex is Sufficient for Caenorhabditis Elegans Lin-14 Temporal Gradient Formation, Genes & Development, 1996, vol. 10, pp. 3041-3050.
Ikuma Maeda et al., "Large-scale analysis of gene function in Caenorhabditis elegans by high-throuqhput RNAi", Current Biology, 2001, pp. 171-176, vol. 11.
Inoue et al.,"Synthesis and hybridization studies on two complementary nona(2'0-methyl)ribonucleotides"; Nucleic Acids Res., 1987, pp. 6131-6148, vol. 15.
Inoue, A. et al. "Molecular Design and Delivery of siRNA", Journal of Drug Targeting, 2006, pp. 448-455, vol. 14, No. 7.
International Preliminary Examination Report, (English Translation) DE 0000244 (IPER), dated Jul. 7, 2003.
Jackson, A. L. et al. "Position-specific chemical modification of siRNAs reduces "off-target" transcript silencing", RNA, 2006, pp. 1197-1205, vol. 12.
Jason R. Kennerdell et al., "Heritable gene silencing in Drosophila using doublestranded RNA", Nature Biotechnology, Jul. 2000, pp. 896-898, vol. 17.
Jason R. Kennerdell et al., "Use of dsRNA-Mediated Genetic Interference to Demonstrate that frizzled and frizzled 2 Act in the Wingless Pathway", Cell, Dec. 23, 1998, pp. 1017-1026, vol. 95.
Jason R. Kennerdell, et al. Use of dsRNA-Mediated Genetic Interference to Demonstrate that Frizzled and Frizzled 2 Act in the Wingless Pathway, Cell, vol. 95, pp. 1017-1026, Dec. 23, 1998.
Jennifer Couzin, Breakthrough, Small RNAs Make Big Splash, Science, vol. 298, pp. 2296-2297, Dec. 2002.
John Wiley &Sons, Current Protocols in Molecular Biology, vol. 1, 1999.
Judge et al, Nature Biotechnology, vol. 23, No. 4, pp. 457-462, Apr. 2005.
Kalota et al. "2'-deoxy-2'-fluoro-beta-D-arabinonucleic acid (2'F-ANA) modified oligonucleotides (ON) effect highly efficient, and persistent, gene silencing." Nucleic Acids Res. Jan. 18, 2006; 34(2):451-61. Print 2006.
Karberg, Mach doch mal das Gen aus, Die Zeit, No. 41, May 10, 2006.
Kitabwalla, M. et al. "RNA-Interference-A New Weapon Against HIV and Beyond", N. Engl. J. Med. vol. 347, No. 17, pp. 1364-1367, Oct. 24, 2002.
Klippel, A. et al. "The Interaction of Small Domains between the Subunits of Phosphatidylinositol 3-Kinase Determines Enzyme Activity", Molecular and Cellular Biologv, Apr. 1994, pp. 2675-2685, vol. 14, No. 4.
Koller, E. et al. "Competition for RISC binding predicts in vitro potency of siRNA", Nucleic Acids Research, 2006, pp. 4467-4476, vol. 34, No. 16.
Kraynack et al.,"Small interfering RNAs containing full 2'-0-methylribonucleotidemodified sense strands display Argonaute2/elF2C2-dependent activity." RNA. Jan. 2006;12(1 ):163-76.
Kurreck, "Improvement through novel chemical modifications;" Eur. J. Biochem, 270, 1628-1644 (2003).
Layzer, J. M. et al. "In vivo activity of nuclease-resistant siRNAs", RNA, 2004, pp. 766-771,vol. 10.
Leenders, F. et al. "PKN3 is required for malignant prostate cell growth downstream of activated PI 3-kinase", The EMBO Journal, 2004, pp. 3303-3313, vol. 23, No. 16.
Letter accompanying subsequently filed items filed in EPO Patent No. 1 527 176 (EP 03784183.0) dated Jul. 26, 2010, pp. 1-69.
Li et al., Dev. Biology, vol. 210, 1999, p. 238, Abstr. 346.
Lima, W. F. et al. "Structural Requirements at the Catalytic Site of the Heteroduplex Substrate for Human RNase H1 Catalysis", The Journal of Biological Chemistry, Aug. 27, 2004, pp. 36317-36326, vol. 279, No. 35.

Lipinski et al., Experimental and Computational Approaches to Estimate Solubility and Permeability in Drug Discovery and Development Settings, Adv. Drug Delivery Reviews vol. 23, pp. 3-25, 1997.
Lubini, P. et al. "Stabilizing effects of the RNA 2'-substituent: crystal structure of an oligodeoxynucleotide duplex containing 2'-0-methylated adenosines", Chemistry & Biology, Sep. 1994, pp. 39-45, vol. 1.
M. Monoharan;"2'-Carbohydrate modifications in antisense oligonucleotide therapy . . . ;" Biochimica et Biophysica Acta; 1999, pp. 117-130.
Madhur Kumar, et al., Antisense RNA: Function and Fate of Duplex RNA in Cells of Higher Eukaryotes, Microbiology and Molecular Biology Reviews, Dec. 1998, pp. 1415-1434.
Mahato et al. "Modulation of Gene Expression by Antisense and antigene oligodeoxynucleotides and small interfering RNA", Expert Opin. De/iv., 2005, pp. 3-28, vol. 2, No. 1.
Majumdar, A. et al., Targeted Gene Knockout Medicated by Triple Helix Forming Oligonucleotides, Nature Genetics, vol. 20, Oct. 1998, pp. 212-214.
Manche et al., Mol. Cell, Biol., vol. 12, No. 11, p. 5238-5248, Nov. 1992.
Manoharan, M. "RNA interference and chemically modified small interfering RNAs", Current Opinion in Chemical Biology, 2004, pp. 570-579, vol. 8.
Manoharan, M. (Dec. 10, 1999). "2'-carbohydrate modifications in antisense oligonucleotide therapy: importance of conformation, configuration and conjugation," *Biochim Biophys Acta.* 1489(1):117-30.
Maria Sternberger et al., "GeneBlocs Are Powerful Tools to Study and Delineate A15 Signal Transduction Processes That Regulate Cell Growth and Transformation", Antisense & Nucleic Acid Druq Development, 2002, pp. 131-143, vol. 12.
Mark D. Pegram, et al., Phase II Study of Receptor-Enhanced Chemosensitivity Using Recombinant Humanized Anti-p185her2/NEU Monoclonal Antibody Plus Cisplatin in Patients With HER2/neu-Overexpressing Metastatic Breast Cancer Refractory to Chemotherapy Treatment. Journal of Clinical Oncology, vol. 16, No. 8 Aug. 1998: pp. 2659-2671.
Martinez et al., Cell, vol. 110, pp. 563-574. Jun. 9, 2002.
Martinez, J. et al. "RISC is a 5' phosphomonoester-producing RNA endonuclease", Genes & Development, 2004, pp. 975-980, vol. 18.
Martinez, J. et al. "Single-Stranded Antisense siRNAs Guide Target RNA Cleavage in RNAi", Cell, Sep. 6, 2002, pp. 563-574, vol. 110.
Mary K. Montgomery et al., "RNA as a Target of Double-Stranded RNA-Mediated Genetic Interference in Caenorhabditis elegans", Proceedings of the National Academy of Sciences of the United States of America, Dec. 22, 1998, pp. 15502-15507, vol. 95, No. 26.
Mary K. Montgomery, et al., Double-stranded RNA As a Mediator in Sequence-Specific Genetic Silencing and Co-Suppression, TIG, vol. 14 No. 7, pp. 255-256 and 256, Jul. 1998.
Mccaffrey, AP et al., Nature (2000), vol. 418, pp. 38-39.
Michael T. Mcmanus, et al. Gene Silencing in Mammals by Small Interfering RNAs, Center for Cancer Research Massachusetts, vol. 3, pp. 737-750, Oct. 2002.
Michael Y. X. Ma, et al., Design and Synthesis of RNA Miniduplexes via a Synthetic Linker Approach, Biochemistry, vol. 32, No. 7, 1993, pp. 1751-1758.
Mohammad B. Bahramian. et al., Transcriptional and Post-transcriptional Silencing of Rodent 01 (1) collagen by a Homologous Transcriptionally Self-Silenced Transgene, R125 Molecular and Cellular Bioloqy, Jan. 1999, vol. 19, No. 1. pp. 274-283.
Morrissey et al. "Activity of stabilized short interfering RNA in a mouse model of hepatitis B virus replication." Hepatology. Jun. 2005;41(6):1349-56.
Morrissey, D. V. et al. "Chemical Modification of Synthetic siRNA", Pharmaceutical Discovery, May 13, 2005.
Napoli, et al., Introduction of a Chimeric Chalcone Synthase Gene into Petunia Results in Reversible Co-Suppression of Homologous Genes in trans, The Plant Cell, vol. 2, pp. 279-289, Apr. 1990.
News of the Week, Science, Candidate Gene Silencers Found, Fetal Cells Help Parkinson's Patients, Science, vol. 286, p. 886, Dec. 1999.

(56) References Cited

OTHER PUBLICATIONS

Ngo et al., PNAS, vol. 95, Dec. 1998, p. 14687.
Nikiforov, T. T. et al., Oligodeoxynucleotides Containing 4-Thiothymidine and 6-Thiodeoxyguanosine as Affinity Labels for the Eco RV Restriction Endo nuclease and Modification Methylase. Nucleic Acids Research, 1992, vol. 20, pp. 1209-1214.
Notice of Opposition to a European Patent dated Oct. 4, 2007 against EPO Patent No. 1 527 176 (EP Patent Application No. 03 784 183.0), Opponent Alnylam Pharmaceuticals, Inc., pp. 1-27.
Notice of Opposition to a European Patent dated Oct. 4, 2007 against EPO Patent No. 1527176 (EP Patent Application No. 03 784 183.0), Opponent Dr. Martin Grund, pp. 1-16.
Notice of Opposition to a European Patent dated Oct. 4, 2007 against EPO Patent No. 1527176 (EP Patent Application No. 03 784 183.0), Opponent Sirna Therapeutics, Inc., Inc., pp. 1-22.
Oates, et al., Too Much Interference: Injection of Double-Stranded RNA Has Nonspecific Effects in the Zebrafish Embryo, Developmental Biology, Aug. 2000, pp. 20-28, vol. 224, Issue 1.
Oliveira, S. et al. "Targeted Delivery of siRNA", Journal of Biomedicine and Biotechnology, 2006, pp. 1-9, vol. 2006.
Opposition filed on behalf of Alcon Laboratories, Inc. in EPO Patent No. 1 527 176 (EP Patent Application No. 03 784 183.0) dated Sep. 26, 2007, pp. 1-21.
Orum, H. et al. Locked nucleic acids: A promising molecular family for gene-function analysis and antisense drug developmene Current Opinion in Molecular Therapeutics, 2001, pp. 239-243, vol. 3, No. 3.
P. Dan Cook, "Medicinal Chemistry of Antisense Oligoucleotides"; (ed. Crroke, S.T.), pp. 29-56 Marcel Dekker, NY 2001.
Paddison, et al.,Stable suppression of gene expression by RNAi in mammalian cells; PNAS, 99(3); pp. 1443-1448; (2002).
Pancoska, P. et al. "Efficient RNA interference depends on global context of the target sequence: quantitative analysis of silencing efficiency using Eulerian graph representation of siRNA", Nucleic Acids Research, 2004, pp. 1469-1479, vol. 32, No. 4.
Park, et al., "Prevention of HIV-1 infection in human peripheral blood mononuclear cells by specific RNA interference;" Nucleic Acids Res., vol. 30, No. 22, pp. 4830-4835; (2002).
Parrish, S. et al. "Functional Anatomy of a dsRNA Trigger: Differential Requirement for the Two Trigger Strands in RNA Interference", Molecular Cell, Nov. 2000, pp. 1077-1087, vol. 6.
Patel, D. J. et al. "Structural Biology of RNA Silencing and Its Functional Implications", Cold Spring Harbor Symposia on Quantitative Biology, 2006, pp. 81-93, vol. LXXI.
Patentee's "Statement of Grounds of Appeal" against EP 1144623, Feb. 5, 2007, pp. 1-38.
Patrick J. Paddison, et al., Short Hairpin RNAs (shRNAs) Induce Sequence-Specific Silencing in Mammalian Cells, Genes & Development vol. 16, pp. 948-958, 2002.
Peek, A. S. et al. "Design of Active Small Interfering RNAs", Current Opinion in Molecular Therapeutics, 2007, pp. 110-118, vol. 9, No. 2.
Pei, Y. et al. "On the Art of Identifying Effective and Specific siRNAs", Nature Methods, Sep. 2006, pp. 670-676, vol. 3, No. 9.
Perler, Nucl. Acids Res., vol. 30, No. 1, pp. 383-384, 2002.
Peter M. Waterhouse et al., "Gene silencing as an adaptive defense against viruses", Nature, Jun. 14, 2001, pp. 834-842, vol. 411.
Peter M. Waterhouse, et al., Virus resistance and gene silencing in plants can be induced by simultaneous expression of sense and antisense RNA, Communicated by W. James Peacock, Commonwealth Scientific and Industrial Research Organization, Canberra, Australia, Aug. 17, 1998, vol. 95, pp. 13959-13964.
Philip D. Zamore, et al., RNAi: Double-Stranded RNA Directs the ATP-Dependent Cleavage of mRNA at 21 to 23 Nucleotide Intervals, Cell, vol. 101, pp. 25-33, Mar. 31, 2000.
Phillip A Sharp, RNAi and Double-strand RNA, Genes & Development, vol. 13, pp. 139-141, Cold Spring Harbor Laboratory Press, 1999.
Phillip A, Sharp, "RNA interference-2001", Genes & Development, 2001, pp. 485-490, vol. 15.

Pierre G. Milhaud, et al., Free and Liposome-encapsulated Double-Stranded RNAs as Inducers of Interferon, Interleukin6, and Cellular Toxicity, Journal of Interferon Research vol. 11, pp. 261-265,1991.
Potera, C. "Antisense—down, but not out", Nature Biotechnology, May 2007, pp. 497-499, vol. 25, No. 5.
Poui Nielsen, et al., A Novel Class of Conformationally Restricted Oligonucleotide Analogues: Synthesis of 2',3'-Bridged Monomers and RNA-Selective Hybridisation, Chern. Commun., 1997, pp. 825-826.
Priority Document of 9927444.1, Cancer Res. Camp. Technol. Ltd. Inhibiting Gene Expression, Publ. Nov. 19, 1999, Issued Nov. 22, 2000.
Priority Document of U.S. Appl. No. 60/117,635, Double-Stranded RNA Blocks Specific Gene Expression in Multicellular Settings in in Vivo and in Vitro, Mar. 14, 2000.
Priority Document of U.S. Appl. No. 60/130,377, Methods and Compositions for Inhibiting the Function of Polynucleotide, Issued Jun. 6, 2000.
R. Kreutzer, et al., Specific Inhibition of Viral Gene Expression by Double-Stranded RNA in vitro, Nature 391, p. 806, 1998.
R. Schlingenslepen et al., Antisense—From Technology to Therapy, EX L 1 BRIS [ROCHE], 1997, vol. 6, pp. 30-58.
Rana, T. M. "Illuminating the silence: understanding the structure and function of small RNAs", Molecular Cell Biology, Jan. 2007, pp. 23-36, vol. 8.
Rand, T. A. et al. "Argonaute2 Cleaves the Anti-Guide Strand of siRNA during RISC Activation", Cell, Nov. 18, 2005, pp. 621-629, vol. 123.
Ravinderjit S. Braich, et al., Regiospecific Solid-Phase Synthesis of Branched Oligonucleotides. Effect ofVicinal 2',5"(or 2',3'-) and 3',5"Phosphodiester Linkages on the Formation of Hairepin DNA, Bioconjuqate Chern., 1997, vol. 8, pp. 370-377.
Reiko Iwase et al., Gene Regulation by Decoy Approach (I): Synthesis and Properties of Photo-crosslinked Oligonucleotides, Nucleic Acids Symposium Series, 1997, No. 37, pp. 203-204.
Robert Barstead, "Genome-wide RNAi", Current Opinion in Chemical Biology, 2001, pp. 63-66, vol. 5.
Rosalind C. Iee, et al., The C. Elegans Heterochronic Gene Lin-4 Encodes Small RNAs with Antisense Complementarity to Lin-14, Cell, vol. 75, pp. 843-854, Dec. 3, 1993.
Rose et al. "Functional polarity is introduced by Dicer processing of short substrate RNAs" Nucleic Acids Research, 2005, pp. 4140-4156, vol. 33, No. 13.
Rossi, J. J. "A Cholesterol connection in RNAi", Nature, Nov. 11, 2004, pp. 155-156, vol. 432.
Rueyling Lin and Leon Avery, Policing Rogue Genes, Nature, vol. 402, pp. 128-129, Nov. 11, 1999.
S. Blair Hedges, Nature Reviews, Genetics (2002), vol. 3, pp. 838-849.
Sant El, A. et al. "RNA interference in the mouse vascular endothelium by systemic administration of siRNA-lipoplexes for cancer therapy", Gene Therapy, 2006, pp. 1360-1370, vol. 13.
Santel, A. "Get the balance right: Mitofusins roles in health and disease", Biochimica et Biophysica Acta, 2006, pp. 490-499, vol. 1763.
Santel, A. et al. "A novel siRNA-lipoplex technology for RNA interference in the mouse vascular endothelium", Gene Therapy, 2006, pp. 1222-1234, vol. 13.
Sayda M. Elbashir et al., "Duplexes of 21-nucleotide RNAs mediate RNA interference in cultured mammalian cells", Nature, May 24, 2001, pp. 494-498, vol. 411.
Sayda M. Elbashir, et al, Analysis of Gene Function in Somatic Mammalian Cells Using Small Interfering RNAs, Methods, vol. 26, 2002, pp. 199-213.
Sayda M. Elbashir, et al., Functional Anatomy of siRNAs for Mediating Efficient RNAi in Drosophila melanogaster embryo Lysate, The EMBO Journal vol. 20, No. 23, pp. 6877-6888, 2001.
Scherer, L. J. et al. "Approaches for the sequence-specific knockdown of mRNA", Nature Biotechnology, Dec. 2003, pp. 1457-1465, vol. 21, No. 12.
Schwarz, D. S. Evidence that siRNAs Function as Guides, Not Primers, in the Drosophila and Human RNAi Pathways, Molecular Cell, vol. 10, pp. 537-548, Sep. 2002.

(56) References Cited

OTHER PUBLICATIONS

Schwarzer, R. et al. "TRB3 is a PI 3-kinase dependent indicator for nutrient starvation", Cellular Signalling, 2006, pp. 899-909, vol. 18.
Sequence of dsRNA unc-22A, 2007, p. 1.
Sergei M. Gryaznov, et al., Template Controlled Coupling and Recombination of Oligonucleotide Blocks Containing Thiophosphoryl Groups, Nucleic Acids Research, 1993, vol. 21, No. 6, pp. 1403-1408.
Skripkin, E. et at, Psoralen Crosslinking Between Human Immunodeficiency Virus Type 1 RNA and Primer tRNA3Lys, Nucleic Acids Research, 1996, vol. 24, No. 3, pp. 509-514.
Sledz, CA., et al., Nature Cell Biol., vol. 5, p. 834-839, 2003.
Snove, O. et al. "Chemical Modifications Rescue Off-Target Effects of RNAi", ACS Chemical Biology, 2006, pp. 274-276, vol. 1, No. 5.
Soutschek, et al., Nature, vol. 432, 1-8, 2004.
Statement of Grounds of Appeal filed on behalf of Silence Therapeutics in EPO Patent No. 1 527 176 (EP 03 784 183.0) dated Jul. 26, 2010, pp. 1-237.
Stuart K. Kim, "Functional genomics: The worm scores a knockout", Current Biology, 2001, pp. R85-R87, vol. 11.
Sudhir Agrawal, et al., Self-Stabilized Oligonucleotides as Novel Antisense Agents, Nucleic Acids, Res., vol. 21, No. 11, 1993, pp. 2729-2735.
The Merriam Webster Dictionary, pp. 37 and 540, 1997, Merriam-Webster, Inc.
Thomas Horn, et al., Chemical Synthesis and Characterization of Branched Oligodeoxyribonucleotides (bONA) For Use As Signal Amplifiers in Nucleic Acid Quantification Assays, Nucleic Acids Research, 1997, vol. 25, No. 23, pp. 4842-4849.
Thomas Tuschl et al., "Targeted mRNA degradation by double-stranded RNA in vitro", Genes & Development, 1999, pp. 3191-3197, vol. 13.
Timmons L. Fire, A, Specific Interference by Ingested dsRNA, Nature, Dec. 1998, pp. 395.
Turner, J. J. et al. "MALDI-TOF mass spectral analysis of siRNA degradation in serum confirms an RNAse A-like activity", Molecular Biosystems, 2007, pp. 43-50, vol. 3.
Tusch, T. et al. "Small Interfering RNAs: A Revolutionary Tool for the Analysis of Gene Function and Gene Therapy", Molecular Interventions, Jun. 2002, pp. 158-167, vol. 2, Issue 3.
Tuschl, T. "Expanding small RNA interference", Nature Biotechnology, May 2002, pp. 446-448, vol. 20.
U.S. Appl. No. 10/205,309; (priority document for No. 1, filed Jul. 25, 2002).
Voinnet, O., and Baulcombe, DC., Nature (1997) vol. 398, p. 553.
Volpe, T. A. et al. "Regulation of Heterochromatic Silencing and Histone H3 Lysine-9 Methylation by RNAi", Science, Sep. 13, 2002, pp. 1833-1837, vol. 297.
Wargelius A, Ellingsen S. Fjose A, Double-stranded RNA Induces Specific Developmental Defects in Zebrafish Embryos, Biochem Biophys Res Commun., Sep. 16. 1999, vol. 1, pp. 156-161.
Wess et al., Managing Complexity, Early Days for RNAi, Biocentury, vol. 11, No. 12, p. 123, Mar. 2003.
Wikipedia (2008). "Muster (Struktur)," translation provided herewith, 5 pages.
Wikipedia entry relating to "Sequence motif", 2009, pp. 1-6.
Williams, "Dicing with siRNA." Nat Biotechnol. Feb. 2005;23(2):181-2.
Wilson, C. et al. "Building oligonucleotide therapeutics using non-natural chemistries", Current Opinion in Chemical Biology, 2006, pp. 607-614, vol. 10.
Wu, et al., "Identification and Partial Purification of Human Double Strand RNase Activity"; The Journal of Biological Chem; vol. 273, No. 6, pp. 2532-2542 (1998).
Yang Shi, et al., A CBP/p300 Homolog Specifies Multiple Differentiation Pathways in Caenorhabditis Elegans, Genes & Development, vol. 12, No. 7, pp. 943-955, Apr. 1, 1998.
Zamore et al. "RNAi: double-stranded RNA directs the ATP-dependent cleavage of mRNA at 21to23 nucleotide intervals." Cell. Mar. 31, 2000; 101(1):25-33.
Zeng, et al., RNA, vol. 8, pp. 855-860, 2002.
Zhang, et al. "Targeted Gene Silencing by Small Interfering RNA based Knock-down Technology", Current Pharmaceutical Biotechnology, 2004, pp. 1-7, vol. 5.
Zhao, et al., Developmental Biol., vol. 229, pp. 215-223, 2001.
Zheng, et al., RNA, vol. 10, pp. 1934-1945, 2004.

\* cited by examiner

Fig. 2
☐ groups of modified nucleotides
— groups of unmodified nucleotides
Fig. 2A
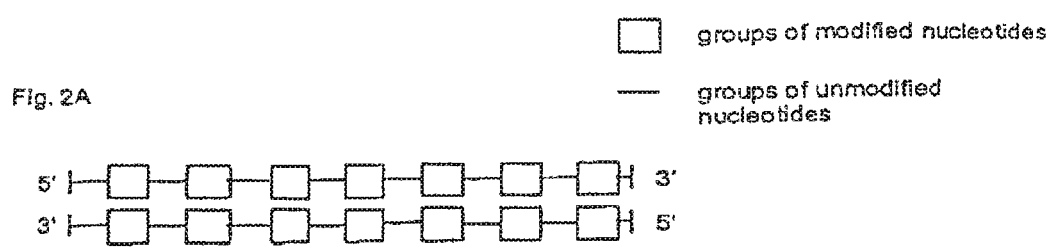
Fig. 2B
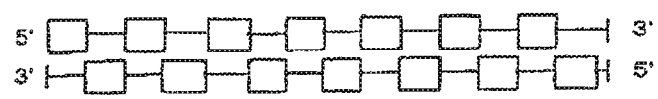
Fig. 2C
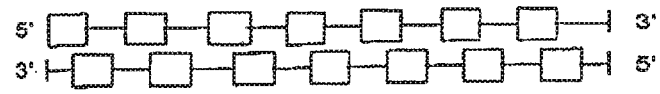

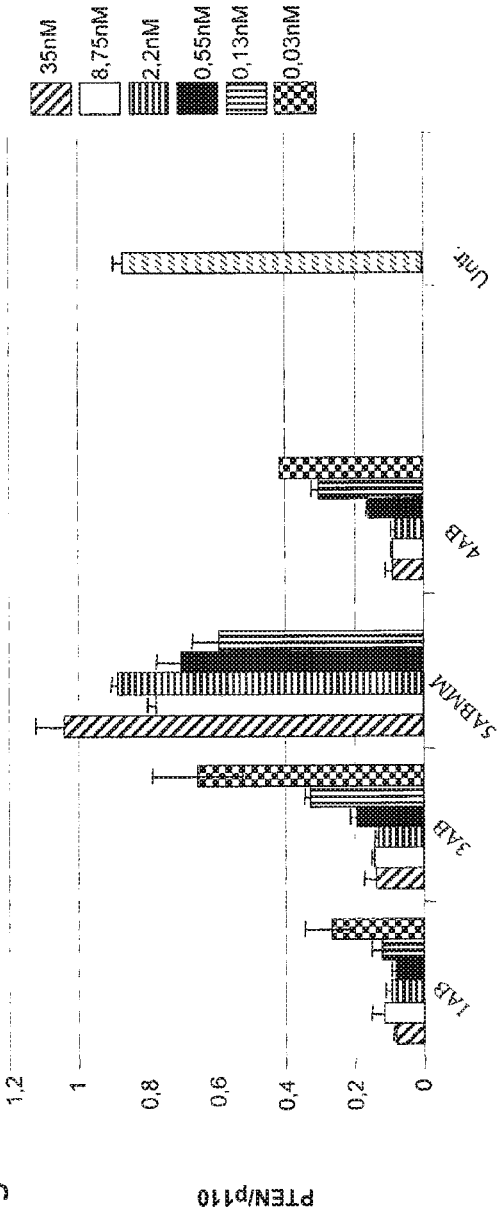

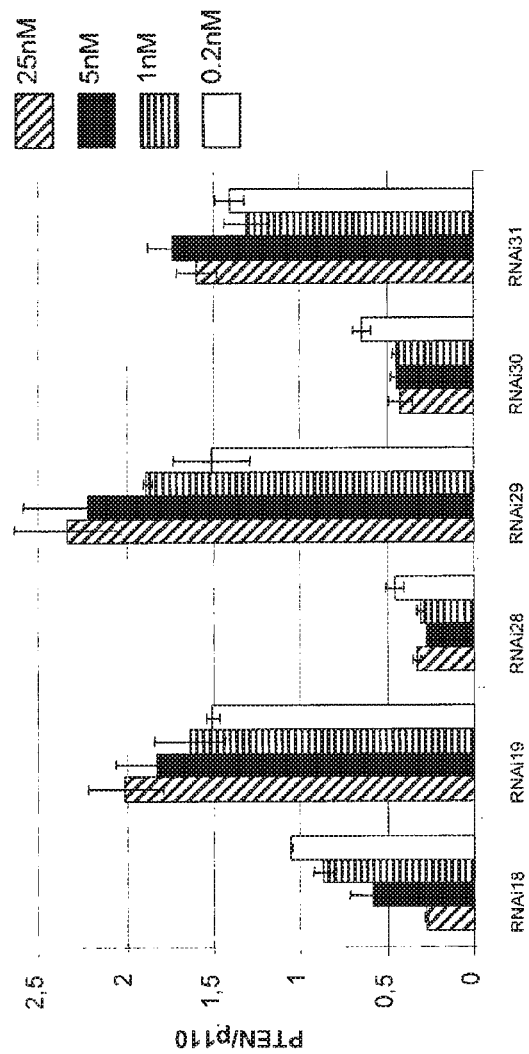

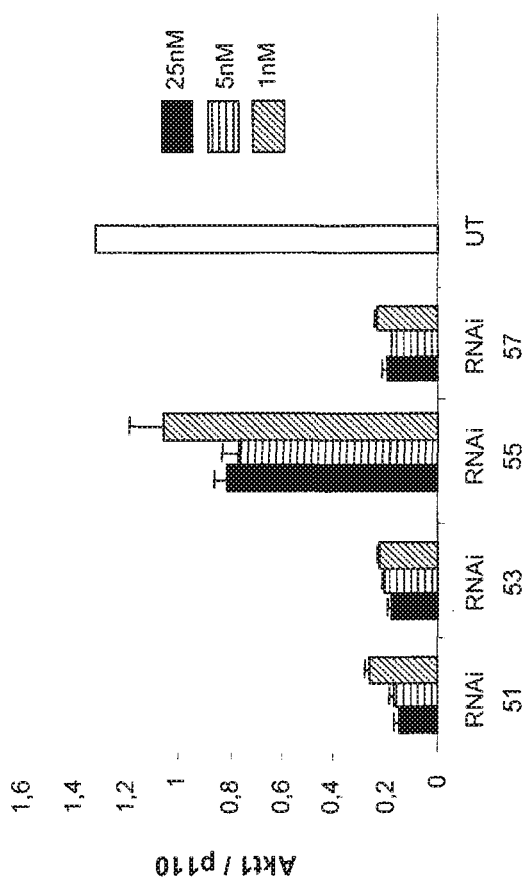

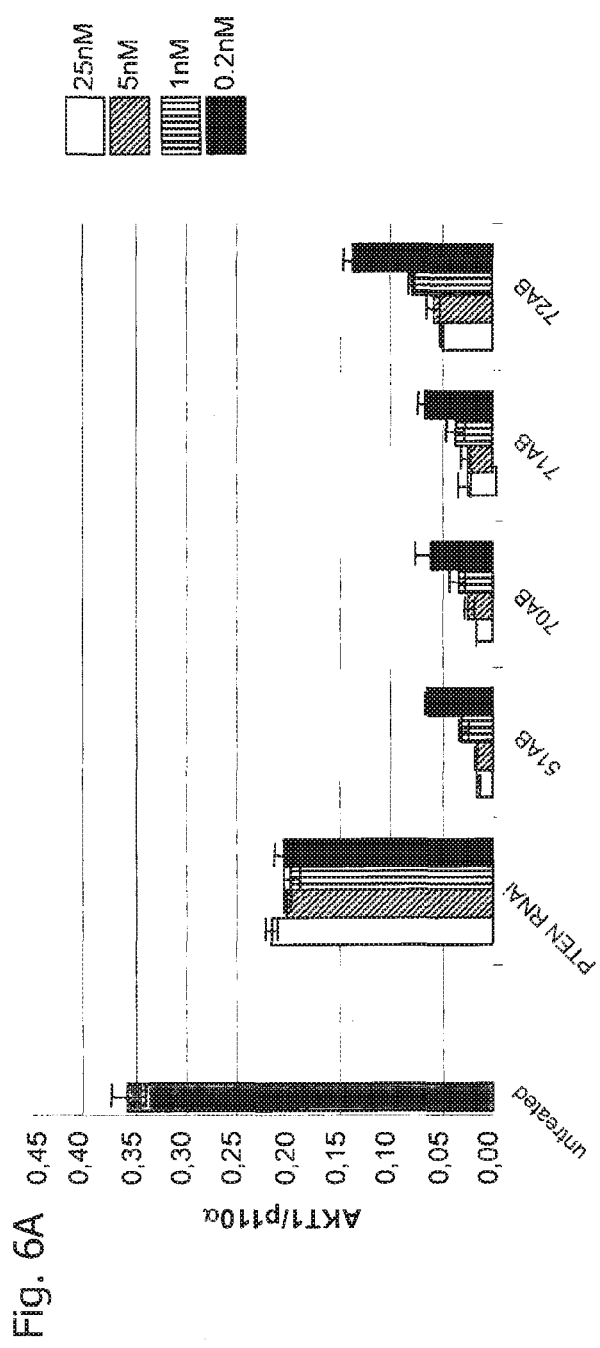

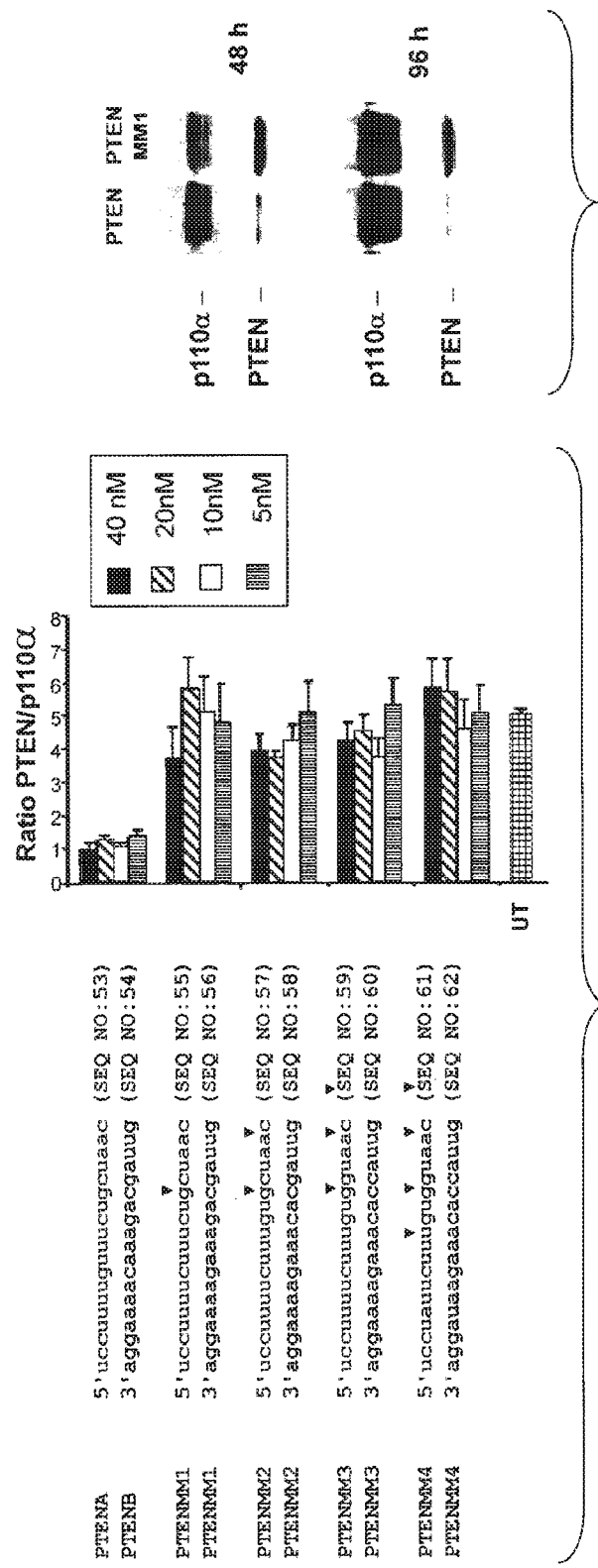

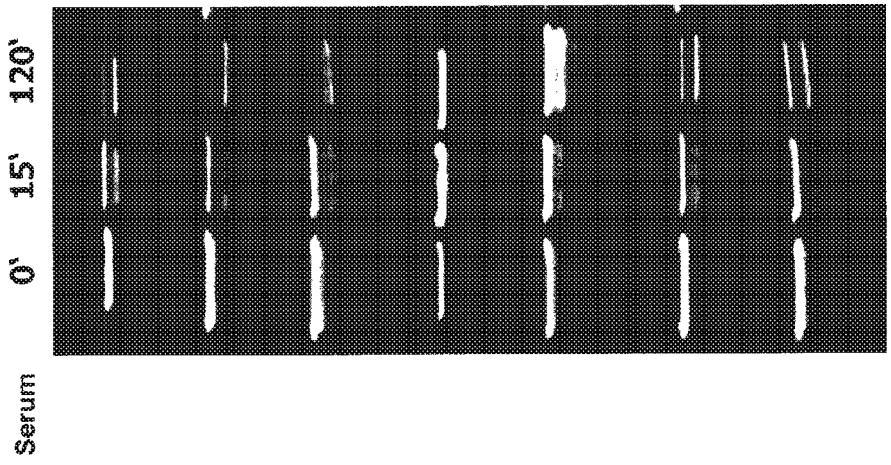

Tuschl
18A    5'-    cuccuuuguuucucugcuaacg-TT (SEQ ID NO:9)
18B    3'-TT-gaggaaacaaagacgauugc    (SEQ ID NO:10)

inverted abasic on both ends and 2TT
24A    5'-    iB-cuccuuuguuucugcuaacg-TT-iB (SEQ ID NO:63)
24B    3'-iB-TT-gaggaaacaaagacgauugc-iB    (SEQ ID NO:64)

NH2groups at both ends AND 2-deoxy
26A    5'-    NH2-cuccuuuguuucugcuaacg-TT-NH2 (SEQ ID NO:65)
26B    3'-NH2-TT-gaggaaacaaagacgauugc-NH2    (SEQ ID NO:66)

2'-O-Methyl modified with 2-deoxy at each end
79A    5'-    cuccuuuguuucugcuaacg-TT (SEQ ID NO:67)
79B    3'-    TT-gaggaaacaaagacgauugc  (SEQ ID NO:68)

Only RNA
28A    5'-    cuccuuuguuucugcuaacg-  (SEQ ID NO:13)
28B    3'-    gaggaaacaaagacgauugc-  (SEQ ID NO:14)

Only RNA with 2-deoxy at each 5' end
30A    5'-TT-cuccuuuguuucugcuaacg-   (SEQ ID NO:17)
30B    3'-    gaggaaacaaagacgauugc-TT (SEQ ID NO:69)

NH2 groups at each 3'end and 2-deoxy
3A     5'-    cuccuuuguuucugcuaacg-TT-NH2 (SEQ ID NO:70)
3B     3'-NH2-TT-gaggaaacaaagacgauugc-(SEQ ID NO:71)

FIG. 9B

| | | |
|---|---|---|
| 26A | 5'- | NH2-cuccuuuuguuucugcuaacg-TT-NH2 (SEQ ID NO:72) |
| 26B | 3'- | NH2-TT-gaggaaaacaaagacgauugc-NH2 (SEQ ID NO:77) |
| 24A | 5'- | iB-cuccuuuuguuucugcuaacg-TT-iB (SEQ ID NO:73) |
| 26B | 3'- | NH2-TT-gaggaaaacaaagacgauugc-NH2 (SEQ ID NO:77) |
| 22A | 5'- | cuccuuuuguuucugcuaacg-TT-iB (SEQ ID NO:74) |
| 26B | 3'- | NH2-TT-gaggaaaacaaagacgauugc-NH2 (SEQ ID NO:77) |
| 20A | 5'- | cuccuuuuguuucugcuaacg-TT-NH2 (SEQ ID NO:75) |
| 26B | 3'- | NH2-TT-gaggaaaacaaagacgauugc-NH2 (SEQ ID NO:77) |
| 18A | 5'- | cuccuuuuguuucugcuaacg-TT (SEQ ID NO:78) |
| 26B | 3'- | NH2-TT-gaggaaaacaaagacgauugc-NH2 (SEQ ID NO:77) |
| 30A | 5'- | TT-cuccuuuuguuucugcuaacg- (SEQ ID NO:76) |
| 26B | 3'- | NH2-TT-gaggaaaacaaagacgauugc-NH2 (SEQ ID NO:77) |
| 28A | 5'- | cuccuuuuguuucugcuaacg- (SEQ ID NO:80) |
| 26B | 3'- | NH2-TT-gaggaaaacaaagacgauugc-NH2 (SEQ ID NO:77) |
| 18A | 5'- | cuccuuuuguuucugcuaacg-TT (SEQ ID NO:78) |
| 18B | 3'- | TT-gaggaaaacaaagacgauugc (SEQ ID NO:79) |

FIG. 9C

-nnnnnnnnnnn-tt
NH2-nnnnnnnnnnnnnn-NH2          functional

-nnnnnnnnnnnnnn-tt-NH2
NH2-nnnnnnnnnnnnnn-NH2          functional

NH2-nnnnnnnnnnnnnn-tt-NH2
tt-nnnnnnnnnnnnnn-tt            not functional

Fig. 10B

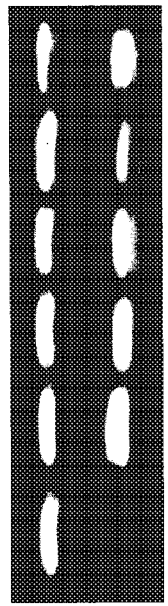

INPUT

2h Serum

RNA Bold italics represents 2'O-methyl

| | | | |
|---|---|---|---|
| 28A | 5'- | cuccuuuguuucucugcuaacg- | (SEQ ID NO:13) |
| 28B | 3'- | gaggaaaacaaagacgauugc | (SEQ ID NO:14) |
| 29A | 5'- | cuccuuucuuugugugcuaacg | (SEQ ID NO:81) |
| 29B | 3'- | gaggaaaacaaacacgauugc | (SEQ ID NO:82) |
| 73A | 5'- | cuccuuuguuucucugcuaacg- | (SEQ ID NO:83) |
| 73B | 3'- | -gaggaaaacaaagacgauugc- | (SEQ ID NO:84) |
| 74A | 5'- | cuccuuuguuucugcuaacg- | (SEQ ID NO:85) |
| 74B | 3'- | -gaggaaaacaaagacgauugc- | (SEQ ID NO:86) |
| 75A | 5'- | cuccuuuguuucugcuaacg- | (SEQ ID NO:87) |
| 75B | 3'- | -gaggaaaacaaagacgauugc- | (SEQ ID NO:88) |
| 79A | 5'- | *cuccuuuguuucugcuaacg-* | (SEQ ID NO:89) |
| 79B | 3'- | *-gaggaaaacaaagacgauugc-* | (SEQ ID NO:90) |
| 28A | 5'- | cuccuuuguuucucugcuaacg- | (SEQ ID NO:80) |
| 79B | 3'- | *-gaggaaaacaaagacgauugc-* | (SEQ ID NO:90) |
| 79A | 5'- | *cuccuuuguuucugcuaacg-* | (SEQ ID NO:89) |
| 28B | 3'- | gaggaaaacaaagacgauugc | (SEQ ID NO:14) |
| 75A | 5'- | cuccuuuguuucugcuaacg- | (SEQ ID NO:87) |
| 79B | 3'- | *-gaggaaaacaaagacgauugc-* | (SEQ ID NO:90) |

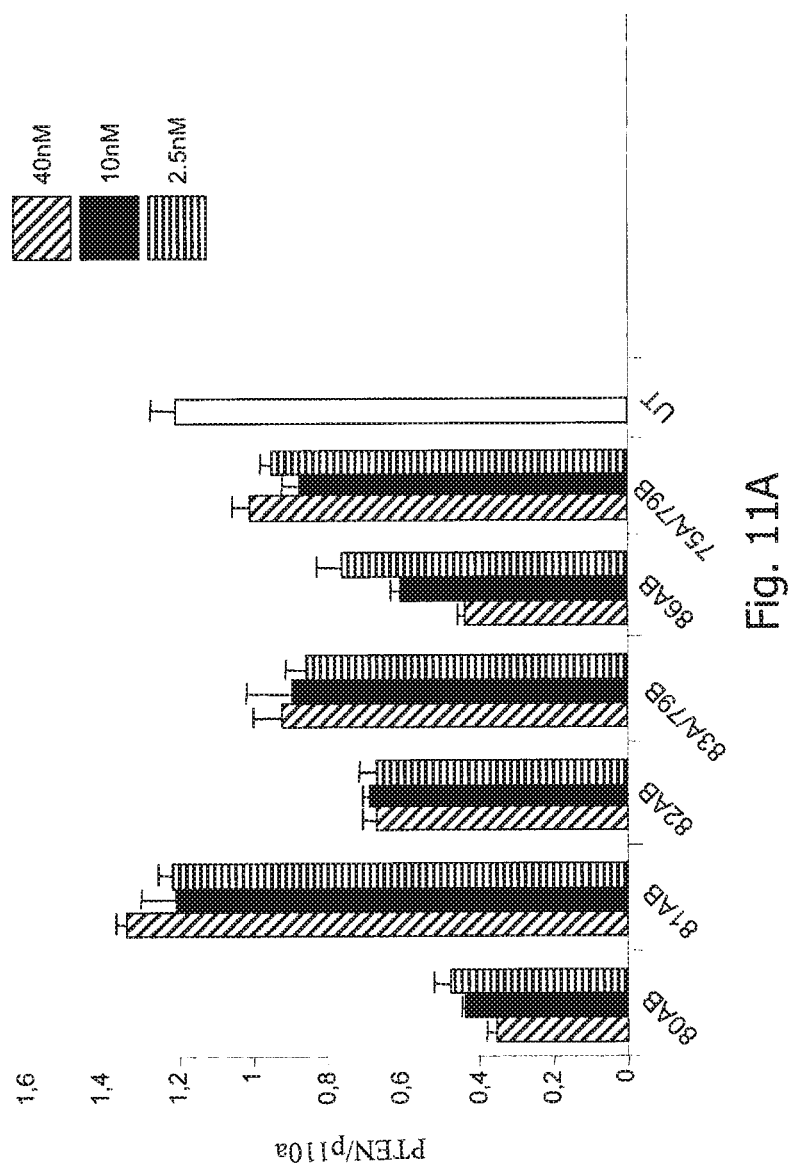

Fig. 11B

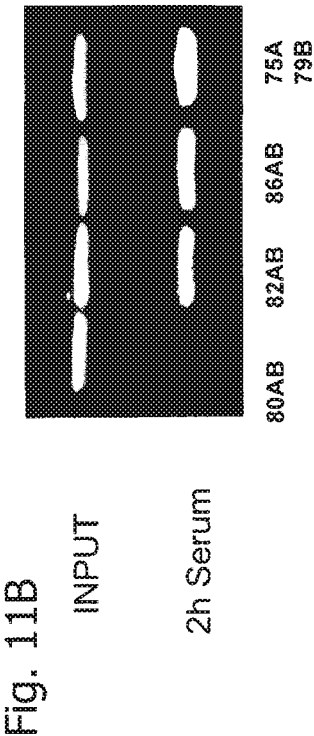

Fig. 11C

| RNA | Bold Italics represents 2'O-methyl | |
|---|---|---|
| 80A | 5'- cuccuuuguuucugcuaacg- | (SEQ ID NO:91) |
| 80B | 3'- -gaggaaaacaaagacgauugc- | (SEQ ID NO:92) |
| 81A | 5'- *cuccuuuguuu*cugcuaacg- | (SEQ ID NO:93) |
| 81B | 3'- -gaggaaaacaaagacgauugc- | (SEQ ID NO:94) |
| 82A | 5'- cuccuuuguuucugcuaacg- | (SEQ ID NO:95) |
| 82B | 3'- *gaggaaaacaaagacgauugc*- | (SEQ ID NO:96) |
| 83A | 5'- cuccuuuguuucugcuaacg- | (SEQ ID NO:97) |
| 79B | 3'- -*gaggaaaacaaagacgauugc*- | (SEQ ID NO:90) |
| 86A | 5'- *cuccuuuguuucugcuaacg*- | (SEQ ID NO:98) |
| 86B | 3'- -*gaggaaaacaaagacgauugc*- | (SEQ ID NO:99) |
| 75A | 5'- *cuccuuuguuucugcuaacg*- | (SEQ ID NO:100) |
| 79B | 3'- -*gaggaaaacaaagacgauugc*- | (SEQ ID NO:90) |

RNA Bold Italics represents 2' O-methyl

| | | | |
|---|---|---|---|
| 28A | 5'- | cuccuuuguuucugcuaacg- | (SEQ ID NO:101) |
| 28B | 3'- | gaggaaaacaaagacgauugc- | (SEQ ID NO:102) |
| 79A | 5'- | *cuccuuugu*uucug*cuaacg*- | (SEQ ID NO:103) |
| 79B | 3'- | *gaggaaaac*aaaga*cgauugc*- | (SEQ ID NO:104) |
| 81A | 5'- | *cuccuuugu*uucugcuaacg- | (SEQ ID NO:105) |
| 81B | 3'- | *gaggaaaac*aaagacgauugc- | (SEQ ID NO:106) |
| 82A | 5'- | cuccuuuguuucug*cuaacg*- | (SEQ ID NO:107) |
| 82B | 3'- | gaggaaaacaaaga*cgauugc*- | (SEQ ID NO:108) |
| 86A | 5'- | cuccuuu*gu*uucug*cuaacg*- | (SEQ ID NO:109) |
| 86B | 3'- | *gaggaaaac*aaaga*cg*auugc- | (SEQ ID NO:110) |
| 94A1 | 5'- | *cu*ccuuu*gu*uucug*cuaacg*- | (SEQ ID NO:111) |
| 94B1 | 3'- | *ga*ggaaa*ac*aaaga*cgauugc*- | (SEQ ID NO:112) |
| 94A1 | 5'- | *cu*ccuuu*gu*uucug*cuaacg*- | (SEQ ID NO:113) |
| 94B2 | 3'- | *ga*ggaaa*ac*aaaga*cg*auugc- | (SEQ ID NO:114) |
| 94A2 | 5'- | *cu*ccuuu*gu*uucug*cu*aacg | (SEQ ID NO:115) |
| 94B1 | 3'- | *ga*ggaaa*ac*aaaga*cgauugc*- | (SEQ ID NO:116) |
| 94A2 | 5'- | *cu*ccuuu*gu*uucug*cu*aacg | (SEQ ID NO:117) |
| 94B2 | 3'- | *ga*ggaaa*ac*aaaga*cg*auugc | (SEQ ID NO:118) |

Fig. 12B

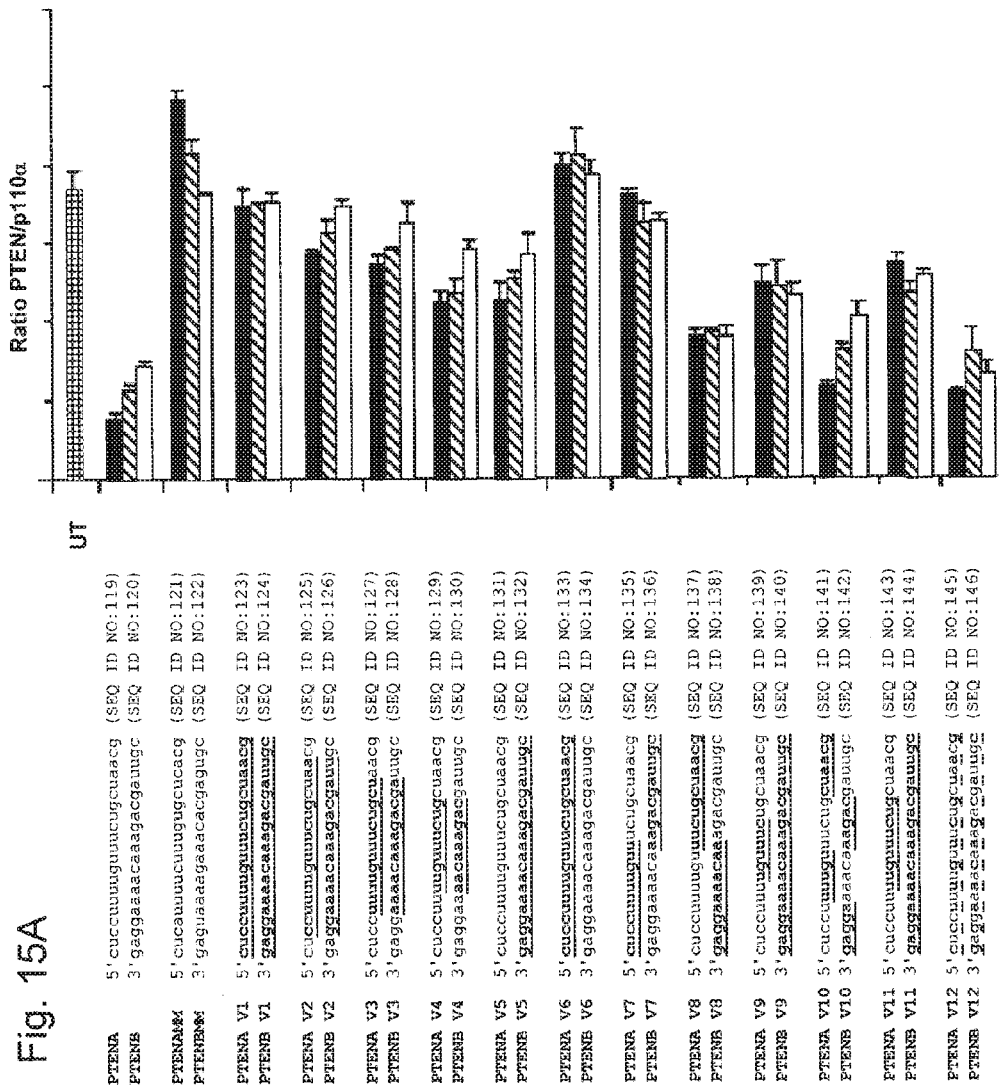

```
PTENA    5' cuccuuuuguuucugcuaacg  (SEQ ID NO:119)
PTENB    3' gaggaaaacaaagacgauugc  (SEQ ID NO:120)

PTENA V1  5' cuccuuuuguuucugcuaacg (SEQ ID NO:123)
PTENB V1  3' gaggaaaacaaagacgauugc (SEQ ID NO:124)

PTENA V7  5' cuccuuuuguuucugcuaacg (SEQ ID NO:135)
PTENB V7  3' gaggaaaacaaagacgauugc (SEQ ID NO:136)

PTENA V8  5' cuccuuuuguuucugcuaacg (SEQ ID NO:137)
PTENB V8  3' gaggaaaacaaagacgauugc (SEQ ID NO:138)

PTENA V10 5' cuccuuuuguuucugcuaacg (SEQ ID NO:141)
PTENB V10 3' gaggaaaacaaagacgauugc (SEQ ID NO:142)

PTENA V13 5' cuccuuuuguuucugcuaacg (SEQ ID NO:147)
PTENB V13 3' gaggaaaacaaagacgauugc (SEQ ID NO:148)

PTENA V14 5' cuccuuuuguuucugcuaacg (SEQ ID NO:149)
PTENB V14 3' gaggaaaacaaagacgauugc (SEQ ID NO:150)

PTENA V15 5' cuccuuuuguuucugcuaacg (SEQ ID NO:151)
PTENB V15 3' gaggaaaacaaagacgauugc (SEQ ID NO:152)

PTENA V12 5' cuccuuuuguuucugcuaacg (SEQ ID NO:145)
PTENB V12 3' gaggaaaacaaagacgauugc (SEQ ID NO:146)
```

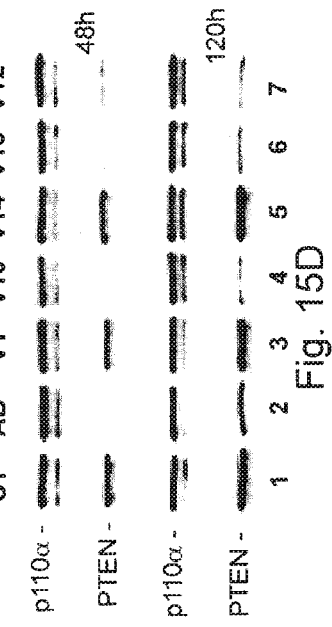

Fig. 15B

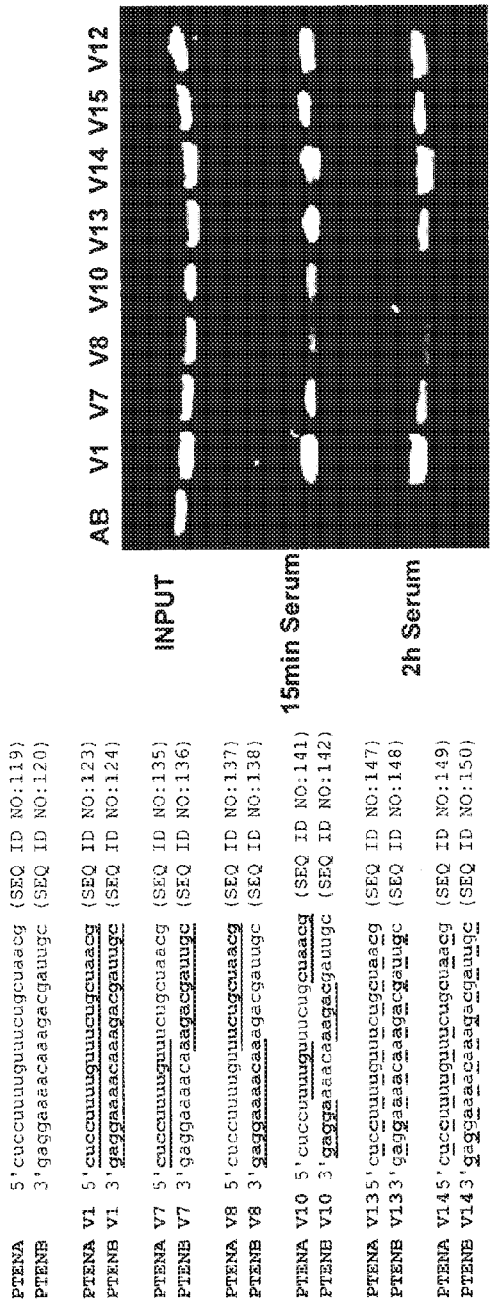

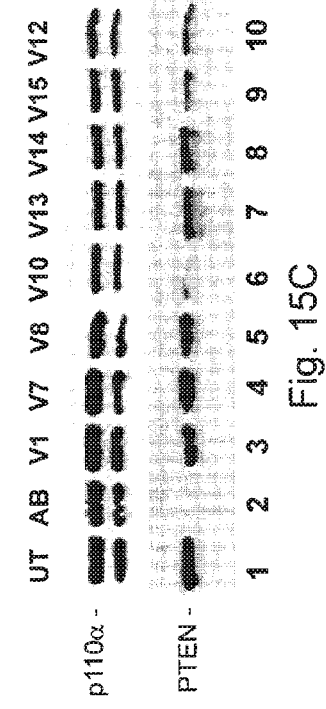

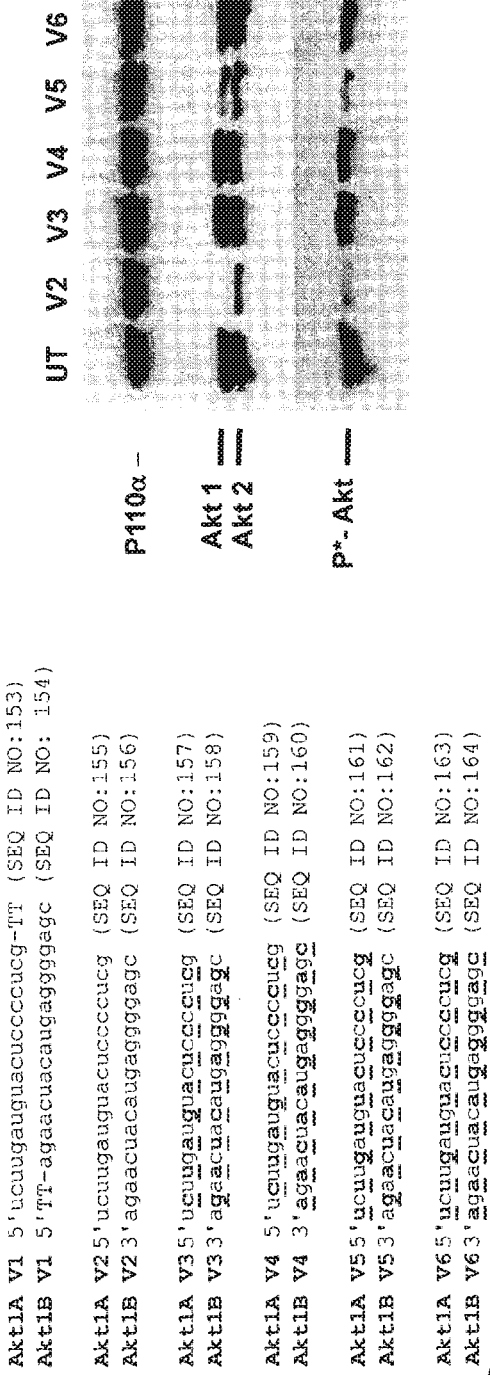
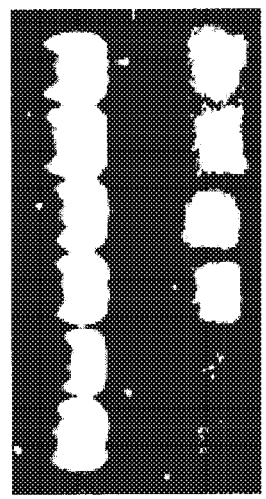

```
Akt1A V1 5' ucuugauguacucccccucg-TT (SEQ ID NO:153)
Akt1B V1 5'-TT-agaacuacaugagggagc (SEQ ID NO:154)

Akt1A V2 5' ucuugauguacucccccucg   (SEQ ID NO:155)
Akt1B V2 3' agaacuacaugagggagc     (SEQ ID NO:156)

Akt1A V3 5' ucuugauguacucccccucg   (SEQ ID NO:157)
Akt1B V3 3' agaacuacaugaggggagc    (SEQ ID NO:158)

Akt1A V4 5' ucuugauguacucccccucg   (SEQ ID NO:159)
Akt1B V4 3' agaacuacaugagggggagc   (SEQ ID NO:160)

Akt1A V5 5' ucuugauguacucccccucg   (SEQ ID NO:161)
Akt1B V5 3' agaacuacaugaggggagc    (SEQ ID NO:162)

Akt1A V6 5' ucuugauguacucccccucg   (SEQ ID NO:163)
Akt1B V6 3' agaacuacaugagggggagc   (SEQ ID NO:164)
```

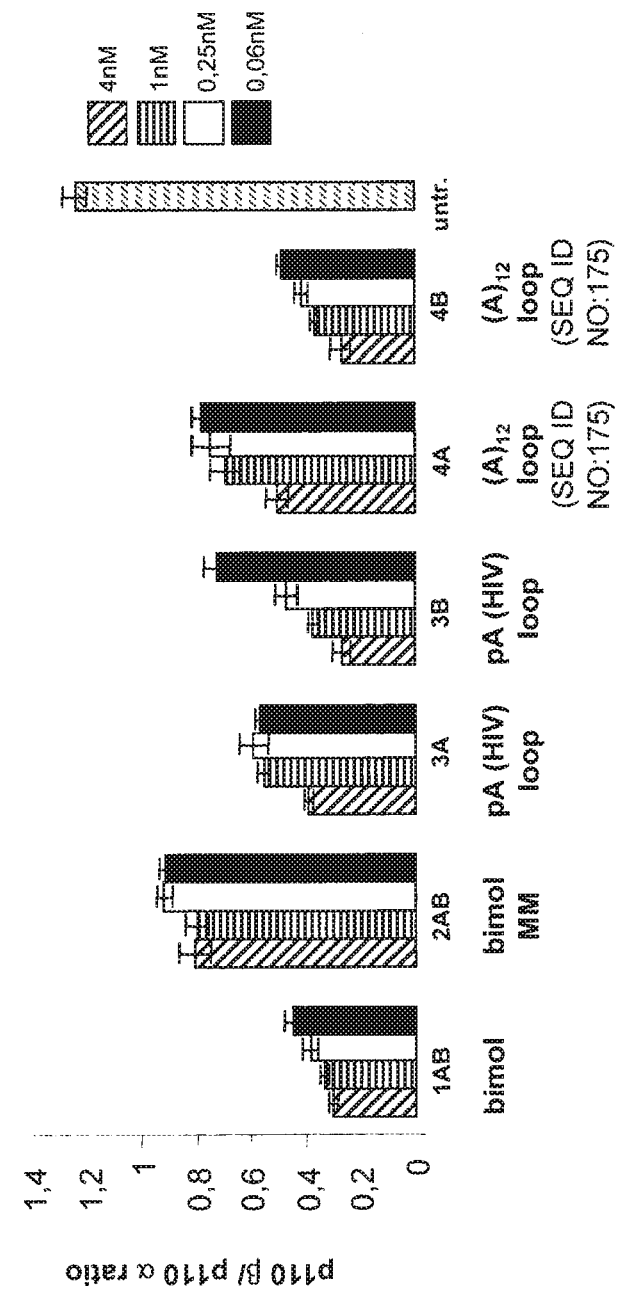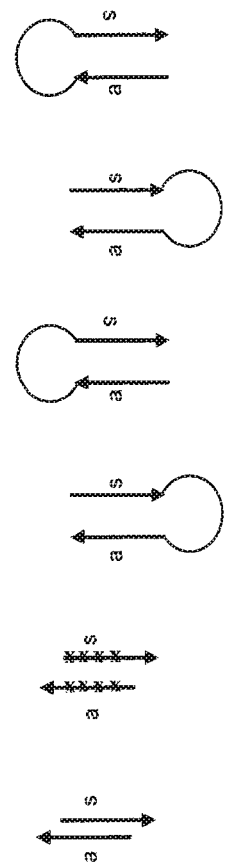
Fig. 17A
Fig. 17B

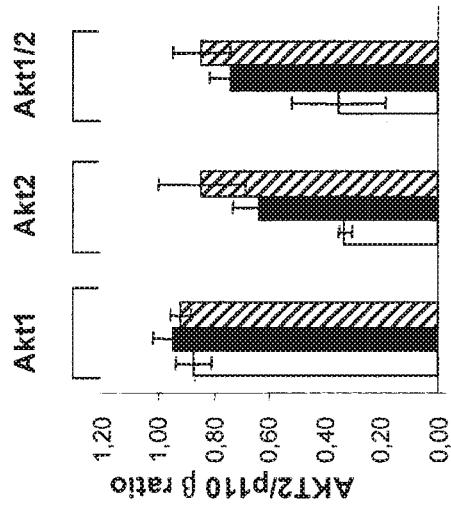
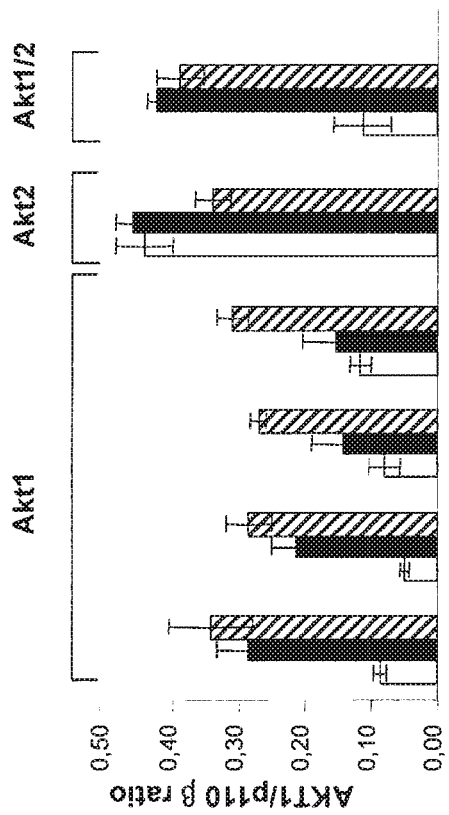
Fig. 18A
Fig. 18B

SEQUENCE LISTING

```
<160> NUMBER OF SEQ ID NOS: 182

<210> SEQ ID NO 1
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 1A (Fig 3B)

<400> SEQUENCE: 1
cuccuuuugu uucugcuaac gtt                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 1B (Fig. 3B)

<400> SEQUENCE: 2
cguuagcaga aacaaaagga gtt                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
```

```
<221> NAME/KEY: misc_feature
<222> LOCATION: (23)
<223> OTHER INFORMATION: NH2-modified
<220> FEATURE:
<223> OTHER INFORMATION: 3A (Fig. 3B)

<400> SEQUENCE: 3
cuccuuuugu uucugcuaac gtt                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: misc_feature
<222> LOCATION: (23)
<223> OTHER INFORMATION: NH2-modified
<220> FEATURE:
<223> OTHER INFORMATION: 3B (Fig. 3B)

<400> SEQUENCE: 4
cguuagcaga aacaaaagga gtt                                              23

<210> SEQ ID NO 5
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 4A (Fig. 3B)

<400> SEQUENCE: 5
cuccuuuugu uucugcuaac gtt                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 4B (Fig. 3B)

<400> SEQUENCE: 6
cguuagcaga aacaaaagga gtt                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
```

<220> FEATURE:
<223> OTHER INFORMATION: 5AMM (Fig. 3B)

<400> SEQUENCE: 7
cucauuuucu uugugcucac gtt                        23

<210> SEQ ID NO 8
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 5BMM (Fig. 3B)

<400> SEQUENCE: 8
cgugagcaca aagaaaauga gtt                        23

<210> SEQ ID NO 9
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 18A (Fig. 4B, 8B)

<400> SEQUENCE: 9
cuccuuuugu uucugcuaac gtt                        23

<210> SEQ ID NO 10
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 18B (Fig. 4B, 8B)

<400> SEQUENCE: 10
cguuagcaga aacaaaagga gtt                        23

<210> SEQ ID NO 11
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 19A(MM) (Fig. 4B)

<400> SEQUENCE: 11
cucauuuucu uugugcucac gtt                        23

```
<210> SEQ ID NO 12
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 19B(MM) (Fig. 4B)

<400> SEQUENCE: 12
cgugagcaca aagaaaauga gtt                                           23

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 28A (Fig. 4B, 8B, 9C, 10C)

<400> SEQUENCE: 13
cuccuuuugu uucugcuaac g                                             21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 28B (Fig. 4B, 8B, 9C, 10C)

<400> SEQUENCE: 14
cguuagcaga aacaaaagga g                                             21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 29A(MM) (Fig. 4B)

<400> SEQUENCE: 15
cucauuuucu uugugcucac g                                             21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 29B(MM) (Fig. 4B)

<400> SEQUENCE: 16
```

```
cgugagcaca aagaaaauga g                                               21

<210> SEQ ID NO 17
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 30A (Fig. 4B, 8B)

<400> SEQUENCE: 17
ttcuccuuuu guuucugcua acg                                             23

<210> SEQ ID NO 18
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 30B (Fig. 4B)

<400> SEQUENCE: 18
ttcguuagca gaaacaaaag gag                                             23

<210> SEQ ID NO 19
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 31A(MM) (Fig. 4B)

<400> SEQUENCE: 19
ttcucauuuu cuuugugcuc acg                                             23

<210> SEQ ID NO 20
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 31B(MM) (Fig. 4B)

<400> SEQUENCE: 20
ttcgugagca caaagaaaau gag                                             23

<210> SEQ ID NO 21
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      RNAi oligonucleotide
<220> FEATURE:
<223> OTHER INFORMATION: 51A (Fig. 5B)

<400> SEQUENCE: 21
ucuugaugua cuccccucgu u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 51B (Fig. 5B)

<400> SEQUENCE: 22
cgaggggagu acaucaagau u                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 53A (Fig. 5B)

<400> SEQUENCE: 23
ucuugaugua cuccccucgu u                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 53B (Fig. 5B)

<400> SEQUENCE: 24
cgaggggagu acaucaagac c                                              21

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 55A (Fig. 5A)

<400> SEQUENCE: 25
cuugauguac uccccucgu                                                 19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
```

```
<223> OTHER INFORMATION: 55B (Fig. 5B)

<400> SEQUENCE: 26 gagggagua caucaagac                                                      19

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 57A (Fig. 5B)

<400> SEQUENCE: 27
ucuugaugua cuccccucgt t                                                  21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 57B (Fig. 5B)

<400> SEQUENCE: 28 cgagggagu acaucaagac c                                                   21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 51A (Fig. 6B)

<400> SEQUENCE: 29
ucuugaugua cuccccucgu u                                                  21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 51B (Fig. 6B)

<400> SEQUENCE: 30 cgagggagu acaucaagau u                                                   21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
```

Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 70A (Fig. 6B)

<400> SEQUENCE: 31
ucuugaugua cuccccucgt t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 70B (Fig. 6B)

<400> SEQUENCE: 32
cgaggggagu acaucaagat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 71A (Fig. 6B)

<400> SEQUENCE: 33
acuugaugua cuccccucct t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 71B (Fig. 6B)

<400> SEQUENCE: 34
ggaggggagu acaucaagut t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 72A (Fig. 6B)

```
<400> SEQUENCE: 35
aguugaugua cuccccugct t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 72B (Fig. 6B)

<400> SEQUENCE: 36 gcagggagu acaucaacut t                                               21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1 1A (Fig. 7A)

<400> SEQUENCE: 37
ucuugaugua cuccccucgu u                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1 1B (Fig. 7A)

<400> SEQUENCE: 38 cgagggagu acaucaagau u                                               21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1 2A (Fig. 7A)

<400> SEQUENCE: 39
ucuugaugua cuccccucgu u                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1 2B (Fig. 7A)

<400> SEQUENCE: 40
```
cgaggggagu acaucaagac c                                                      21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 3A (Fig. 7A)

<400> SEQUENCE: 41
ucuugaugua cuccccucgt t                                                      21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 3B (Fig. 7A)

<400> SEQUENCE: 42
cgaggggagu acaucaagac c                                                      21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 4A (Fig. 7A)

<400> SEQUENCE: 43
ucuugaugua cuccccucgt t                                                      21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 4B (Fig. 7A)

<400> SEQUENCE: 44
cgaggggagu acaucaagat t                                                      21

<210> SEQ ID NO 45
<211> LENGTH: 19
<212> TYPE: RNA

```
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1 5A (Fig. 7A)

<400> SEQUENCE: 45
cuugauguac uccccucgu                                                      19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1 5B (Fig. 7A)

<400> SEQUENCE: 46 gagggagua caucaagac                                                       19

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 6A (Fig. 7A)

<400> SEQUENCE: 47
acuugaugua cuccccucct t                                                   21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 6B (Fig. 7A)

<400> SEQUENCE: 48
ggaggggagu acaucaagut t                                                   21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 7A (Fig. 7A)

<400> SEQUENCE: 49
aguugaugua cuccccugct t                                                   21
```

```
<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1 7B (Fig. 7A)

<400> SEQUENCE: 50
gcaggggagu acaucaacut t                                                    21

<210> SEQ ID NO 51
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: PTEN 1A (Fig. 7A)

<400> SEQUENCE: 51
cuccuuuugu uucugcuaac gtt                                                  23

<210> SEQ ID NO 52
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: PTEN 1B (Fig. 7A)

<400> SEQUENCE: 52
cguuagcaga aacaaaagga gtt                                                  23

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA (Fig. 7B)

<400> SEQUENCE: 53
uccuuuuguu ucugcuaac                                                       19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
```

<223> OTHER INFORMATION: PTENB (Fig. 7B)

<400> SEQUENCE: 54
guuagcagaa acaaaagga                                                    19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM1 (Fig. 7B)

<400> SEQUENCE: 55
uccuuuucuu ucugcuaac                                                    19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM1 (complementary sequence, Fig. 7B)

<400> SEQUENCE: 56
guuagcagaa agaaaagga                                                    19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM2 (Fig. 7B)

<400> SEQUENCE: 57
uccuuuucuu ugugcuaac                                                    19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM2 (complementary sequence, Fig. 7B)

<400> SEQUENCE: 58
guuagcacaa agaaaagga                                                    19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM3 (Fig. 7B)

<400> SEQUENCE: 59
uccuuuucuu ugugguaac                                           19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM3 (complementary sequence, Fig. 7B)

<400> SEQUENCE: 60
guuaccacaa agaaaagga                                           19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM4 (Fig. 7B)

<400> SEQUENCE: 61
uccuauucuu ugugguaac                                           19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENMM4 (complementary sequence, Fig. 7B)

<400> SEQUENCE: 62
guuaccacaa agaauagga                                           19

<210> SEQ ID NO 63
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 24A (Fig. 8B)

<400> SEQUENCE: 63
cuccuuuugu uucugcuaac gtt                                      23

<210> SEQ ID NO 64
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 24B (Fig. 8B)

```
<400> SEQUENCE: 64
cguuagcaga aacaaaagga gtt                                              23

<210> SEQ ID NO 65
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 26A (Fig. 8B)
<220> FEATURE:
<221> NAME/KEY: misc_feature
<222> LOCATION: (1)
<223> OTHER INFORMATION: NH2-modified
<220> FEATURE:
<221> NAME/KEY: misc_feature
<222> LOCATION: (23)
<223> OTHER INFORMATION: NH2-modified

<400> SEQUENCE: 65
cuccuuuugu uucugcuaac gtt                                              23

<210> SEQ ID NO 66
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 26B (Fig. 8B)
<220> FEATURE:
<221> NAME/KEY: misc_feature
<222> LOCATION: (1)
<223> OTHER INFORMATION: NH2-modified
<220> FEATURE:
<221> NAME/KEY: misc_feature
<222> LOCATION: (23)
<223> OTHER INFORMATION: NH2-modified

<400> SEQUENCE: 66
cguuagcaga aacaaaagga gtt                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: modified_base
<222> LOCATION: (1)..(21)
<223> OTHER INFORMATION: 2'-O-methyl modified RNA
<220> FEATURE:
<223> OTHER INFORMATION: 79A (Fig. 8B)

<400> SEQUENCE: 67
cuccuuuugu uucugcuaac gtt                                              23
```

```
<210> SEQ ID NO 68
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: modified_base
<222> LOCATION: (1)..(21)
<223> OTHER INFORMATION: 2'-O-methyl modified RNA
<220> FEATURE:
<223> OTHER INFORMATION: 79B (Fig. 8B)

<400> SEQUENCE: 68
cguuagcaga aacaaaagga gtt                                              23

<210> SEQ ID NO 69
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 30B (Fig. 8B)

<400> SEQUENCE: 69
ttcguuagca gaaacaaaag gag                                              23

<210> SEQ ID NO 70
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: misc_feature
<222> LOCATION: (23)
<223> OTHER INFORMATION: NH2-modified
<220> FEATURE:
<223> OTHER INFORMATION: 3A (Fig. 8B)

<400> SEQUENCE: 70
cuccuuuugu uucugcuaac gtt                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: misc_feature
<222> LOCATION: (23)
<223> OTHER INFORMATION: NH2-modified
<220> FEATURE:
<223> OTHER INFORMATION: 3B (Fig. 8B)
```

-continued

```
<400> SEQUENCE: 71
cguuagcaga aacaaaagga gtt                                           23

<210> SEQ ID NO 72
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: misc_feature
<222> LOCATION: (1)
<223> OTHER INFORMATION: NH2-modified
<220> FEATURE:
<221> NAME/KEY: misc_feature
<222> LOCATION: (23)
<223> OTHER INFORMATION: NH2-modified
<220> FEATURE:
<223> OTHER INFORMATION: 26A (Fig. 9B)

<400> SEQUENCE: 72
cuccuuuugu uucugcuaac gtt                                           23

<210> SEQ ID NO 73
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 24A (Fig. 9B)

<400> SEQUENCE: 73
cuccuuuugu uucugcuaac gtt                                           23

<210> SEQ ID NO 74
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 22A (Fig. 9B)

<400> SEQUENCE: 74
cuccuuuugu uucugcuaac gtt                                           23

<210> SEQ ID NO 75
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: misc_feature
```

<222> LOCATION: (23)
<223> OTHER INFORMATION: NH2-modified
<220> FEATURE:
<223> OTHER INFORMATION: 20A (Fig. 9B)

<400> SEQUENCE: 75 cuccuuugu uucugcuaac gtt                                              23

<210> SEQ ID NO 76
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 30A (Fig. 9B)

<400> SEQUENCE: 76
ttcuccuuuu guuucugcua acg                                             23

<210> SEQ ID NO 77
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<221> NAME/KEY: misc_feature
<222> LOCATION: (1)
<223> OTHER INFORMATION: NH2-modified
<220> FEATURE:
<221> NAME/KEY: misc_feature
<222> LOCATION: (23)
<223> OTHER INFORMATION: NH2-modified
<220> FEATURE:
<223> OTHER INFORMATION: 26B (Fig. 9B)

<400> SEQUENCE: 77
cguuagcaga aacaaaagga gtt                                             23

<210> SEQ ID NO 78
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: 18A (Fig. 9B)

<400> SEQUENCE: 78 cuccuuugu uucugcuaac gtt                                              23

<210> SEQ ID NO 79
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide

```
<220> FEATURE:
<223> OTHER INFORMATION: Description of Artificial Sequence: Synthetic
      RNAi oligonucleotide
<220> FEATURE:
<223> OTHER INFORMATION: 18B (Fig. 9B)

<400> SEQUENCE: 79
cguuagcaga aacaaaagga gtt                                              23

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 28A (Fig. 9B)

<400> SEQUENCE: 80
cuccuuuugu uucugcuaac g                                                21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 29A (Fig. 10C)

<400> SEQUENCE: 81
cuccuuuucu uguqcuaac g                                                 21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 29B (Fig. 10C)

<400> SEQUENCE: 82
cguuagcaca aacaaaagga g                                                21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<221> NAME/KEY: modified_base
<222> LOCATION: (3)..(19)
<223> OTHER INFORMATION: 2'-O-methyl modified RNA
<220> FEATURE:
<223> OTHER INFORMATION: 73A (Fig. 10C)

<400> SEQUENCE: 83
cuccuuuugu uucugcuaac g                                                21

<210> SEQ ID NO 84
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      RNAi oligonucleotide
<220> FEATURE:
<221> NAME/KEY: modified_base
<222> LOCATION: (3)..(19)
<223> OTHER INFORMATION: 2'-O-methyl modified RNA
<220> FEATURE:
<223> OTHER INFORMATION: 73B (Fig. 10C)

<400> SEQUENCE: 84
cguuagcaga aacaaaagga g                                              21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 74A (Fig. 10C)
<220> FEATURE:
<221> NAME/KEY: modified_base
<222> LOCATION: (5)..(17)
<223> OTHER INFORMATION: 2'-O-methyl modified RNA

<400> SEQUENCE: 85
cuccuuuugu uucugcuaac g                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 74B (Fig. 10C)
<220> FEATURE:
<221> NAME/KEY: modified_base
<222> LOCATION: (5)..(17)
<223> OTHER INFORMATION: 2'-O-methyl modified RNA

<400> SEQUENCE: 86
cguuagcaga aacaaaagga g                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 75A (Fig. 10C)
<220> FEATURE:
<221> NAME/KEY: modified_base
<222> LOCATION: (7)..(15)
<223> OTHER INFORMATION: 2'-O-methyl modified RNA

<400> SEQUENCE: 87
cuccuuuugu uucugcuaac g                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
```

```
<220> FEATURE:
<223> OTHER INFORMATION: 75B (Fig. 10C)
<220> FEATURE:
<221> NAME/KEY: modified_base
<222> LOCATION: (7)..(15)
<223> OTHER INFORMATION: 2'-O-methyl modified RNA

<400> SEQUENCE: 88
cguuagcaga aacaaaagga g                                           21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 79A (Fig. 10C)
<220> FEATURE:
<221> NAME/KEY: modified_base
<222> LOCATION: (1)..(21)
<223> OTHER INFORMATION: 2'-O-methyl modified RNA

<400> SEQUENCE: 89
cuccuuuugu uucugcuaac g                                           21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 79B (Fig. 10C, 11C)
<220> FEATURE:
<221> NAME/KEY: modified_base
<222> LOCATION: (1)..(21)
<223> OTHER INFORMATION: 2'-O-methyl modified RNA

<400> SEQUENCE: 90
cguuagcaga aacaaaagga g                                           21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 80A (Fig. 11C)

<400> SEQUENCE: 91
cuccuuuugu uucugcuaac g                                           21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 80B (Fig. 11C)

<400> SEQUENCE: 92
cguuagcaga aacaaaagga g                                           21
```

```
<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 81A (Fig. 11C)
<220> FEATURE:
<221> NAME/KEY: modified_base
<222> LOCATION: (1)..(11)
<223> OTHER INFORMATION: 2'-O-methyl modified RNA

<400> SEQUENCE: 93
cuccuuuugu uucugcuaac g                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 81B (Fig. 11C)
<220> FEATURE:
<221> NAME/KEY: modified_base
<222> LOCATION: (1)..(11)
<223> OTHER INFORMATION: 2'-O-methyl modified RNA

<400> SEQUENCE: 94
cguuagcaga aacaaaagga g                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 82A (Fig. 11C)
<220> FEATURE:
<221> NAME/KEY: modified_base
<222> LOCATION: (11)..(21)
<223> OTHER INFORMATION: 2'-O-methyl modified RNA

<400> SEQUENCE: 95
cuccuuuugu uucugcuaac g                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 82B (Fig. 11C)
<220> FEATURE:
<221> NAME/KEY: modified_base
<222> LOCATION: (11)..(21)
<223> OTHER INFORMATION: 2'-O-methyl modified RNA

<400> SEQUENCE: 96
cguuagcaga aacaaaagga g                                              21

<210> SEQ ID NO 97
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 83A (Fig. 11C)
<220> FEATURE:
<221> NAME/KEY: modified_base
<222> LOCATION: (8)..(13)
<223> OTHER INFORMATION: 2'-O-methyl modified RNA

<400> SEQUENCE: 97
cuccuuuugu uucugcuaac g                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 86A (Fig. 11C)
<220> FEATURE:
<221> NAME/KEY: modified_base
<222> LOCATION: (6)..(10)
<223> OTHER INFORMATION: 2'-O-methyl modified RNA
<220> FEATURE:
<221> NAME/KEY: modified_base
<222> LOCATION: (16)..(21)
<223> OTHER INFORMATION: 2'-O-methyl modified RNA

<400> SEQUENCE: 98
cuccuuuugu uucugcuaac g                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 86B (Fig. 11C)
<220> FEATURE:
<221> NAME/KEY: modified_base
<222> LOCATION: (7)..(11)
<223> OTHER INFORMATION: 2'-O-methyl modified RNA
<220> FEATURE:
<221> NAME/KEY: modified_base
<222> LOCATION: (17)..(21)
<223> OTHER INFORMATION: 2'-O-methyl modified RNA

<400> SEQUENCE: 99
cguuagcaga aacaaaagga g                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 75A (Fig. 11C)
<220> FEATURE:
<221> NAME/KEY: modified_base
<222> LOCATION: (7)..(15)
<223> OTHER INFORMATION: 2'-O-methyl modified RNA

<400> SEQUENCE: 100
```
cuccuuuugu uucugcuaac g                                                    21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 28A (Fig. 12B)

<400> SEQUENCE: 101
cuccuuuugu uucugcuaac g                                                    21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 28B (Fig. 12B)

<400> SEQUENCE: 102
cguuagcaga aacaaaagga g                                                    21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 79A (Fig. 12B)
<220> FEATURE:
<221> NAME/KEY: modified_base
<222> LOCATION: (1)..(21)
<223> OTHER INFORMATION: 2'-O-methyl modified RNA

<400> SEQUENCE: 103
cuccuuuugu uucugcuaac g                                                    21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 79B (Fig. 12B)
<220> FEATURE:
<221> NAME/KEY: modified_base
<222> LOCATION: (1)..(21)
<223> OTHER INFORMATION: 2'-O-methyl modified RNA

<400> SEQUENCE: 104
cguuagcaga aacaaaagga g                                                    21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:

```
<223> OTHER INFORMATION: 81A (Fig. 12B)
<220> FEATURE:
<221> NAME/KEY: modified_base
<222> LOCATION: (1)..(11)
<223> OTHER INFORMATION: 2'-O-methyl modified RNA

<400> SEQUENCE: 105
cuccuuuugu uucugcuaac g                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 81B (Fig. 12B)
<220> FEATURE:
<221> NAME/KEY: modified_base
<222> LOCATION: (1)..(11)
<223> OTHER INFORMATION: 2'-O-methyl modified RNA

<400> SEQUENCE: 106
cguuagcaga aacaaaagga g                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 82A (Fig. 12B)
<220> FEATURE:
<221> NAME/KEY: modified_base
<222> LOCATION: (11)..(21)
<223> OTHER INFORMATION: 2'-O-methyl modified RNA

<400> SEQUENCE: 107
cuccuuuugu uucugcuaac g                                              21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 82B (Fig. 12B)
<220> FEATURE:
<221> NAME/KEY: modified_base
<222> LOCATION: (11)..(21)
<223> OTHER INFORMATION: 2'-O-methyl modified RNA

<400> SEQUENCE: 108
cguuagcaga aacaaaagga g                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 86A (Fig. 12B)
<220> FEATURE:
<221> NAME/KEY: modified_base
```

```
<222> LOCATION: (5)..(10)
<223> OTHER INFORMATION: 2'-O-methyl modified RNA
<220> FEATURE:
<221> NAME/KEY: modified_base
<222> LOCATION: (16)..(21)
<223> OTHER INFORMATION: 2'-O-methyl modified RNA

<400> SEQUENCE: 109
cuccuuuugu uucugcuaac g                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 86B (Fig. 12B)
<220> FEATURE:
<221> NAME/KEY: modified_base
<222> LOCATION: (7)..(11)
<223> OTHER INFORMATION: 2'-O-methyl modified RNA
<220> FEATURE:
<221> NAME/KEY: modified_base
<222> LOCATION: (18)..(21)
<223> OTHER INFORMATION: 2'-O-methyl modified RNA

<400> SEQUENCE: 110
cguuagcaga aacaaaagga g                                              21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94A1 (Fig. 12B)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
```

```
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 111
cuccuuuugu uucugcuaac g                                                   21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94B1 (Fig. 12B)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 112
cguuagcaga aacaaaagga g                                                   21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94A1 (Fig. 12B)
<220> FEATURE:
<221> NAME/KEY: modified_base
<222> LOCATION: (2)
<223> OTHER INFORMATION: 2'-O methyl ribonucleotide
```

```
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 113
cuccuuuugu uucugcuaac g                                        21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94B2 (Fig. 12B)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
```

-continued

```
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 114
cguuagcaga aacaaaagga g                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94A2 (Fig. 12B)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 115
cuccuuuugu uucugcuaac g                                              21
```

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94B1 (Fig. 12B)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 116
cguuagcaga aacaaaagga g                                           21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94A2 (Fig. 12B)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:

<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 117
cuccuuuugu uucugcuaac g                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: 94B2 (Fig. 12B)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:

```
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 118
cguuagcaga aacaaaagga g                                             21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA (Fig. 15A, B)

<400> SEQUENCE: 119
cuccuuuugu uucugcuaac g                                             21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB (Fig. 15A, B)

<400> SEQUENCE: 120
cguuagcaga aacaaaagga g                                             21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENAMM (Fig. 15A)

<400> SEQUENCE: 121
cucauuuucu uugugcucac g                                             21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENBMM (Fig. 15A)

<400> SEQUENCE: 122
cgugagcaca aagaaaauga g                                             21

<210> SEQ ID NO 123
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V1 (Fig. 15A, B)
<220> FEATURE:
<221> NAME/KEY: modified_base
<222> LOCATION: (1)..(21)
<223> OTHER INFORMATION: 2'-O methyl ribonucleotide

<400> SEQUENCE: 123
cuccuuuugu uucugcuaac g                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V1 (Fig. 15A, B)
<220> FEATURE:
<221> NAME/KEY: modified_base
<222> LOCATION: (1)..(21)
<223> OTHER INFORMATION: 2'-O methyl ribonucleotide

<400> SEQUENCE: 124
cguuagcaga aacaaaagga g                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V2 (Fig. 15A)
<220> FEATURE:
<221> NAME/KEY: modified_base
<222> LOCATION: (3)..(19)
<223> OTHER INFORMATION: 2'-O methyl ribonucleotide

<400> SEQUENCE: 125
cuccuuuugu uucugcuaac g                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V2 (Fig. 15A)
<220> FEATURE:
<221> NAME/KEY: modified_base
<222> LOCATION: (3)..(19)
<223> OTHER INFORMATION: 2'-O methyl ribonucleotide

<400> SEQUENCE: 126
cguuagcaga aacaaaagga g                                              21

<210> SEQ ID NO 127
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      RNAi oligonucleotide
<220> FEATURE:
<223> OTHER INFORMATION: PTENA V3 (Fig. 15A)
<220> FEATURE:
<221> NAME/KEY: modified_base
<222> LOCATION: (5)..(17)
<223> OTHER INFORMATION: 2'-O methyl ribonucleotide

<400> SEQUENCE: 127
cuccuuuugu uucugcuaac g                                           21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V3 (Fig. 15A)
<220> FEATURE:
<221> NAME/KEY: modified_base
<222> LOCATION: (5)..(17)
<223> OTHER INFORMATION: 2'-O methyl ribonucleotide

<400> SEQUENCE: 128
cguuagcaga aacaaaagga g                                           21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V4 (Fig. 15A)
<220> FEATURE:
<221> NAME/KEY: modified_base
<222> LOCATION: (7)..(15)
<223> OTHER INFORMATION: 2'-O methyl ribonucleotide

<400> SEQUENCE: 129
cuccuuuugu uucugcuaac g                                           21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V4 (Fig. 15A)
<220> FEATURE:
<221> NAME/KEY: modified_base
<222> LOCATION: (7)..(15)
<223> OTHER INFORMATION: 2'-O methyl ribonucleotide

<400> SEQUENCE: 130
cguuagcaga aacaaaagga g                                           21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
```

```
<223> OTHER INFORMATION: PTENA V5 (Fig. 15A)

<400> SEQUENCE: 131
cuccuuuugu uucugcuaac g                                      21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V5 (Fig. 15A)
<220> FEATURE:
<221> NAME/KEY: modified_base
<222> LOCATION: (1)..(21)
<223> OTHER INFORMATION: 2'-O methyl ribonucleotide

<400> SEQUENCE: 132
cguuagcaga aacaaaagga g                                      21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V6 (Fig. 15A)
<220> FEATURE:
<221> NAME/KEY: modified_base
<222> LOCATION: (1)..(21)
<223> OTHER INFORMATION: 2'-O methyl ribonucleotide

<400> SEQUENCE: 133
cuccuuuugu uucugcuaac g                                      21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V6 (Fig. 15A)

<400> SEQUENCE: 134
cguuagcaga aacaaaagga g                                      21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V7 (Fig. 15A, B)
<220> FEATURE:
<221> NAME/KEY: modified_base
<222> LOCATION: (1)..(11)
<223> OTHER INFORMATION: 2'-O methyl ribonucleotide

<400> SEQUENCE: 135
cuccuuuugu uucugcuaac g                                      21
```

```
<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V7 (Fig. 15A, B)
<220> FEATURE:
<221> NAME/KEY: modified_base
<222> LOCATION: (1)..(11)
<223> OTHER INFORMATION: 2'-O methyl ribonucleotide

<400> SEQUENCE: 136
cguuagcaga aacaaaagga g                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V8 (Fig. 15A, B)
<220> FEATURE:
<221> NAME/KEY: modified_base
<222> LOCATION: (11)..(21)
<223> OTHER INFORMATION: 2'-O methyl ribonucleotide

<400> SEQUENCE: 137
cuccuuuugu uucugcuaac g                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V8 (Fig. 15A, B)
<220> FEATURE:
<221> NAME/KEY: modified_base
<222> LOCATION: (11)..(21)
<223> OTHER INFORMATION: 2'-O methyl ribonucleotide

<400> SEQUENCE: 138
cguuagcaga aacaaaagga g                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V9 (Fig. 15A)
<220> FEATURE:
<221> NAME/KEY: modified_base
<222> LOCATION: (8)..(13)
<223> OTHER INFORMATION: 2'-O methyl ribonucleotide

<400> SEQUENCE: 139
cuccuuuugu uucugcuaac g                                              21

<210> SEQ ID NO 140
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V9 (Fig. 15A)
<220> FEATURE:
<221> NAME/KEY: modified_base
<222> LOCATION: (1)..(21)
<223> OTHER INFORMATION: 2'-O methyl ribonucleotide

<400> SEQUENCE: 140
cguuagcaga aacaaaagga g                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V10 (Fig. 15A, B)
<220> FEATURE:
<221> NAME/KEY: modified_base
<222> LOCATION: (6)..(10)
<223> OTHER INFORMATION: 2'-O methyl ribonucleotide
<220> FEATURE:
<221> NAME/KEY: modified_base
<222> LOCATION: (16)..(21)
<223> OTHER INFORMATION: 2'-O methyl ribonucleotide

<400> SEQUENCE: 141
cuccuuuugu uucugcuaac g                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V10 (Fig. 15A, B)
<220> FEATURE:
<221> NAME/KEY: modified_base
<222> LOCATION: (7)..(12)
<223> OTHER INFORMATION: 2'-O methyl ribonucleotide
<220> FEATURE:
<221> NAME/KEY: modified_base
<222> LOCATION: (17)..(21)
<223> OTHER INFORMATION: 2'-O methyl ribonucleotide

<400> SEQUENCE: 142
cguuagcaga aacaaaagga g                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V11 (Fig. 15A)
<220> FEATURE:
<221> NAME/KEY: modified_base
<222> LOCATION: (7)..(15)
<223> OTHER INFORMATION: 2'-O methyl ribonucleotide

<400> SEQUENCE: 143
cuccuuuugu uucugcuaac g                                              21
```

```
<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V11 (Fig. 15A)
<220> FEATURE:
<221> NAME/KEY: modified_base
<222> LOCATION: (1)..(21)
<223> OTHER INFORMATION: 2'-O methyl ribonucleotide

<400> SEQUENCE: 144
cguuagcaga aacaaaagga g                                            21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V12 (Fig. 15A, B)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 145
cuccuuuugu uucugcuaac g                                            21
```

```
<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V12 (Fig. 15A, B)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 146
cguuagcaga aacaaaagga g                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V13 (Fig. 15B)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
```

```
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 147
cuccuuuugu uucugcuaac g                                        21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V13 (Fig. 15B)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
```

```
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 148
cguuagcaga aacaaaagga g                                              21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V14 (Fig. 15B)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 149
cuccuuuugu uucugcuaac g                                              21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V14 (Fig. 15B)
<220> FEATURE:
<221> NAME/KEY: modified_base
<222> LOCATION: (1)
```

```
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 150
cguuagcaga aacaaaagga g                                               21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENA V15 (Fig. 15B)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
```

```
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 151
cuccuuuugu uucugcuaac g                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: PTENB V15 (Fig. 15B)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 152
```
cguuagcaga aacaaaagga g                                             21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1A V1 (Fig. 16A)

<400> SEQUENCE: 153
ucuugaugua cuccccucgt t                                             21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide
<220> FEATURE:
<223> OTHER INFORMATION: Akt1B V1 (Fig. 16A)

<400> SEQUENCE: 154
cgaggggagu acaucaagat t                                             21

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1A V2 (Fig. 16A)

<400> SEQUENCE: 155
ucuugaugua cuccccucg                                                19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1B V2 (Fig. 16A)

<400> SEQUENCE: 156
cgaggggagu acaucaaga                                                19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1A V3 (Fig. 16A)
<220> FEATURE:

```
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 157
ucuugaugua cuccccucg                                           19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1B V3 (Fig. 16A)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
```

```
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 158 cgagggagu acaucaaga                                                   19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: AKt1A V4 (Fig. 16A)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 159
ucuugaugua cuccccucg                                                  19

<210> SEQ ID NO 160
<211> LENGTH: 19
<212> TYPE: RNA
```

<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1B V4 (Fig. 16A)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 160
cgaggggagu acaucaaga                                               19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1A V5 (Fig. 16A)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base

```
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 161
ucuugaugua cuccccucg                                                  19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1B V5 (Fig. 16A)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
```

```
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 162
cgaggggagu acaucaaga                                                    19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: Akt1A V6 (Fig. 16A)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 163
ucuugaugua cuccccucg                                                    19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
```

```
<223> OTHER INFORMATION: Akt1B V6 (Fig. 16A)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 164 cgagggagu acaucaaga                                                    19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V2 (Fig. 16C)

<400> SEQUENCE: 165
aauuccagug guucauucc                                                   19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V2 (complementary sequence, Fig. 16C)

<400> SEQUENCE: 166
ggaaugaacc acuggaauu                                                   19
```

```
<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V3 (Fig. 16C)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 167
aauuccagug guucauucc                                                19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V3 (complementary sequence, Fig. 16C)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
```

```
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 168
ggaaugaacc acuggaauu                                               19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V4 (Fig. 16C)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
```

```
<221> NAME/KEY: modified_base
<222> LOCATION: (20)
<223> OTHER INFORMATION: 2'-O methyl ribonucleotide

<400> SEQUENCE: 169
aauuccagug guucauucc                                                    19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V4 (complementary sequence, Fig. 16C)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 170
ggaaugaacc acuggaauu                                                    19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V5 (Fig. 16C)
<220> FEATURE:
<221> NAME/KEY: modified_base
```

```
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 171
aauuccagug guucauucc                                              19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V5 (complementary sequence, Fig. 16C)
<220> FEATURE:
<221> NAME/KEY: modified_base
<222> LOCATION: (2)
<223> OTHER INFORMATION: 2'-O methyl ribonucleotide
<220> FEATURE:
<221> NAME/KEY: modified_base
<222> LOCATION: (4)
<223> OTHER INFORMATION: 2'-O methyl ribonucleotide
<220> FEATURE:
<221> NAME/KEY: modified_base
<222> LOCATION: (6)
<223> OTHER INFORMATION: 2'-O methyl ribonucleotide
<220> FEATURE:
<221> NAME/KEY: modified_base
<222> LOCATION: (8)
<223> OTHER INFORMATION: 2'-O methyl ribonucleotide
<220> FEATURE:
<221> NAME/KEY: modified_base
<222> LOCATION: (10)
<223> OTHER INFORMATION: 2'-O methyl ribonucleotide
<220> FEATURE:
<221> NAME/KEY: modified_base
```

-continued

```
<222> LOCATION: (12)
<223> OTHER INFORMATION: 2'-O methyl ribonucleotide
<220> FEATURE:
<221> NAME/KEY: modified_base
<222> LOCATION: (14)
<223> OTHER INFORMATION: 2'-O methyl ribonucleotide
<220> FEATURE:
<221> NAME/KEY: modified_base
<222> LOCATION: (16)
<223> OTHER INFORMATION: 2'-O methyl ribonucleotide
<220> FEATURE:
<221> NAME/KEY: modified_base
<222> LOCATION: (18)
<223> OTHER INFORMATION: 2'-O methyl ribonucleotide
<220> FEATURE:
<221> NAME/KEY: modified_base
<222> LOCATION: (20)
<223> OTHER INFORMATION: 2'-O methyl ribonucleotide

<400> SEQUENCE: 172
ggaaugaacc acuggaauu                                                       19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V6 (Fig. 16C)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 173
```
aauuccagug guucauucc                                              19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      RNAi oligonucleotide
<220> FEATURE:
<223> OTHER INFORMATION: P110b V6 (complementary sequence, Fig. 16C)
<220> FEATURE:
<221> NAME/KEY: modified_base
<222> LOCATION: (1)
<223> OTHER INFORMATION: 2'-O methyl ribonucleotide
<220> FEATURE:
<221> NAME/KEY: modified_base
<222> LOCATION: (3)
<223> OTHER INFORMATION: 2'-O methyl ribonucleotide
<220> FEATURE:
<221> NAME/KEY: modified_base
<222> LOCATION: (5)
<223> OTHER INFORMATION: 2'-O methyl ribonucleotide
<220> FEATURE:
<221> NAME/KEY: modified_base
<222> LOCATION: (7)
<223> OTHER INFORMATION: 2'-O methyl ribonucleotide
<220> FEATURE:
<221> NAME/KEY: modified_base
<222> LOCATION: (9)
<223> OTHER INFORMATION: 2'-O methyl ribonucleotide
<220> FEATURE:
<221> NAME/KEY: modified_base
<222> LOCATION: (11)
<223> OTHER INFORMATION: 2'-O methyl ribonucleotide
<220> FEATURE:
<221> NAME/KEY: modified_base
<222> LOCATION: (13)
<223> OTHER INFORMATION: 2'-O methyl ribonucleotide
<220> FEATURE:
<221> NAME/KEY: modified_base
<222> LOCATION: (15)
<223> OTHER INFORMATION: 2'-O methyl ribonucleotide
<220> FEATURE:
<221> NAME/KEY: modified_base
<222> LOCATION: (17)
<223> OTHER INFORMATION: 2'-O methyl ribonucleotide
<220> FEATURE:
<221> NAME/KEY: modified_base
<222> LOCATION: (19)
<223> OTHER INFORMATION: 2'-O methyl ribonucleotide
<220> FEATURE:
<221> NAME/KEY: modified_base
<222> LOCATION: (21)
<223> OTHER INFORMATION: 2'-O methyl ribonucleotide

<400> SEQUENCE: 174
ggaaugaacc acuggaauu                                              19

<210> SEQ ID NO 175
<211> LENGTH: 12
<212> TYPE: DNA
<213> ORGANISM: Artificial Sequence
<220> FEATURE:
<223> OTHER INFORMATION: Description of Artificial Sequence: Synthetic
      pA-loop

<400> SEQUENCE: 175
aaaaaaaaaa aa                                                     12

<210> SEQ ID NO 176
<211> LENGTH: 22
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 176
caccgccaaa tttaactgca ga                                              22

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
aagggtttga taagttctag ctgt                                            24

<210> SEQ ID NO 178
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
tgcacagtat cctttttgaag accataaccc a                                   31

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gtttgagacc ttcaacaccc ca                                              22

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gaccagaggc atacagggac a                                               21

<210> SEQ ID NO 181
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
ccatgtacgt agccatccag gctgtg                                          26

<210> SEQ ID NO 182
<211> LENGTH: 23
<212> TYPE: DNA
<213> ORGANISM: Artificial Sequence
```

```
<220> FEATURE:
<223> OTHER INFORMATION: Description of Combined DNA/RNA Molecule:
      Synthetic RNAi oligonucleotide
<220> FEATURE:
<223> OTHER INFORMATION: Description of Artificial Sequence: Synthetic
      RNAi oligonucleotide

<400> SEQUENCE: 182
ucuccuuttg tttctgcuaa cga                                                  23
```

INTERFERING RNA MOLECULES

CROSS REFERENCE TO RELATED APPLICATIONS

This application is a continuation of U.S. patent application, Ser. No. 14/977,710, filed Dec. 22, 2015, which is a continuation of U.S. patent application Ser. No. 14/578,636, filed on Dec. 22, 2014, now U.S. Pat. No. 9,222,092, issued Dec. 29, 2015, which is a continuation of U.S. patent application Ser. No. 13/692,178, filed on Dec. 3, 2012, now U.S. Pat. No. 8,933,215, issued Jan. 13, 2015, which is a continuation of U.S. patent application Ser. No. 12/986,389, filed on Jan. 7, 2011, now U.S. Pat. No. 8,324,370, issued Dec. 4, 2012, which is a continuation of U.S. patent application Ser. No. 12/200,296, filed on Aug. 28, 2008, now U.S. Pat. No. 7,893,245, issued Feb. 22, 2011, which is a continuation of U.S. patent application Ser. No. 10/633,630, filed on Aug. 5, 2003, now U.S. Pat. No. 7,452,987, issued Nov. 18, 2008, which claims the benefit of U.S. Provisional Application No. 60/402,541, filed Aug. 12, 2002, European Application No. 02017601.2, filed Aug. 5, 2002, and European Application No. 03008383.6, filed Apr. 10, 2003. Each of these applications is incorporated herein by reference in their entirety, including all figures, tables and amino acid or nucleic acid sequences.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 680132000106seqlist.txt, date recorded: May 1, 2017, size: 85 KB).

FIELD OF THE INVENTION

The invention provides novel forms of interfering ribonucleic acid molecules having a double-stranded structure. The first strand comprises a first stretch of contiguous nucleotides that is at least partially complementary to a target nucleic acid, and the second strand comprises a second stretch of contiguous nucleotides that is at least partially identical to a target nucleic acid. Methods for using these molecules, for example for inhibiting expression of a target gene, and pharmaceutical compositions, cells and organisms containing these molecules also are provided.

BACKGROUND OF THE INVENTION

RNA-mediated interference (RNAi) is a post-transcriptional gene silencing mechanism initiated by double stranded RNA (dsRNA) homologous in sequence to the silenced gene (Fire (1999), Trends Genet 15, 358-63, Tuschl et al. (1999), Genes Dev 13, 3191-7, Waterhouse, et al. (2001), Nature 411, 834-42, Elbashir, et al. (2001), Nature 411, 494-8, for review see Sharp (2001), Genes Dev 15, 485-90, Barstead (2001), Curr Opin Chem Biol 5, 63-6). RNAi has been used extensively to determine gene function in a number of organisms, including plants (Baulcombe (1999), Curr Opin Plant Biol 2, 109-13), nematodes (Montgomery, et al. (1998), Proc Natl Acad Sci USA 95, 15502-7), *Drosophila* (Kennerdell, et al. (1998), Cell 95, 1017-26, Kennerdell, et al. (2000), Nat Biotechnol 18, 896-8). In the nematode *C. elegans* about one third of the genome has already been subjected to functional analysis by RNAi (Kim (2001), Curr. Biol 11, R85-7, Maeda, et al. (2001), Curr Biol 11, 171-6).

Until recently RNAi in mammalian cells was not generally applicable, with the exception of early mouse development (Wianny, et al. (2000), Nat Cell Biol 2, 70-5). The discovery that transfection of duplexes of 21-nt into mammalian cells interfered with gene expression and did not induce a sequence independent interferon-driven anti-viral response usually obtained with long dsRNA led to new potential application in differentiated mammalian cells (Elbashir et al. (2001), Nature 411, 494-8). Interestingly these small interfering RNAs (siRNAs) resemble the processing products from long dsRNAs suggesting a potential bypassing mechanism in differentiated mammalian cells. The Dicer complex, a member of the RNAse III family, necessary for the initial dsRNA processing has been identified (Bernstein, et al. (2001), Nature 409, 363-6, Billy, et al. (2001), Proc Natl Acad Sci USA 98, 14428-33). One of the problems previously encountered when using unmodified ribooligonucleotides was the rapid degradation in cells or even in the serum-containing medium (Wickstrom (1986), J Biochem Biophys Methods 13, 97-102, Cazenave, et al. (1987). Nucleic Acids Res 15, 10507-21). It will depend on the particular gene function and assay systems used whether the respective knock down induced by transfected siRNA will be maintained long enough to achieve a phenotypic change.

It is apparent, therefore, that synthetic interfering RNA molecules that are both stable and active in a biochemical environment such as a living cell are greatly to be desired.

SUMMARY OF THE INVENTION

It is therefore an object of the present invention to provide compositions and methods using interfering RNA molecules having enhanced stability.

In accomplishing this object, there has been provided, in accordance with a first aspect of the present invention, a ribonucleic acid comprising a double stranded structure whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides whereby said second stretch is at least partially identical to a target nucleic acid, and whereby the double stranded structure is blunt ended.

In accordance with a second aspect of the present invention there has been provided a ribonucleic acid comprising a double stranded structure whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides, whereby said second stretch is at least partially identical to a target nucleic acid, whereby the first stretch and/or the second stretch have a length of 18 or 19 nucleotides.

In an embodiment of the ribonucleic acid according to the first aspect of the invention the first stretch and/or the second stretch have a length of 18 or 19 nucleotides.

In a further embodiment of the ribonucleic acid according to the first aspect of the invention the double stranded structure is blunt ended on both sides of the double strand.

In an alternative embodiment of the ribonucleic acid according to the first aspect of the invention the double stranded structure is blunt ended on the double stranded structure which is defined by the 5'-end of the first strand and the 3'-end of the second strand.

In a further alternative embodiment of the ribonucleic acid according to the first and the second aspect of the invention the double stranded structure is blunt ended on the double stranded structure which is defined by the 3'-end of the first strand and the 5'-end of the second strand.

In accordance with a third aspect of the present invention there has been provided a ribonucleic acid comprising a double stranded structure whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides and whereby said second stretch is at least partially identical to a target nucleic acid, and whereby at least one of the two strands has an overhang of at least one nucleotide at the 5'-end.

In an embodiment of the ribonucleic acid according to the third aspect of the present invention the overhang consists of at least one nucleotide which is selected from the group comprising ribonucleotides and deoxyribonucleotides In a more preferred embodiment of the ribonucleic acid according to the third aspect of the present invention the nucleotide has a modification whereby said modification is preferably selected from the group comprising nucleotides being an inverted abasic and nucleotides having an NH-modification at the 2'-position.

In a preferred embodiment of the ribonucleic acid according to the third aspect of the present invention at least one of the strands has an overhang of at least one nucleotide at the 3'-end consisting of ribonucleotide or deoxyribonucleotide.

In another preferred embodiment of the ribonucleic acid according to the third aspect of the present invention the first stretch and/or the second stretch have a length of 18 or 19 nucleotides.

In an embodiment of the ribonucleic acid according to any aspect of the present invention the double-stranded structure has a length of 17 to 21 nucleotides, preferably 18 to 19 nucleotides.

In an embodiment of the ribonucleic acid according to the third aspect of the present invention the overhang at the 5'-end is on the second strand.

In a preferred embodiment of the ribonucleic acid according to the third aspect of the present invention the first strand comprises also an overhang, preferably at the 5'-end.

In an embodiment of the ribonucleic acid according to the third aspect of the present invention the 3'-end of the first strand comprises an overhang.

In an alternative embodiment of the ribonucleic acid according to the third aspect of the present invention the overhang at the 5'-end is on the first strand.

In a preferred embodiment thereof the second strand also comprises an overhang, preferably at the 5'-end.

In an embodiment of the ribonucleic acid according to the third aspect of the present invention the 3'-end of the first strand comprises an overhang.

In an embodiment of the ribonucleic acid according to any aspect of the present invention at least one nucleotide of the ribonucleic acid has a modification at the 2'-position and the modification is preferably selected from the group comprising amino, fluoro, methoxy, alkoxy and alkyl.

In accordance with a fourth aspect of the present invention there has been provided a ribonucleic acid comprising a double stranded structure, whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides and whereby said second stretch is at least partially identical to a target nucleic acid, whereby said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides.

In an embodiment of the ribonucleic acid according to the fourth aspect of the present invention the ribonucleic acid is the ribonucleic acid according to the first, second or third aspect of the present invention.

In a further embodiment of the ribonucleic acid according to the fourth aspect of the present invention said first strand and/or said second strand comprise said plurality of modified nucleotides.

In another embodiment of the ribonucleic acid according to the fourth aspect of the present invention said first strand comprises said plurality of groups of modified nucleotides.

In yet another embodiment of the ribonucleic acid according to the fourth aspect of the present invention said second strand comprises said plurality of groups of modified nucleotides.

In a preferred embodiment of the ribonucleic acid according to the fourth aspect of the present invention the group of modified nucleotides and/or the group of flanking nucleotides comprises a number of nucleotides whereby the number is selected from the group comprising one nucleotide to 10 nucleotides.

In another embodiment of the ribonucleic acid according to the fourth aspect of the present invention the pattern of modified nucleotides of said first strand is the same as the pattern of modified nucleotides of said second strand.

In a preferred embodiment of the ribonucleic acid according to the fourth aspect of the present invention the pattern of said first strand aligns with the pattern of said second strand.

In an alternative embodiment of the ribonucleic acid according to the fourth aspect of the present invention the pattern of said first strand is shifted by one or more nucleotides relative to the pattern of the second strand.

In an embodiment of the ribonucleic acid according to the fourth aspect of the present invention the modification is selected from the group comprising amino, fluoro, methoxy, alkoxy and alkyl.

In another embodiment of the ribonucleic acid according to the fourth aspect of the present invention the double stranded structure is blunt ended.

In a preferred embodiment of the ribonucleic acid according to the fourth aspect of the present invention the double stranded structure is blunt ended on both sides.

In another embodiment of the ribonucleic acid according to the fourth aspect of the present invention the double stranded structure is blunt ended on the double stranded structure's side which is defined by the 5'-end of the first strand and the 3'-end of the second strand.

In still another embodiment of the ribonucleic acid according to the fourth aspect of the present invention the double stranded structure is blunt ended on the double stranded structure's side which is defined at the 3'-end of the first strand and the 5'-end of the second strand.

In another embodiment of the ribonucleic acid according to the fourth aspect of the present invention at least one of the two strands has an overhang of at least one nucleotide at the 5'-end.

In a preferred embodiment of the ribonucleic acid according to the fourth aspect of the present invention the overhang consists of at least one deoxyribonucleotides.

In a further embodiment of the ribonucleic acid according to the fourth aspect of the present invention at least one of the strands has an overhang of at least one nucleotide at the 3'-end.

In an embodiment of the ribonucleic acid according to any of the aspects of the present invention the length of the double-stranded structure has a length from about 17 to 21 and more preferably 18 or 19 bases.

In another embodiment of the ribonucleic acid according to any of the aspects of the present invention the length of said first strand and/or the length of said second strand is independently from each other selected from the group comprising the ranges of from about 15 to about 23 bases, 17 to 21 bases and 18 or 19 bases.

In a preferred embodiment of the ribonucleic acid according to any of the aspects of the present invention the complementarity between said first strand and the target nucleic acid is perfect.

In an embodiment of the ribonucleic acid according to any of the aspects of the present invention the duplex formed between the first strand and the target nucleic acid comprises at least 15 nucleotides wherein there is one mismatch or two mismatches between said first strand and the target nucleic acid forming said double-stranded structure.

In an embodiment of the ribonucleic acid according to any of the aspects of the present invention, wherein both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide; with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides.

In a preferred embodiment of the ribonucleic acid according to the fourth aspect, wherein each group of modified nucleotides consists of a single nucleotide and/or each flanking group of nucleotides consists of a single nucleotide.

In a further embodiment of the ribonucleic acid according to the fourth aspect, wherein on the first strand the nucleotide forming the flanking group of nucleotides is an unmodified nucleotide which is arranged in a 3' direction relative to the nucleotide forming the group of modified nucleotides, and wherein on the second strand the nucleotide forming the group of modified nucleotides is a modified nucleotide which is arranged in 5' direction relative to the nucleotide forming the flanking group of nucleotides.

In another embodiment of the ribonucleic acid according to the fourth aspect, wherein the first strand comprises eight to twelve, preferably nine to eleven, groups of modified nucleotides, and wherein the second strand comprises seven to eleven, preferably eight to ten, groups of modified nucleotides.

In a preferred embodiment of the ribonucleic acid according to any of the aspects of the present invention the target gene is selected from the group comprising structural genes, housekeeping genes, transcription factors, motility factors, cell cycle factors, cell cycle inhibitors, enzymes, growth factors, cytokines and tumor suppressors.

In a further embodiment of the ribonucleic acid according to any of the aspects of the present invention the first strand and the second strand are linked by a loop structure.

In a preferred embodiment of the ribonucleic acid according to any of the aspects of the present invention the loop structure is comprised of a non-nucleic acid polymer.

In a preferred embodiment thereof the non-nucleic acid polymer is polyethylene glycol.

In an alternative embodiment thereof the loop structure is comprised of a nucleic acid.

In an embodiment of the ribonucleic acid according to any of the aspects of the present invention the 5'-terminus of the first strand is linked to the 3'-terminus of the second strand.

In a further embodiment of the ribonucleic acid according to any of the aspects of the present invention the 3'-end of the first strand is linked to the 5'-terminus of the second strand.

In accordance with a fifth aspect of the present invention there have been provided methods of using a ribonucleic acid according to any of the aspects of the present invention for target validation.

In accordance with a sixth aspect of the present invention there have been provided medicaments and pharmaceutical compositions containing a ribonucleic acid according to any of the aspects of the present invention, and methods of making such medicaments and compositions.

In a preferred embodiment of the use according to the sixth aspect of the present invention methods are provided for the treatment of a disease or of a condition which is selected from the group comprising glioblastoma, prostate cancer, breast cancer, lung cancer, liver cancer, colon cancer, pancreatic cancer and leukaemia, diabetes, obesity, cardiovascular diseases, and metabolic diseases.

In accordance with a seventh aspect of the present invention there has been provided a cell, for example a knockdown cell, containing a ribonucleic acid according to any of the aspects of the present invention.

In accordance with an eighth aspect of the present invention there has been provided an organism, for example a knockdown organism, containing a ribonucleic acid according to any of the aspects of the present invention.

In accordance with a ninth aspect of the present invention there has been provided a composition containing a ribonucleic acid according to any of the aspects of the present invention.

In accordance with a tenth aspect of the present invention there has been provided a pharmaceutical composition containing a ribonucleic acid according to any of the aspects of the present invention, and a pharmaceutically acceptable carrier.

In accordance with an eleventh aspect of the present invention there has been provided a method for inhibiting the expression of a target gene in a cell or derivative thereof comprising introducing a ribonucleic acid according to any of the aspects of the present invention into a cell in an amount sufficient to inhibit expression of the target gene, wherein the target gene is the target gene of a ribonucleic acid according to any of the aspects of the present invention.

BRIEF DESCRIPTION OF THE DRAWINGS

FIG. 2 illustrates some embodiments of the ribonucleic acid molecules of the present invention with patterns of modified and unmodified groups of nucleotides which are also referred to herein as a pattern of modification. The modified groups of nucleotides are also referred to herein as a group of modified nucleotides. The unmodified nucleotides or unmodified groups of nucleotides referred to as flanking group(s) of nucleotides herein, as used herein may also have one or several of the modification(s) as disclosed herein which, however, is/are different from the modification of the nucleotides forming the group(s) of modified nucleotides. In FIG. 2A the modified and unmodified groups of nucleotides, i.e. the groups of modified nucleotides and the flanking groups of nucleotides on both the first stretch and the second stretch are located on corresponding parts of the stretches and are thus aligned to each other (groups of modified nucleotides on the first strand aligned with groups of modified nucleotides on the second strand and flanking groups of nucleotides on the first strand aligned with flanking group of nucleotides on the second strand), whereas in FIG. 2B the pattern realised on the first strand is also realised on the second strand, however, with a phase shift such that the modified group of nucleotides of the first stretch is base pairing with an unmodified group of nucleotides of the second stretch and vice versa so that a group of modified nucleotides on the first strand aligns with a flanking group of nucleotides on the second strand. In FIG. 2C a further possibility of arranging the modified and unmodified groups of nucleotides is realised. It is also within the present invention that the pattern of the first stretch is independent from the pattern of the second stretch and that both patterns partially overlap in terms of relative position to each other in the double-stranded structure defined by base pairing. In a further embodiment the extent of this overlapping can vary over the length of the stretch(es) and strand(s), respectively.

FIGS. 3A-3C show the result of a knockdown experiment using RNAi molecules with different end protection groups. More particularly FIG. 3A shows that the various forms of end protected RNAi molecules are functional on the knockdown of PTEN mRNA.

FIG. 3B (SEQ ID NOs: 1-8, respectively in order of appearance) shows the sequence of the different RNAi molecules used in the experiment the result of which is depicted in FIG. 3A. FIG. 3C shows the result of an immunoblot analysis of PTEN protein after treatment with modified RNAi molecules in comparison to PTEN specific antisense constructs.

FIGS. 4A-4B show that the 3' overhang of RNAi molecules is not important for RNA interference. More particularly, FIG. 4A shows a dose response curve of different RNAi molecules and FIG. 4B (SEQ ID NOs: 9-20, respectively in order of appearance) shows the sequence of the RNAi molecules used in the experiment the result of which is shown in FIG. 4A.

FIGS. 5A-5B show that duplex length of the RNAi molecules has to be at least 18-19 nucleotides. More particularly, FIG. 5B (SEQ ID NOs: 21-28, respectively in order of appearance) shows the sequence of the PTEN specific RNAi molecules used in the experiment the result of which is depicted in FIG. 5A as dose response curve.

FIGS. 6A-6B show that four terminal mismatched nucleotides in RNAi molecules with a length of 19 nucleotides are still functional in mediating Akt1 knockdown. More particularly, FIG. 6B (SEQ ID) NOs: 29-36, respectively in order of appearance) shows the sequence of the RNAi molecules used in the experiment the result of which is depicted in FIG. 6A.

FIGS. 7A-7C show further results on duplex length requirements and tolerance for mutation in siRNAs. More particularly, FIG. 7A (SEQ ID NOs: 37-52, respectively in order of appearance) shows the various constructs used (left panel) and the respective impact on inhibition of Akt1 mRNA expression in HeLa cells relative to the expression of p110α used in the indicated amounts of siRNA molecules (right panel). The nucleotide changes in the mismatch siRNA molecules are indicated by arrows, the 3' deoxyribonucleotides, if any, are indicated in capital letters. FIG. 7B (SEQ ID NOs: 53-62, respectively in order of appearance) shows the various PTEN specific siRNAs (left panel), the inhibition of PTEN mRNA expression in HeLA cells expressed as ratio PTEN/p110α, at various amounts of siRNA (middle panel) and FIG. 7C a Western Blot analysis depicting the inhibition of PTEN protein expression using PTEN specific siRNA (30 nM) and respective mismatch siRNA after 48 and 96 hours, respectively, with p100α being used as loading control.

FIGS. 8A-8B show the result of studies on the stability in serum conferred to RNAi molecules by 2'-O-methylation and that end modifications have no beneficial effects on RNAi stability. More particularly, FIG. 8A shows the result of a gel electrophoresis of the various RNAi molecules depicted in FIG. 8B (SEQ ID NOs: 9, 10, 63-68, 13, 14, 17 and 69-71, respectively in order of appearance) being subject to incubation with fetal calf serum.

FIGS. 9A-9C show that an amino end modification results in loss of activity. FIG. 9B (SEQ ID NOs: 72, 77, 73, 77, 74, 77, 75, 77, 78, 77, 76, 77, 80, 77, 78, and 79, respectively in order of appearance) shows the particular RNAi molecules used in the experiments the result of which is shown in FIG. 9A expressed as PTEN/p110α expression level ratio. FIG. 9C shows the design principles which may be deduced from the results depicted in FIG. 9A. As used in FIG. 9C the term functional means functionally active in the particular assay system as described in the example and "not functional" means not functionally active in said system.

FIGS. 10A-10C show that 2'-O-Alkyl (methyl) modifications stabilize RNAi molecules but also result in reduction of their activity. More particularly, FIG. 10C shows the sequence of the RNAi molecules used in the experiment the result of which is depicted as a dose response curve in FIG. 10A. FIG. 10B shows the result of a gel electrophoresis of the various RNAi molecules depicted in FIG. 10C (SEQ ID NOs: 13, 14, 81-90, 80, 90, 89, 14, 87 and 90, respectively in order of appearance) being subject to a two hour incubation in fetal calf serum.

FIGS. 11A-11C show the result of an experiment on the efficacy of RNAi molecules with blocks of 2'-O-methyl modifications with FIG. 11A graphically depicting the results of said experiments as a dose response curve and with FIG. 11C showing the sequences of the particular RNAi molecules used in said experiments. FIG. 11B shows the result of a gel electrophoresis of the various RNAi molecules depicted in FIG. 11C (SEQ ID NOs: 91-97, 90, 98-100 and 90, respectively in order of appearance) being subject to a two hour incubation in fetal calf serum.

FIGS. 12A-1.2D show that alternating 2'-O-methyl modification result in activity of the modified RNAi molecules compared to unmodified forms. More particularly, FIG. 12B (SEQ ID NOs. 101-118, respectively in order of appearance) shows the sequence of the RNAi molecules used in this experiment the result of which is depicted in FIG. 12A. FIG. 12C shows the stability of said RNAi molecules following incubation in serum for two hours, whereas

FIGS. 15A-15D show that siRNA molecules with distinct 2'-O-methyl ribonucleotides modifications show increased stability in serum and mediate protein knock-down in HeLa cells. More particularly, FIG. 15A (SEQ ID NOs: 119-146, respectively in order of appearance) indicates the various siRNA molecule constructs used (left panel), whereby 2'-O-methyl ribonucleotides modifications are underlined and indicated by bold letters in the sequence. Inhibition of PTEN mRNA expression in HeLa cells transfected with the indicated amounts of modified siRNA molecules is expressed as ratio PTEN/p110α and indicated on the right panel. FIG. 15B (SEQ ID NOs. 119, 120, 123, 124, 135-138, 141, 142, 147-152, 145 and 146, respectively in order of appearance) shows on the left panel the various siRNA constructs used and on the right panel a PAA gel electrophoresis of modified and unmodified siRNA molecules after incubation in serum; the various constructs with 2'-O-methyl ribonucleotides are indicated by underlining and bold printing. FIG. 15C shows an SDS-PAGE based immunoblot illustrating the inhibition of PTEN protein expression using various of the siRNA constructs (30 nM) as depicted in FIGS. 15A and 15B, respectively. Again, p110α is used as loading control. Finally, FIG. 15D is an immunoblot indicating a prolonged protein knock-down, i.e. the inhibition of PTEN protein expression, upon administration of siRNA molecules (30 nM) with distinct 2'-O-methylribonucleotides modifications after 48 and 128 hours. As in FIG. 15C, p 110α is used as loading control.

FIGS. 16A-16C show that siRNA molecules with distinct 2'-O-methylribonucleotides modifications which are specific for Akt1 and p103 mRNA show increased stability in serum and mediate protein knock-down in HeLa cells. More particularly, FIG. 16A (SEQ ID) NOs: 153-164, respectively in order of appearance) indicates on the left panel the various constructs used whereby again 2'-O-methylribonucleotides are underlined and printed in bold. The integrity of the indicated siRNA molecules after incubation in serum is shown in the right panel. FIG. 16B shows an immunoblot of Akt1, Akt2 and Akt phosphorylation and p110 being used as a loading control upon transfection of the cells with the indicated siRNAs (30 mM). FIG. 16C (SEQ ID NOs: 165-174, respectively in order of appearance) shows various p110β specific siRNA constructs (left panel) with the 2'-O-methyl modifications being underlined and printed in bold, and the result of an immunoblot analysis (right panel) of the inhibition of the phosphorylation of the downstream kinase Akt1 by said siRNA constructs p110α has been used as a loading control.

FIGS. 17A-17B show the efficacy of various RNAi molecules with hairpin structures as dose response curve while FIG. 17B shows the structure of the RNAi molecules the result of which is depicted in FIG. 17A. Synthetic siRNAs with different loops are functional in reducing the p110β, Akt1 and Akt 2 expression. (14A) Inhibition of p110β mRNA expression in siRNA transfected HeLa cells. Samples were analyzed in parallel for the level of p110β mRNA expression 24 h after transfection of the indicated siRNAs. The transfected bimolecular siRNAs (21mer with 3' TT overhangs, molecule 1AB) or the monomolecular siRNAs with loop structures are schematically shown. Note that the position of the loops (HIV derived pA-loop; $(A)_{12}$-loop) (SEQ ID NO: 175) relative to the antisense sequence is reversed in 3A, 4A relative to 3B, 4B. The 2AB siRNA molecule contains 6 mismatches in the 21mer duplex and serves as a negative control together with the untreated sample. RNA was prepared and subjected to real time RT-PCR (Taqman) analysis. p110β mRNA levels are shown relative to the mRNA levels of p110α, which serve as an internal reference. Each bar represents triplicate transfections (±standard deviation). HeLa cells were transfected at 50% confluency (2500 cells per 96 well) with siRNAs at the indicated concentrations in growth medium.

FIGS. 18A-18C show the efficacy of various RNAi molecules with intermolecular and intramolecular loop structures as dose response curves. (18A) (SEQ ID NO. 175) Inhibition of Akt1 mRNA expression in siRNA transfected HeLa cells. Samples were analysed in parallel for the level of Akt1 and Akt2 mRNA expression 24 h after transfection of the indicated siRNAs. The different loops (A-loops, GAGA-loop and a polyethyleneglycol (PEG)-linker) and their putative secondary structure are shown schematically. The siRNA molecule 9A is specific for Akt2 and serves as a negative control. Note that 10A and 10B do not contain self-complementary sequences and are transfected in combination. Akt1 mRNA levels are shown relative to the mRNA levels of p110β, which served as internal control. (18B) (SEQ ID NO: 175) Inhibition of Akt2 mRNA expression in HeLa cells transfected with the indicated siRNA molecules. Akt2 mRNA levels are shown relative to the mRNA levels of p110β. The Akt1 specific molecule 7A serves here as a negative control.

FIG. 18C shows a Western Blot analysis on Akt protein depicting the functionality of synthetic siRNAs with different loops in specifically reducing the Akt1 and Akt 2 expression. Inhibition of Akt1 and Akt2 protein expression were analysed by immunoblot. The cells were harvested 48 h after transfection of the indicated hairpin siRNAs (20 nM), Cell extracts were separated by SDS-PAGE and analysed by immunoblotting using anti-p110 antibody, anti Akt 1/2. Similar results were obtained with an antibody specific for the phosphorylated form of Akt1. The positions of p110α, another catalytic subunit of PI 3-kinase, which was used as a loading control, and of Akt1, Akt2 and phosphorylated Akt (P*-Akt) are indicated on the left.

DETAILED DESCRIPTION

The present inventors have surprisingly found that small interfering RNAs can be designed that are both highly specific and active as well as stable under the reaction conditions typically encountered in biological systems such as biochemical assays or cellular environments. The various interfering RNAs previously described by Tuschl et al. (see, for example, WO01/75164) provide for a length of 21 to 23 nucleotides and a modification at the 3' end of the double-stranded RNA. The present inventors found that stability problems of interfering RNA, including small interfering RNA (siRNA) which is generally referred to herein in the following as RNAi, actually result from attack by endonucleases rather than exonucleases as previously thought. This surprising observation permitted the present inventors to develop the methods and compositions that are the subject of the present invention.

Structure of RNAi Molecules

Figure 1:
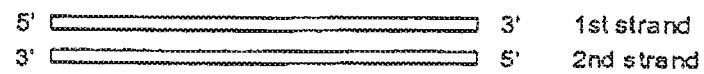
FIG. 1 shows a schematic illustration defining the terminology as used herein. The upper of the two strands is the first strand and the antisense strand of the targeted nucleic acid such as mRNA. The second strand is the one which essentially corresponds in its sequence to the targeted nucleic acid and thus forms the sense strand. Both, the first strand and second strand form a double-stranded structure, typically through Watson Crick base pairing.

The present invention provides new forms of interfering RNA. RNAi consists of a ribonucleic acid comprising a double-stranded structure, formed by a first strand and a second strand. The first strand comprises a stretch of contiguous nucleotides (the first stretch of contiguous nucleotides) that is at least partially complementary to a target nucleic acid. The second strand also comprises a stretch of contiguous nucleotides where the second stretch is at least partially identical to a target nucleic acid. The very basic structure of this ribonucleic acid is schematically shown in FIG. 1. The first strand and said second strand may be hybridized to each other to form a double-stranded structure. The hybridization typically occurs by Watson Crick base pairing.

The ribonucleic acids of the invention are, however, not necessarily limited in length to such a double-stranded structure. For example, further nucleotides may be added to each strand and/or to each end of any of the strands forming the RNAi. Depending on the particular sequence of the first stretch and the second stretch, the hybridization or base pairing is not necessarily complete or perfect, which means that the first stretch and the second stretch are not 100% base paired due to mismatches. One or more mismatches may also be present within the duplex. Such mismatches have no effect on the RNAi activity if placed outside a stretch of preferably 15, 16 or 17 matching nucleotides. If mismatches are placed to yield only 15 or less contiguous matching nucleotides, the RNAi molecule typically shows a reduced activity in down regulating mRNA for a given target compared to a 17 matching nucleotide duplex.

The first stretch of contiguous nucleotides of the first strand is essentially complementary to a target nucleic acid, more advantageously to a part of the target nucleic acid. The term "complementary" as used herein preferably means that the nucleotide sequence of the first strand hybridizes to a nucleic acid sequence of a target nucleic acid sequence or a part thereof. Typically, the target nucleic acid sequence or target nucleic acid is, in accordance with the mode of action of interfering ribonucleic acids, a single stranded RNA, more preferably an mRNA. Such hybridization occurs most likely through Watson Crick base pairing but, however, is not necessarily limited thereto. The extent to which the first strand and more particularly the first stretch of contiguous nucleotides of the first strand is complementary to a target nucleic acid sequence can be as high as 100% and be as little as 80%, advantageously 80-100%, more advantageously 85-100%, most advantageously 90-100%. Optimum complementarity seems to be 95-100%. Complementarity in this sense means that the aforementioned range of nucleotides, such as, e.g., 80%-100%, depending on the particular range, of the nucleotides are perfect by Watson Crick base pairing.

Complementarity of the Strands

It is shown in one aspect of the present invention that the complementarity between the first stretch of nucleotides and the target RNA has to be 18-19 nucleotides; stretches of as little as 17 nucleotides even with two sequence specific overhangs are not functional in mediating RNAi. Accordingly, in a duplex having a length of 19 nucleotides or base pairs a minimum complementarity of 17 nucleotides or nucleotide base pairs is acceptable, allowing for a mismatch of two nucleotides. In the case of a duplex consisting of 20 nucleotides or base pairs a complementarity of 17 nucleotides or nucleotide base pairs is allowable and functionally active. The same principle applies to a duplex of 21 nucleotides or base pairs with a total of 17 complementary nucleotides or base pairs. The extent of complementarity required for a length of a duplex, i.e. of a double stranded structure, can also be based on the melting temperature of the complex formed by either the double stranded structure as described herein or by the complex of the first stretch of the first strand and the target nucleic acid.

The skilled artisan will understand that all of the ribonucleic acids of the present invention are suitable to cause or being involved in methods of RNA mediated interference such as those described, for example, in WO 99/32619, WO 00/44895 and WO 01/75164.

Length of the RNAi Molecules

The first strategy by which an interfering ribonucleic acid molecule may be designed according to the present invention is to have an optimum length of 18 or 19 nucleotides of the stretch that is complementary to the target nucleic acid. It is also within the scope of the present invention that this optimum length of 18 or 19 nucleotides is the length of the double stranded structure in the RNAi used. This length requirement clearly differs from that described in, for example, WO 01/75164. It is within the scope of the present invention that any further design, both according to the present invention and as previously described by others, can be realised in connection with an interfering ribonucleic acid having such length characteristics, i.e. a length of 18 or 19 nucleotides.

End Modification of the RNAi Molecules

The second strategy for the design of an interfering ribonucleic acid molecule is to have a free 5' hydroxyl group, (also referred to herein as a free 5' OH-group) at the terminus of the first strand. A free 5' OH-group means that the most terminal nucleotide forming the first strand is present and is thus not modified, particularly not by an end modification. Typically, the terminal 5'-hydroxy group of the second strand, respectively, is also present in an unmodified manner. In a more preferred embodiment, the 3'-end of the first strand and first stretch, respectively, also is unmodified so as to present a free OH-group (also referred to herein as a free 3'OH-group), whereby the design of the 5' terminal nucleotide is the one of any of the embodiments described above. Preferably such a free OH-group also is present at the 3'-end of the second strand and second stretch, respectively. In other embodiments of the ribonucleic acid molecules as described previously according to the present invention the 3'-end of the first strand and first stretch, respectively, and/or the 3'-end of the second strand and second stretch, respectively, may have an end modification at the 3' end.

As used herein the terms free 5'OH-group and 3'OH-group also indicate that the respective 5' and 3' terminal nucleotides of the polynucleotide present an OH-group. Such OH-group may stein from either the sugar moiety of the nucleotide, more preferably from the 5' position in the case of the 5'OH-group and from the 3' position in the case of the 3'OH-group, or from a phosphate group attached to the sugar moiety of the respective terminal nucleotide. The phosphate group may in principle be attached to any OH-group of the sugar moiety of the nucleotide. Preferably, the phosphate group is attached to the 5'OH-group of the sugar moiety in the case of the free 5'OH-group and/or to the 3'OH-group of the sugar moiety in the case of the free 3'OH-group still providing what is referred to herein as free 5' or 3' OH-group.

The term "end modification" as used herein in connection with any strategy for the design of RNAi or any embodiment of RNAi disclosed herein, means a chemical entity added to the most 5' or 3' nucleotide of the first and/or second strand. Examples of such end modifications include, but are not limited to, inverted (deoxy) abasics, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; ONO; $NO_2$, $N_3$; heterocycloalkyl; heterocycloalkaryl; aminoalkylamino; polyalkylamino or substituted silyl, as, among others, described in European patents EP 0 586 520B1 or EP0 618 925 B1.

As used herein, alkyl or any term comprising "alkyl" means any carbon atom chain comprising 1 to 12, preferably 1 to 6 and more, preferably 1 to 2 C atoms.

A further end modification is a biotin group, which may preferably be attached to either the most 5' or the most 3' nucleotide of the first and/or second strand, or to both ends. In a more preferred embodiment the biotin group is coupled to a polypeptide or a protein. It is also within the scope of the present invention that the polypeptide or protein is attached through any of the end modifications described herein. The polypeptide or protein may confer further characteristics to the nucleic acid molecules of the invention. For example, the polypeptide or protein may act as a ligand to another molecule. If the other molecule is a receptor the receptor's function and activity may be activated by the binding ligand. The receptor may show an internalization activity which provides for effective transfection of the ligand bound inventive nucleic acid molecules. An example of a ligand that may be coupled to the nucleic acid molecules of the invention is VEGF and the corresponding receptor is the VEGF receptor.

Various possible embodiments of the RNAi of the present invention having different kinds of end modification(s) are presented in the Table 1 below:

TABLE 1

Various embodiments of the interfering ribonucleic acid according to the present invention

| | | $1^{st}$ strand/$1^{st}$ stretch | $2^{nd}$ strand/2nd stretch |
|---|---|---|---|
| 1.) | 5'-end | free OH | free OH |
| | 3'-end | free OH | free OH |
| 2.) | 5'-end | free OH | free OH |
| | 3'-end | end modification | end modification |
| 3.) | 5'-end | free OH | free OH |
| | 3'-end | free OH | end modification |
| 4.) | 5'-end | free OH | free OH |
| | 3'-end | end modification | free OH |
| 5.) | 5'-end | free OH | end modification |
| | 3'-end | free OH | free OH |
| 6.) | 5'-end | free OH | end modification |
| | 3'-end | end modification | free OH |
| 7.) | 5'-end | free OH | end modification |
| | 3'-end | free OH | end modification |
| 8.) | 5'-end | free OH | end modification |
| | 3'-end | end modification | end modification |

The various end modifications as disclosed herein are preferably located at the ribose moiety of a nucleotide of the ribonucleic acid. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasics are nucleotides, either deoxyribonucleotides or ribonucleotides which do not have a nucleobase moiety. This kind of compound is, among others, described in Sternberger et al. (2002), Antisense. Nucl. Ac. Drug Dev. 12:143.

Any of the aforementioned end modifications may be used in connection with the various embodiments of RNAi depicted in Table 1. It is particularly advantageous to inactivate the sense strand of any of the RNAi forms or embodiments disclosed herein, preferably via an end modification, and more preferably a 5' end modification. The advantage of this strategy arises from the inactivation of the sense strand which corresponds to the second strand of the ribonucleic acids described herein, which might otherwise interfere with an unrelated single-stranded RNA in the cell. Thus the expression and more particularly the translation pattern of the transcriptome of a cell is more specifically influenced. This effect is also referred to as an off-target effect. Referring to Table 1 those embodiments depicted as embodiments 7 and 8 are particularly advantageous in the above sense as the modification results in an inactivation of the—target unspecific—part of the RNAi (which is the second strand) thus reducing any unspecific interaction of the second strand with single-stranded RNA in a cellular or similar system where the RNAi according to the present invention is going to be used to knock down specific ribonucleic acids and proteins, respectively.

Blunt-Ended RNAi Molecules

A third strategy provided by the present invention involves a ribonucleic acid comprising a double-stranded structure having a first strand and a second strand, where the first strand comprises a first stretch of contiguous nucleotides and where the first stretch is at least partially complementary to a target nucleic acid, and the second strand comprises a second stretch of contiguous nucleotides where the second stretch is at least partially identical to a target nucleic acid, where the double-stranded structure is blunt-ended. As used herein the term double-stranded structure also is referred to as duplex. This design of RNAi clearly differs from, e.g., that described by Tuschl et al. in WO 01/75164, which contains a 3'-overhang. As used herein the term overhang refers to a double-stranded structure where at least one end of one strand is longer than the corresponding end of the other strand ("the counter strand") forming the double-stranded structure. Preferably, the first stretch is identical to the first strand and the second stretch is identical to the second strand.

It also is advantageous to employ a combination of the design principles described above, i.e. to prepare RNAi molecules that are blunt-ended and that have an end modification of either the first or the second strand or both. In other words, it is within the scope of the present invention to have blunt-ended RNAi carrying any end modification scheme as depicted in Table 1.

RNAi Molecules Having a 5' Overhang

The fourth strategy of the present invention is to have an overhang at the 5'-end of the ribonucleic acid. More particularly, such overhang may in principle be present at either or both the first strand and second strand of the ribonucleic acid according to the present invention. The length of the overhang may be as little as one nucleotide and as long as 2 to 8 nucleotides, preferably 2, 4, 6 or 8 nucleotides. It is within the present invention that the 5' overhang may be located on the first strand and/or the second strand of the ribonucleic acid. The nucleotide(s) forming the overhang may be (a) deoxyribonucleotide(s), (a) ribonucleotide(s) or a continuation thereof.

The overhang preferably comprises at least one deoxyribonucleotide, whereby said one deoxyribonucleotide is preferably the most 5'-terminal one. It is within the present invention that the 3'-end of the respective counter-strand of the inventive ribonucleic acid does not have an overhang, more preferably not a deoxyribonucleotide overhang. Here again, any of the inventive ribonucleic acids may comprise an end modification scheme as outlined in connection with Table 1 and/or an end modification as outlined herein.

RNAi Molecules Having Modified Nucleotides

A fifth strategy for the design of interfering ribonucleic acids subject to the present application resides in the formation of a certain pattern of modified nucleotides on at least one of the strands and more particularly on one of the stretches of contiguous nucleotides of the ribonucleic acid(s) according to the present invention. The type of modification of the nucleotides may be the same as that discussed in connection with the other strategies for designing interfering RNA disclosed herein. Advantageously, the modification is an end modification as described herein, such as, e.g., inverted abasics, methoxy, or amino and the like at the ribose moiety of at least one nucleotide forming the ribonucleotide acids according to the present application. The modification of the nucleotides may be any form of modification described herein, more particularly the kind of modification as described herein as end modification, except that the so-called end modification is not necessarily located at terminal nucleotides. Rather the modification may occur at a non-terminal nucleotide. Under such conditions the modification is preferably attached to the ribose moiety of the—to be—modified nucleotide and even more preferably to the 2' position of the ribose moiety.

Combinations of Design Elements

It is also within the present invention that any ribonucleic acid designed according to this strategy may also have the features conferred to a ribonucleic acid according to the present application by any of the other design strategies disclosed herein. Accordingly, the interfering ribonucleic acid having a pattern of modified nucleotides may have an end modification, an end modification scheme, may be blunt ended or may have a 5' overhang or any combination of two or more of these elements or characteristics.

Apart from the aforementioned modifications which may be presented either as end modifications or as modification pattern, the ribonucleic acid backbone as such may be further modified by forming different links between the nucleotides. Examples of such different links are described, among others, in EP 0 586 520 B1 and EP 0 618 925 B1. Of particular interest here are internal modification(s) of the ribonucleic acid backbone which have been shown to confer higher nuclease resistance of ribooligonucleotides. In a preferred embodiment the modification of the modified nucleotide is a methylation of the 2'-OH-group of the ribose moiety of the nucleotide to form a methoxy group.

In a preferred embodiment, both strands, and more particularly both the first stretch and the second stretch show this kind of modification of the nucleotides forming said strands and stretches, respectively. However, it is also within the present invention that either the first strand and first stretch, respectively, or the second strand and second stretch, respectively, show this particular pattern of modification of the nucleotides. As used herein, the term group of modified nucleotides or flanking group of nucleotides may comprise or represent one or more nucleotides.

A pattern of modification of the nucleotides in a contiguous stretch of nucleotides may be realised such that the modification is contained within a single nucleotide or group of nucleotides that are covalently linked to each other via standard phosphodiester bonds or, at least partially, through phosphorothioate bonds. In the event that such a modified nucleotide or group of modified nucleotides does not form the 5'-end or 3'-end of the stretch, a flanking nucleotide or group of nucleotides is arrayed on both sides of the modified nucleotide or group, where the flanking nucleotide or group either is unmodified or does not have the same modification of the preceding nucleotide or group of nucleotides. The flanking nucleotide or group of nucleotides may, however, have a different modification. This sequence of modified nucleotide or group of modified nucleotides, respectively, and unmodified or differently modified nucleotide or group of unmodified or differently modified nucleotides may be repeated one or more times. Preferably, the sequence is repeated more than one time. The pattern of modification is discussed in more detail below, generally referring to a group of modified nucleotides or a group of unmodified nucleotides whereby each of said group may actually comprise as little as a single nucleotide. The term "unmodified nucleotide" as used herein means either not having any of the aforementioned modifications at the nucleotide forming the respective nucleotide or group of nucleotides, or having a modification which is different from the one of the modified nucleotide and group of nucleotides, respectively.

It is also within the present invention that the modification of the unmodified nucleotide(s) wherein such unmodified nucleotide(s) is/are actually modified in a way different from the modification of the modified nucleotide(s), can be the same or even different for the various nucleotides forming said unmodified nucleotides or for the various flanking groups of nucleotides. That is, a group of modified nucleotides may contain two or more different modified nucleotides within a single group.

The pattern of modified and unmodified nucleotides may be such that the 5'-terminal nucleotide of the strand or of the stretch starts with a modified group of nucleotides or starts with an unmodified group of nucleotides. However, in an alternative embodiment it is also possible that the 5'-terminal nucleotide is formed by an unmodified group of nucleotides.

This kind of pattern may be realised either on the first stretch or the second stretch of the interfering RNA or on both. A 5' phosphate on the target-complementary strand of the siRNA duplex is required for siRNA function, suggesting that cells check the authenticity of siRNAs through a free 5' OH (which can be phosphorylated) and allow only such bona fide siRNAs to direct target RNA destruction (Nykanen, et al. (2001), (Cell 107, 309-21).

Preferably, the first stretch shows a pattern of modified and unmodified groups of nucleotides, i.e. of group(s) of modified nucleotides and flanking group(s) of nucleotides, whereas the second stretch does not show this kind of pattern. This may be useful insofar as the first stretch is actually the more important one for the target-specific degradation process underlying the interference phenomenon of RNA so that for specificity reasons the second stretch can be chemically modified so it is not functional in mediating RNA interference.

However, it is also within the present invention that both the first stretch and the second stretch have this kind of pattern. Preferably, the pattern of modification and non-modification is the same for both the first stretch and the second stretch.

In a particular embodiment, the modified nucleotides or groups of modified nucleotides of one strand of the molecule are complementary in position to the modified nucleotides or groups of nucleotides of the other strand. This possibility is schematically depicted in FIG. 2A. In an alternative embodiment, there is a phase shift between the patterns of modification of the first stretch and first strand, respectively, relative to the pattern of modification of the second stretch and second strand, respectively. Preferably, the shift is such that the modified group of nucleotides of the first strand corresponds to the unmodified group of nucleotides of the second strand and vice versa. This possibility is illustrated schematically in FIG. 2B. In another embodiment, there is a partial shift of the pattern of modification so that the modified groups overlap as illustrated in FIG. 2C. The groups of modified nucleotides in any given strand may optionally be the same length, but may be of different lengths. Similarly, the groups of unmodified nucleotides in any given strand may optionally be the same length, or of different lengths.

In a preferred embodiment the second (penultimate) nucleotide at the terminus of the strand and stretch, respectively, is an unmodified nucleotide or the beginning group of unmodified nucleotides. Preferably, this unmodified nucleotide or unmodified group of nucleotides is located at the 5'-end of the first and second strand, respectively, and even more preferably at the terminus of the first strand. In a further preferred embodiment the unmodified nucleotide or unmodified group of nucleotides is located at the 5'-end of the first strand and first stretch, respectively. In a preferred embodiment the pattern consists of alternating single modified and unmodified nucleotides.

In a particular embodiment of this aspect of the present invention the interfering ribonucleic acid subject comprises two strands, whereby a 2'-O-methyl modified nucleotide and a non-modified nucleotide, preferably a nucleotide which is not 2'-O-methyl modified, are incorporated on both strands in an alternating fashion, resulting in a strand having a pattern MOMOMOMOM etc. where M is a 2'-O-methyl nucleotide and O is a non-modified nucleotide. The same sequence of 2'-O-methyl modification and non-modification exists on the second strand, and preferably there is a phase shift between the two strands such that the 2'-O-methyl modified nucleotide on the first strand base pairs with a non-modified nucleotide(s) on the second strand and vice versa. This particular arrangement, i.e. base pairing of 2'-O-methyl modified and non-modified nucleotide(s) on both strands is particularly preferred in case of short interfering ribonucleic acids, i.e. short base paired double-stranded ribonucleic acids because it is assumed, although the present inventors do not wish to be bound by that theory, that a certain repulsion exists between two base-pairing 2'-O-methyl modified nucleotides which would destabilise a duplex, and particularly short duplexes, containing such pairings.

In a "phase shifted" arrangement of this nature, it is preferred if the antisense strand starts with a 2'-O-methyl modified nucleotide at the 5' end whereby consequently the second nucleotide is non-modified, the third, fifth, seventh and so on nucleotides are thus again 2'-O-methyl modified whereas the second, fourth, sixth, eighth and the like nucleotides are non-modified nucleotides. Again, not wishing to be bound by any theory, it seems that a particular importance may be ascribed to the second, and optionally fourth, sixth, eighth and/or similar position(s) at the 5' terminal end of the antisense strand which should not comprise any modification, whereas the most 5' terminal nucleotide, i.e. the first 5' terminal nucleotide of the antisense strand may exhibit such modification with any uneven positions such as first, optionally third, fifth and similar position(s) at the antisense strand may be modified. In further embodiments the modification and non-modification, respectively, of the modified and non-modified nucleotide(s), respectively, may be any modification as described herein.

Although not limited thereto, the double-stranded structure of the inventive ribonucleic acid, which is also referred to as duplex, is formed by the first strand and second strand, respectively, or the first and second stretch of contiguous nucleotides. The length of the first stretch and second stretch, respectively, is typically about 15 to about 23, preferably 17 to 21, and more preferably 18 or 19 bases. A length of less than 30 nucleotides, preferably less than 21 nucleotides does not induce an interferon response in any biological system which is capable of showing RNA interference and an interferon response. This apparently is because a given cell experiences profound physiological changes when double-stranded RNA longer than 30 base pairs binds and activates the protein kinase PKR and 2',5'-oligoadenylate synthetase. Activated PKR stalls translation via phosphorylation of eIF2a, activated 2',5'-AS causes mRNA degradation. These effects are not desired in target validation and animal models because they override the effect of the target specific knockdown on the phenotype.

RNAi Oligonucleotides with Loop Structures

In a sixth strategy for designing interfering ribonucleic acids of the present invention, the ribonucleic acid comprises a double-stranded structure where the double-stranded structure has a first strand comprising a first stretch of contiguous nucleotides that is at least partially complementary to a target nucleic acid, and a second strand comprising a second stretch of contiguous nucleotides that is at least partially identical to a target nucleic acid, and where one terminus of the first strand and one terminus of the second strand are linked by a loop structure.

In one embodiment the loop structure is comprised of a non-nucleic acid polymer. Suitable non-nucleic acid polymers include polyethylene glycol or similar polymers. The polymer may be chosen in such a manner that the two linked strands may hybridize to each other. This requires that the polymer has to have a certain molecular "hinge" structure or molecular flexibility to allow the bending of the molecule so as to allow that both stretches get in close contact and in a three-dimensional orientation which permits hybridization. In principle any molecule which complies with this requirement may be used in connection with the present invention. For example, amino acid based molecules may also be used. Such amino acid based molecules may be either homopolymers or heteropolymers. A useful example is a homopolymer consisting of seven glycine residues which allows the generation of a hinge as required to bring the two stretches to hybridize in the close proximity as needed. A suitable glycine based hinge is described, e.g., in Guan K. L. and Dixon J. B. (1991), *Anal. Biochem.* 192, 262. In another embodiment the hinge may be formed by crown ethers of a type that is known in the art.

In an alternative embodiment the loop is comprised of a nucleic acid moiety. In the context of these loops, LNA as described in Elayadi and Corey (2001) *Curr. Opin. Investig. Drugs.* 2(4):558-61 and Orum and Wengel (2001) *Curr. Opin. Mol. Ther.* 3(3):239-43; and PNA are regarded as nucleic acids and may also be used as loop forming polymers. Basically, the 5'-terminus of the first strand may be linked to the 3'-terminus of the second strand. As an alternative, the 3'-end of the first strand may be linked to the 5'-terminus of the second strand. The nucleotide sequence forming the loop structure is, in general, not critical. However, the length of the nucleotide sequence forming such loop seems to be critical for steric reasons. Accordingly, a minimum length of four nucleotides appears to be appropriate to form the required loop structure. In principle, the maximum number of nucleotides forming the hinge or the link between both stretches to be hybridized is not limited. However, the longer a polynucleotide is, the more likely secondary and tertiary structures are formed and this can affect the required orientation of the stretches that must form the hybridised structure. Preferably, a maximum number of nucleotides forming the hinge is about 12 nucleotides. It is within the scope of the present invention that any of the designs described above may be combined with this sixth strategy, i.e. by linking the two strands covalently in a manner that back folding (loop) can occur through a loop structure or similar structure.

The present inventors surprisingly have found that if the loop is placed 3' of the antisense strand, i.e. the first strand of the ribonucleic acid(s) according to the present invention, the resulting RNAi molecules have higher activity than molecules where the loop is placed 5' of the antisense strand. This result is contrary to the conventional wisdom that the orientation of the loop is irrelevant, based on the assumption that any RNAi, is subject to a processing during which non-loop linked RNAi is generated. If this was the case, however, the clearly observed increased activity of those structures having the loop placed 3' of the antisense could not be explained. Accordingly, a preferred arrangement in 5'→3' direction of this kind of small interfering RNAi is second strand-loop-first strand.

Expression of RNAi from a Vector

The respective constructs may be incorporated into suitable vector systems. Preferably the vector comprises a promoter for the expression of RNAi. Suitable promoters include pol III and the U6, H1, 7SK promoters as described in Good et al (1997) *Gene Ther,* 4, 45-54.

Use of RNAi for Gene Knockdown and Target Validation

The ribonucleic acid molecules according to the present, invention have general applicability and permit knockdown or knockout of any desired coding nucleotide such as an mRNA, i.e. the expression of any gene producing an RNA may be modified. A particular application is the use of the inventive ribonucleic acid for target validation. As used herein, target validation means a process that involves determining whether a DNA, RNA, or protein molecule is directly involved in a biological process. Preferably the biological process is causally involved in a disease or non-standard condition and the gene under study is therefore a suitable target for development of a new therapeutic compound.

Sequence homology studies have successfully classified genes into target families. The enormous task of deciphering which of these targets are key players in diseases and which should be used for subsequent drug development needs to be addressed in an efficient manner. Therefore, the knockdown of gene expression should be reduced by 50-100%, preferably by 90% to see significant effects on the phenotype. In other cases depending on the gene, a knockdown of as little as 20% might be sufficient to yield a phenotype. A phenotype will be defined by comparison of cells containing functional RNAi molecules with cells containing non functional RNAi molecules. This will ensure a significant readout even under conditions where the protein function is inhibited only partially. Generally there is no linear correlation between the degree of mRNA reduction and the extent of the change in phenotype. For some proteins a reduction of about 20% of the protein is sufficient to create a change in the phenotype whereas in case of other genes and mRNA, respectively, as little as 5 to 10% remaining protein is sufficient to maintain an observed phenotype.

A further use of the ribonucleic acid molecules according to the present invention is its use for the manufacture of a medicament or its use as a medicament. Such a medicament may either be used for the treatment and/or prevention of diseases or conditions such as any type of cancer where a gene and its product have been linked to the onset, cause or progression of this disease. Additionally, such a medicament may be used to treat diseases where the presence or overexpression of a gene product causes a pathological phenotype. In a preferred embodiment the disease is characterised by a gain of function and may be remedied through application or administration of the corresponding, biologically active RNAi. Diseases or conditions which may be treated by the medicament comprising a ribonucleic acid as disclosed herein, may be selected from the group comprising cancer, heart diseases, metabolic diseases, dermatological diseases, inflammatory diseases, immune system disorders and autoimmune disorders. The various forms of cancer include, but are not limited to, solid tumors and tumors of the hematopoietic system, such as glioblastoma, prostate cancer, breast cancer, lung cancer, liver cancer, pancreatic cancer and leukaemia. Metabolic diseases include, but are not limited to, obesity and diabetes. Dermatological diseases include, but are not limited to, psoriasis.

In another aspect the ribonucleic acid molecules according to the present invention may be used as diagnostics, preferably for those diseases as specified in connection with the above-mentioned diseases and conditions. Such diagnosis could be based on the observation that upon applying the ribonucleic acid molecules according to the present invention to a sample which preferably contains cells, a change in the expression pattern of the sample occurs. Preferably such sample comprises cells from a subject from whom it is assumed that it may exhibit said disease or condition to be treated or a predisposition therefor.

A further application of the nucleic acids according to the present invention resides in their use in the screening of pharmaceutically active compounds and/or lead optimization. The latter is done such as to monitor or determine the effect of candidate drugs such as small molecules and compare the effect created by said candidate drugs with the effect observed upon administering specific RNAi designed on the basis of the principles disclosed herein. In doing so candidate drugs having off-target effects may be eliminated from the screening process whereas those candidate drugs which create a similar or identical phenotype are deemed as highly relevant lead compound or may even be a pharmaceutically active compound themselves. In this approach, the highly specific RNAi molecules act as a gold standard against which candidate drugs are measured.

In a further aspect the invention is related to a cell, preferably a knockdown cell, which contains a ribonucleic acid as disclosed herein. Such a cell preferably is either isolated or contained in a tissue or even organ which again preferably is not contained in an organism. However, the cell may also be contained in an organism. The cell is preferably a cell which is involved in the disease or condition which is to be treated by the ribonucleic acids of the invention. This kind of knock-down cell may be used to generate an expression profile based on, e.g., mRNA or protein, in order to elucidate functional relationship and to determine downstream targets.

In a further aspect the invention is related to an organism containing a ribonucleic acid as disclosed herein. Preferably such organism is a vertebrate organism and more preferably the vertebrate organism is a mammal. A mammal as used herein is, among others and not limited thereto, an ape, a dog, a cat, a goat, a sheep, a pig, a guinea pig, a rabbit, a mouse, a rat and a human being.

In a still further aspect the present invention provides compositions containing one or more ribonucleic acids according to the present invention. Preferably such composition comprises negative and positive controls either in combination with the effective ribonucleic acid or separated therefrom. Such composition may further comprise a solvent, preferably a buffer.

In a further aspect the present invention is related to a pharmaceutical composition containing a ribonucleic acid according to the present invention and a pharmaceutically acceptable carrier. Pharmaceutically acceptable carriers are known in the art and comprise, among others, diluent, buffers and the like. Suitable carriers are described, for example, in Remington's Pharmaceutical Sciences (18th edition, 1990, Mack Publishing Co.). The pharmaceutical composition may comprise additional pharmaceutically active compounds. In cases where the disease or condition to be treated using the ribonucleic acid molecules of the present invention is the same or related disease of condition as that treated by the additional pharmaceutically active compound(s) then the different mode of action of the ribonucleic acid molecules and the additional compounds will produce synergistic effects.

The invention is now further illustrated by reference to the figures and examples from which further features, embodiments and advantages of the present invention may be taken.

Example 1: Dose Response of Synthetic Duplex RNAi Molecules

In this example the impact of $NH_2$ end protection groups on the activity of duplex RNAi molecules was investigated. Synthetic siRNAs were purchased from Biospring (Frankfurt, Germany). The ribooligonucleotides were resuspended in RNase free TE to a final concentration of 50 μM. In the case of bimolecular siRNA molecules equal aliquots (100 μM) were combined to a final concentration of 50 μM. For the formation of intramolecular duplexes the siRNAs were incubated at 50° C. for 2 min in annealing buffer (25 mM NaCl; 5 mM $MgCl_2$) and were cooled down to RT. Transfections were carried out in 96 well or 10-cm plates (at 30% to 50% confluency) by using various cationic lipids such as Oligofectamine, Lipofectamine (Life Technologies), NC388 (Ribozyme Pharmaceuticals, Inc., Boulder, Colo.), or FuGene 6 (Roche) according to the manufacturer's instructions. RNAi molecules were transfected by adding pre-formed 5× concentrated complex of annealed RNAi and lipid in serum-free medium to cells in complete medium. Prior to transfection 2500 HeLa cells were plated per well 15-18 hours before transfection for the 96 well format.

The total transfection volume was 100 μl for cells plated in 96-wells and 10 ml for cells in 10 cm plates. The final lipid concentration was 0.8 to 1.2 μg/ml depending on cell density; the RNAi concentration is indicated in each experiment.

Complex formation was allowed to take place for 30 min at 37° C. Complexes were added to cells to yield a final 1× concentration of both lipid and RNAi. Depending on the analysis performed following transfection, cells were lysed using a standard cell lysis buffer for protein extraction (Klippel, A., Escobedo, J. A., Hirano, M. and Williams, L. T. (1994). Mol Cell Biol 14, 2675-2685) or a denaturing buffer for RNA isolation according to the RNA isolation kit (Invitek, Berlin (Germany) 24 to 48 hours post transfection for RNA analysis and 48 to 72 hours post transfection for protein analysis by Western Blot.

Determination of the Relative Amounts of RNA Levels by Taqman Analysis:

24 h post transfection the RNA of cells transfected in 96-wells was isolated and purified using the Invisorb RNA HTS 96 kit (InVitek GmbH, Berlin). Inhibition of PTEN mRNA expression was detected by real time RT-PCR (Taqman) analysis using 300 nM PTEN 5' primer CACCGC-CAAATTTAACTGCAGA (SEQ ID NO: 176), 300 nM PTEN 3' primer AAGGGTTTGATAAGTTCTAGCTGT (SEQ ID NO: 177) and 100 nM of the PTEN Taqman probe Fam-TGCACAGTATCCTTTTGAAGACCATAACCCA-Tamra (SEQ ID NO: 178) in combination with 40 nM 3-actin 5' primer GTTTGAGACCTTCAACACCCCA (SEQ ID NO: 179), 40 nM ft-actin 3' primer GACCAGAG-GCATACAGGGACA (SEQ ID NO: 180) and 100 nM of the (f-actin Taqman probe Vic-CCATGTACGTAGCCATCCA-GGCTGTG-Tamra (SEQ ID NO: 181). The Akt primers and probes are determined in Sternberger et al. (Sternberger, supra) and are used according to the manufacturer's instructions (Applied Biosystem; use of Amplicon Set). Also said primers and probes may be designed using the software program Primer Express (Applied Biosystem) The reaction was carried out in 50 μl and assayed on the ABI PRISM 7700 Sequence detector (Applied Biosystems) according to the manufacturer's instructions under the following conditions: 48° C. for 30 min, 95° C. for 10 min, followed by 40 cycles of 15 sec at 95° C. and 1 min at 60° C.

RNA knockdown was shown by real time RT-PCR analysis of HeLa cells transfected with 21 nt long siRNA duplex molecules unmodified and modified with either $NH_2$ or inverted Abasics groups at the 5'-end at a lipid carrier concentration of 1.0 μg/ml. Cell density was 2000 cells/well. Modifications on the 3'-end were either RNA overhangs, RNA overhangs with amino groups or DNA overhangs.

Preparation of cell extracts and immunoblotting. Cells were washed twice with cold phosphate-buffered saline and lysed at 4° C. in lysis buffer containing 20 mM Tris (pH 7.5), 137 mM NaCl, 15% (vol/vol) glycerol, 1% (vol/vol) Nonidet P-40 (NP-40), 2 mM phenylmethylsulfonyl fluoride, 10 mg aprotinin per ml, 20 mM leupeptin, 2 mM benzamidine, 1 mM sodium vanadate, 25 mM β-glycerol phosphate, 50 mM NaF and 10 mM NaPPi. Lysates were cleared by centrifugation at 14,000×g for 5 minutes and aliquots of the cell extracts containing equal amounts of protein were analyzed for protein expression by Western-blotting: Samples were separated by SDS-PAGE and transferred to nitrocellulose-filters (Schleicher & Schuell). Filters were blocked in TBST buffer (10 mM Tris-HCl (pH 7.5), 150 mM NaCl, 0.05% (vol/vol) Tween 20, 0.5% (wt/vol) sodium azide) containing 5% (wt/vol) dried milk. The respective antibodies were added in TBST at appropriate dilutions. Bound antibody was detected using anti-mouse- or anti-rabbit-conjugated horseradish peroxidase (Transduction Laboratories) in TBST, washed, and developed using the SuperSignal West Dura (Pierce) or ECL (Amersham) chemoluminescence substrates (c.f. Sternberger et al. (2002). *Antisense. Nucl. Ac. Drug Dev. in press.*

Antibodies. The murine monoclonal anti-p110 antibody U3A and the murine monoclonal anti-p85 antibody N7B have been described (Klippel et al., 1994, supra). Rabbit polyclonal anti-Akt and anti-phospho Akt (S473) antibodies were obtained from Cell Signaling Technology. The murine monoclonal anti-PTEN antibody was from Santa Cruz Biotechnology. The PTEN 53 specific antisense molecule, i.e. geneBloc, is described in Sternberger et al. [Sternberger, supra] having the following sequence (ucuccuuTTGTTTCT-Gcuaacga) (SEQ ID NO: 182), whereby the nucleotide depicted in lower case are ribonucleotides whereas the nucleotide in capital letters are deoxyribonucleotide. This antisense molecule is also identical to RNAi 1A without TT.

The results are shown in FIG. 3A and the respective RNAi molecules in FIG. 3B which are directed to the mRNA of PTEN. The nucleotides written in lower case letters represent ribonucleotides whereas capital letters represent deoxyribonucleotide. The term $NH_2$ indicates that the 3'-position of the ribonucleotide was modified by an amino group. The RNAi molecules used in this and other examples disclosed herein are also referred to as small interfering RNA molecules siRNA. It is to be noted that in any of the figures contained herein the upper strand is the antisense or first strand, whereas the lower strand is the sense or second strand of the interfering RNA molecule.

As can be taken from FIG. 3A amino end modifications such as amino modification and inverted abasics modification of the terminal OH group of the nucleic acid are as potent as unmodified ends when the modification is located at the 3' end of the antisense strand (see also FIG. 8A; 8B). Therefore chemical modification to stabilize or with other beneficial properties (delivery) will be tolerated without activity loss when located at the 3' OH; especially when the 3'OH is located on an overhanging nucleotide.

Figure 3C:
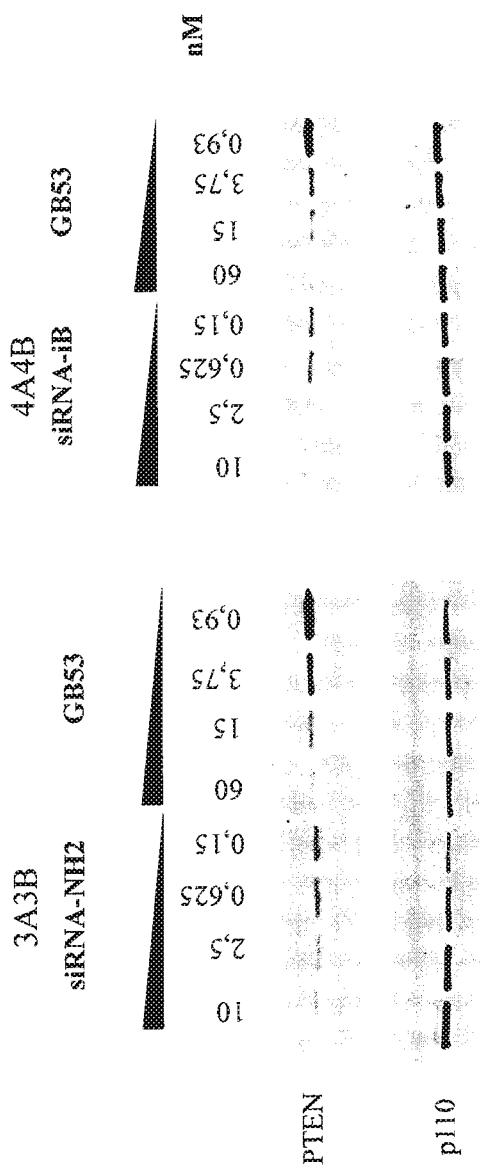

For the experiment shown in FIG. 3C similar conditions as outlined above were used. The first strand and the second strand of the RNAi were either modified by a $NH_2$ group at the 3'-position of the ribose moiety or by an inverted abasic at said positions. The first construct is designated as siRNA-$NH_2$ (3A3B) the second as siRNA-iB (4A4B). The sequence of both molecules is depicted in FIG. 3B. The term 3A3B indicates that the interfering ribonucleic acid consists of strand 3A as the antisense strand and strand 3B as the sense strand. For reason of comparison an antisense oligonucleotide designated GB53 (Sternberger et al., supra) was generated which was directed against the PTEN mRNA as well. The particularities of this latter experiment were as follows.

As may be taken from FIG. 3C end protected RNAi molecules depicted in FIG. 3B are functional in yielding a PTEN protein knockdown.

From this example it can be taken that both end protection groups render RNAi molecules active in knocking down PTEN protein. This inhibition is as efficient as inhibition with anti sense constructs but at lower concentrations used which is a clear advantage over the already very powerful antisense technology.

Example 2: Overhang Requirements for RNAi Duplex Activity In Vivo

The experimental procedures were the same as depicted in connection with Example 1 except that the PTEN mRNA targeting interfering RNAi molecules were differently designed. The results are shown in FIG. 4A as dose response curves with FIG. 4B showing the particular sequence and modifications of the interfering RNAi molecules used to generate the data depicted in FIG. 4A. The nomenclature is such that, e.g., RNAi 18 is composed of strand 18A as antisense strand and strand 18B as sense strand.

Blunt ended molecules were compared to molecules with 3'-overhangs (RNAi 18) and 5'-overhangs (RNAi 30 and RNAi 31) in their activity to knockdown PTEN mRNA in HeLa cells. The activity of blunt ended molecules (RNAi 28) and molecules with 5'-overhangs was comparable to the activity of molecules with 3'-overhangs. This shows that 3'-overhangs are not required for RNAi activity.

Figure 7A:
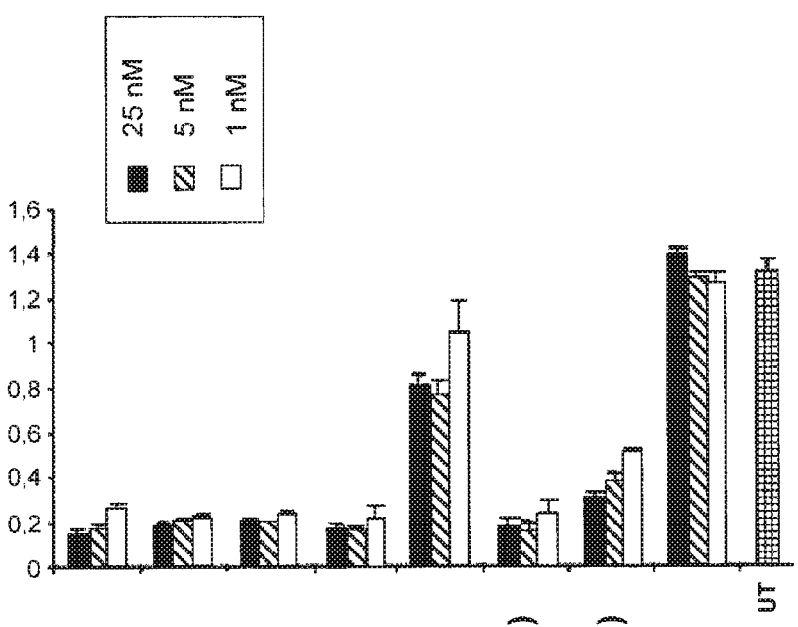

Example 3: Duplex Length Requirements of Interfering RNA Molecules for RNAi Activity In Vivo The experimental approach was similar to the one outlined in connection with Example 1 except that the interfering RNA molecules were directed against the mRNA of Akt1. The negative control to show the specificity of the RNAi molecules was again p110 mRNA. The experimental results are shown in FIG. 5A with the particularities of the interfering RNAi molecules used being represented in FIG. 5B. Similar experiments were carried out with further siRNA constructs which are depicted in FIG. 7A, left panel, whereby the arrows indicate mismatches and deoxyribonucleotide are expressed in capital letters. The inhibition of Akt1 mRNA expression in HeLa cells transfected with the indicated amounts of siRNA molecules is depicted on the right panel of FIG. 7A.

Taqman analysis on Akt RNA from HeLa cells transfected with different RNAi molecules shows that the double strand duplex of the siRNA molecules has to be longer than 17 base pairs to show activity whereas molecules with 17 base pair long duplexes or shorter are not functional even if sequence-specific overhangs are added. The shortest RNAi molecules successfully tested were 18 to 19 nucleotides or base pairs in length. It is to be noted that the design of the interfering RNA molecule 51A/51B referred to as RNAi 51 corresponds to the one as described in international patent application WO 01/75164. The RNAi molecule 55A/55B comprises a stretch of 17 nucleotides and has a clearly decreased activity in terms of degradation of Akt1 mRNA.

Figure 19A:
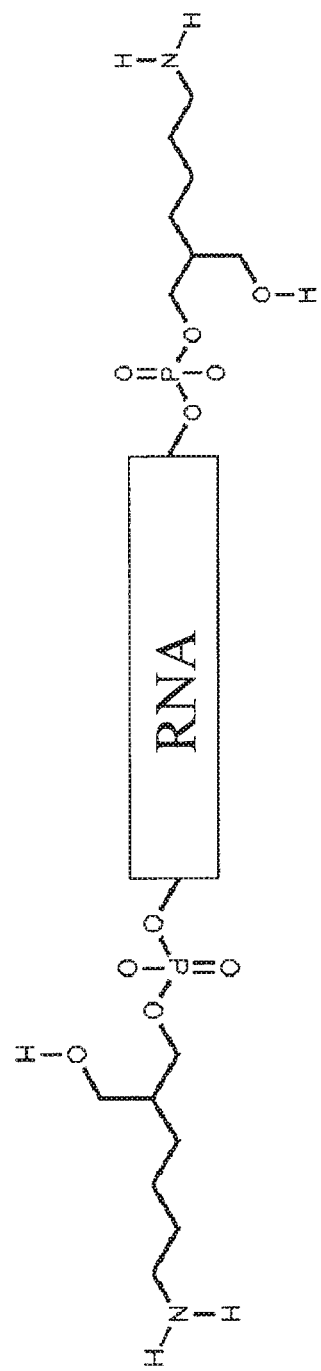
FIGS. 19A-19B show an $NH_2$ modification, also referred to herein as amino modification, which may be present at either the 3'-OH terminal nucleotide or the 5' terminal nucleotide. The amino group is attached to the phosphate which in turn is attached to the OH group of the sugar moiety, through an alkyl group comprising an alkyl chain of 1 to 8, preferably 6 C atoms, whereby the second C atom close to the phosphate group has a $CH_2OH$ group attached thereto. As an alternative the linker may be formed by an ether whereby the ether is comprised of two alcohols whereby one alcohol is an amino alcohol and the other is a dialcohol with one alcohol group involved in the formation of the ether group and the other one being an OH group located at either of the C atoms, preferably at the second C atom relative to the phosphate group.
Figure 19B:
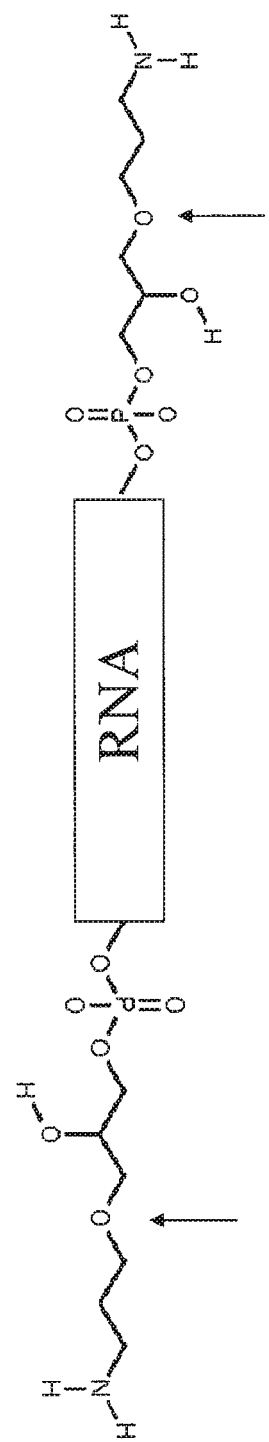

As may be taken from FIG. 7A 19 nt long duplexes are highly efficient in reducing Akt1 mRNA levels independent of the nature (deoxy- or ribonucleotides) of the 3' overhang (compare molecules 1AB, 2AB, 3AB, 4AB). The 17 nucleotide long siRNA (molecule 5AB) showed a dramatically reduced silencing activity confirming the above expressed understanding that active siRNA duplexes should be at least 18 nt or longer. Without wishing to be bound by any theory this result may be explained mechanistically by two different requirements. First, a minimum base pairing of 18 at between the antisense of the siRNA and the target mRNA may be obligatory, or second, incorporation into the RNA-induced silencing complex (RISC) requires a minimum length of the siRNA duplex. To address this question a 19 nt long siRNA duplex molecule with one and two terminal mutations (CG and UA inversion) relative to the wild type sequence was synthesised (molecules 6AB and 7AB). Both molecules, even the molecule with a stretch of only 15 nt base pairing to the target mRNA were functional in inducing the Akt1 mRNA level. Therefore, it can be concluded that the duplex length itself, but not the base pairing of the antisense siRNA with the target mRNA seems to determine the minimum length of functional siRNAs. This suggests that the length of the double-stranded helix is an important determinant for the incorporation into the RISC complex. The introduced mismatches at the terminal ends of the siRNA duplexes had little effect on RNA interference.

Given the experimental results, the minimum requirement for optimum RNAi mediated interference is thus a duplex length of 18 or 19 nucleotides, independent of the further design of the RNAi molecules such as blunt end or 5'-overhang or any other form as disclosed herein, but generally applicable to RNAi molecules. However, it has to be acknowledged that the particular design of the RNAi molecules may confer further advantages to said molecules, such as, e.g., increased efficiency and increased stability, respectively.

Example 4: Target-Antisense Homology Requirements for RNAi In Vivo

The experimental set-up was similar to the one described in example 1, whereby the RNAi is specific for Akt1. In addition, a PTEN specific interfering RNA molecule was designed and used as negative control. The results are shown in FIG. 6A and FIG. 6B Basically the same experiment was carried out using further siRNA molecules as depicted in FIG. 7B with the results being indicated in FIG. 7B (right panel) and FIG. 7C, respectively.

Having established the minimal duplex length of 18 or more than 18 nucleotides for functional siRNA molecules we asked the question how many matching nucleotides between target mRNA and siRNA are necessary for silencing activity. As shown by Taqman analysis on Akt1 RNA a stretch of 19 to 15 nucleotides perfectly matching to the target RNA, in the case of Akt1, was sufficient to mediate RNAi activity. A PTEN specific RNAi molecule did not reduce RNA amounts of Akt1 thus confirming the specificity of this approach. Molecules containing mismatches of one or two nucleotides at any or both ends of a strand were functional suggesting that a homolog stretch of 15 nt between a target mRNA and RNAi is sufficient for gene silencing.

It can be concluded from these data that unspecific gene silencing can occur by chance through unspecific binding to unrelated targets. This is based on the understanding that a stretch of 15 to 17 matching base pairs is not specific for a single gene and will occur by chance considering the complexity and size of the genome or transcriptosome of vertebrates. Apart from the above mentioned experiments the location of the mismatch also was subsequently analysed. For this purpose a 19 nt long blunt siRNA directed against PTEN mRNA was used. The sequence changes in one siRNA strand were compensated by complementary changes in the other strand to avoid disrupting duplex formation. As may be seen from both FIGS. 7B and C, respectively, a siRNA with only one point mutation in the center of the molecule was severely compromised in its ability to use mRNA and protein expression levels. This result indicates that the RNA machinery is highly discriminative between perfect and imperfect base pairing between target mRNA and siRNA in the center of the duplex. This extreme dependence on a perfect complementarity between target and siRNA has already been described for RNAi interference in the *Drosophila* system, however, not yet in connection with mammalian systems such as HeLa.

Based on this observation the present invention reduces this off-target problem of siRNA by two approaches: first, by reducing the molecule length of the siRNA molecules to the minimal requirements (18-19 nt) and thereby reducing the chance of homology to off-targets; second, by inactivation of the sense strand to prevent an unwanted RNA silencing caused by accidental complementarity of the sense strand to an unrelated target RNA (see also Example 6).

Example 5: Stability of Modified RNAi Molecules in Serum

Oligonucleotides were incubated in human serum for 15 min and two hours and loaded on 10% polyacrylamide gel with untreated controls. The results are shown in FIG. 8A. The various RNAi molecules used are shown and described in more detail in FIG. 8B.

From this example it can be taken that the RNAi duplex of RNA molecules with all nucleotides modified with 2'-O-methyl groups (RNAi molecules 79A79B and 28A28B) have higher stability in serum. It is also shown that a blunt duplex is more stable than the duplex molecule with overhangs. From this the conclusion may be drawn that end protection (e.g. iB or amino) does not increase the stability in serum. In addition, it can also be concluded that, in contrast to the understanding in the art before the filing of the present application, endonucleases are more important than exonucleases in the protection of RNAi molecules.

In view of this, in addition to the various modifications or designs of the inventive RNAi molecules as disclosed above, further or additional modification of the nucleotides may include the use of a phosphorothioate backbone of the RNAi molecules which may be either complete or partial in order to inhibit endonuclease function. A complete phosphorothioate backbone means that any of the nucleotides exhibits a phosphorothioate group whereas a partial phosphorothioate backbone means that not all of the nucleotides forming the RNAi molecule have a phosphorothioate modification. This modification is suitable to increase the lifetime of RNAi molecules irrespective of the further design of RNAi molecules. In this regard, the present invention encompasses a partially or completely phosphorothioate modified RNAi which may be realized in connection with the different strategies for the design of interfering RNA molecules as disclosed herein or with any of the designs known in the art.

Figure 9A:
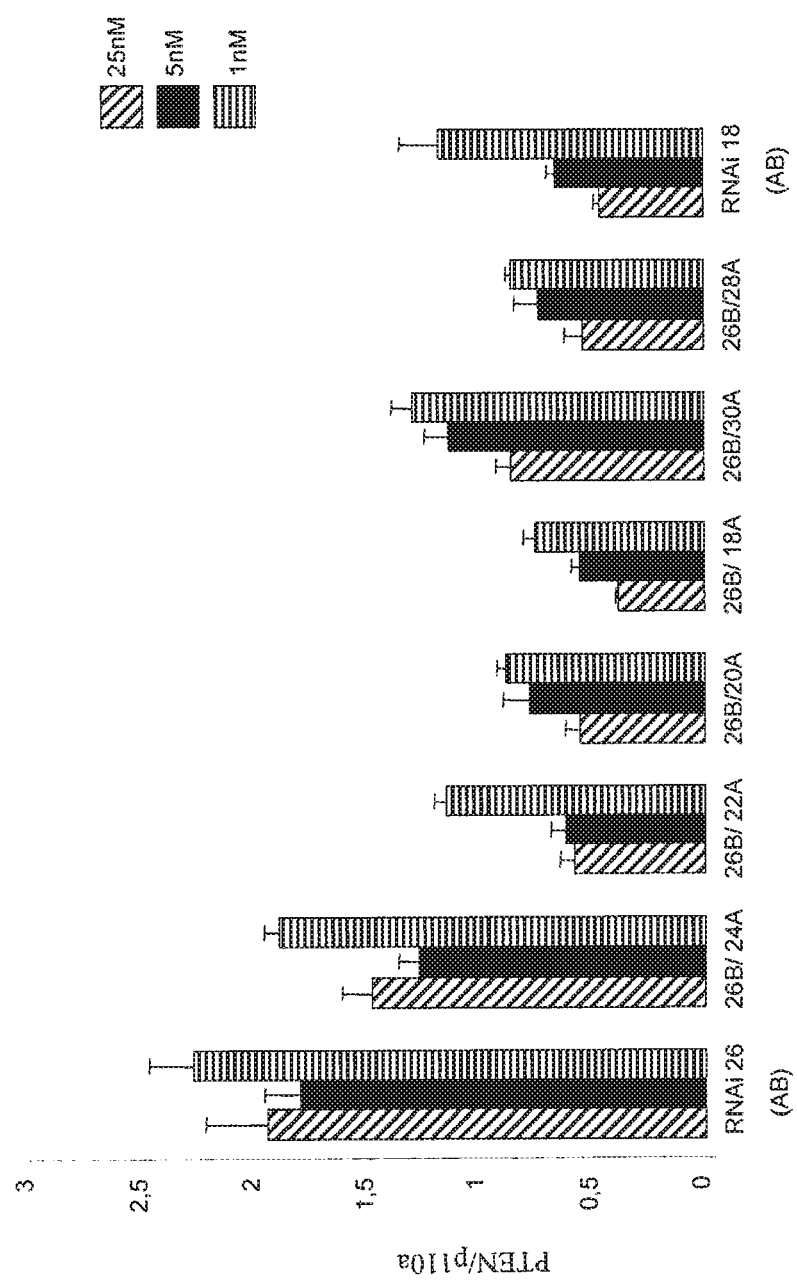

Example 6: Inactivation of the Sense Strand by $NH_2$ End Protection Groups on the 5' and 3' Ends The experimental set-up was similar to the one described in connection with Example 1 with the target nucleic acid sequence being PTEN mRNA. The concentration of HeLa cells was 2,000 cells per well. RNA of PTEN was analysed in Taqman assays after transfection of differently modified RNAi molecules. The different interfering RNA molecules used are depicted in FIG. 9B and the experimental results are shown in FIG. 9A.

The dose response curves of various RNAi molecules depicted in FIG. 8A show that RNAi molecules are functional when the sense strand, i.e. the second stand, is modified on both ends with amino groups. Particularly effective are RNAi molecules 20A26B, 18A26B, and 28A26B. The lowest activity is shown by RNAi molecule 26A26B which corresponds to end modification on all 4 ends of the duplex (the molecules described by Tuschl are 18AB).

However, RNAi activity is also achieved when the antisense strand, i.e. the first strand, is modified only at the 3' end leaving a free OH group at the 5' end (RNAi constructs 22A26B; 20A26B). There is no activity when the antisense strand is modified with amino groups on both the 5' and the 3' end (26A26B). This leads to the conclusion that any end of the antisense strand and more particularly the 5' end of the antisense should be kept without modifications. Additionally, it is worth stating that the $NH_2$ end modification can be used to inactivate the sense strand on the 5' and 3' end and therefore reduce off-target effects mediated by an otherwise functional sense strand which results in a significantly increased specificity of the RNAi molecule which is advantageous for target validation as well as for any medical use of the RNAi molecule.

The further generalisation of the results from this experiment is depicted in FIG. 9C. Functionally active RNAi are accordingly those not having an amino modification at the antisense strand or having an amino modification only at the 3' end of the antisense strand whereas an amino modification at both ends of the antisense strand is not functional, i.e. does not result in a knockdown of the target mRNA.

Figure 10A:
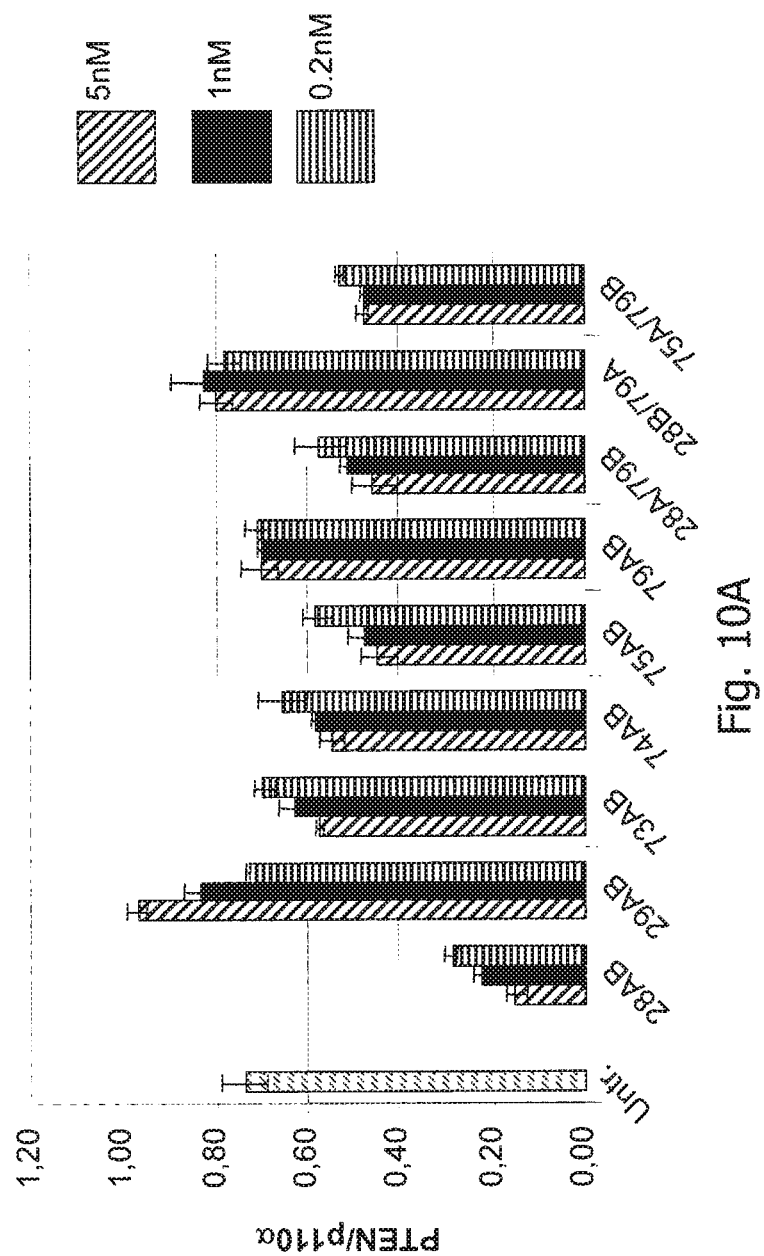

Example 7. Impact of 2'-O-methyl Modification of RNAi Molecules for Endonuclease Protection RNA knockdown was again shown using real time RT-PCR analysis on HeLa cells transfected with RNAi duplex molecules directed against the PTEN mRNA as represented in FIG. 10A. Experimental procedures were basically the same as specified in Example 1. The structure of the RNAi molecules investigated and their dose responses, which are depicted in FIG. 10A, are shown in FIG. 10C. The nucleotides printed in bold are those having a 2'-O-methyl modification.

It is illustrated by the dose response curves shown for various RNAi molecules in FIG. 10A that internal 2'-O-alkyl groups reduce RNAi activity. Preferably such 2'-O-alkyl groups are 2'-O-methyl or 2'-O-ethyl groups. However, molecules with unmodified nucleotides in combination with 2'-O-alkyl modification show significant activity. As is also depicted in FIG. 10A no activity was obtained when the antisense strand is all modified with 2'-O-methyl groups and the sense strand is not modified (c.f., e.g., RNAi molecule 79A28B). Taken the results of a stability test such as incubation of the various RNAi molecules in serum, as depicted in FIG. 10B, shows that 2'-O-alkyl modifications stabilize RNAi molecules against degradation. This clearly beneficial effect, however, is at least to a certain degree counterbalanced by the effect that 2'-O-alkyl modifications generally result in a reduced knockdown activity. Accordingly, the design of RNAi molecules has to balance stability against activity which makes it important to be aware of the various design principles as disclosed in the present application.

Example 8: Impact of Blocks of Internal 2'-O-methyl Modifications on the Stability of RNAi Molecules in Serum The experimental approach in connection with this study was the same as depicted in Example 1. Again, PTEN RNA was analysed by real time RT-PCR on HeLa cells at a density of 2000 cells/well which were transfected with different doses of RNAi molecules. RNAi molecules were incubated in serum for two hours and analysed on a 10% polyacrylamide gel. The results of this study are illustrated in FIGS. 11A to 11C, whereby FIG. 11A shows the dose response of the various RNAi molecules depicted in FIG. 11C, and FIG. 11B shows the result of a stability test using some of the RNAi molecules depicted in FIG. 11C. The nucleotides written in bold in FIG. 11C are the ones carrying a modification, in this case a 2'-O-methyl modification of the ribose moiety of the nucleotides.

A dose dependent inhibition by the unmodified RNAi molecules was observed. It was also shown that the 2'-O-methyl modification of the core 9 nucleotides made the RNAi stable in serum and allowed activity of the duplex in mediating the interference phenomenon leading to a degradation of the PTEN mRNA. Total modification of the sense strand makes the RNAi molecule stable in serum and allows certain activity.

Alternating blocks of 5 nucleotides with 2'-O-methyl modification renders the RNAi molecule stable in serum and allows activity on PTEN RNA as shown by incubating the RNAi duplex in serum for two hours and loading the samples on a 10% polyacrylamide gel. As may be taken from FIG. 11B the duplex comprising strands 80A and 80B was strongly degraded after incubation in serum for two hours. The duplex consisting of strands 82A and 82B confirmed the result that the 5'-end of the first strand which comprises the antisense strand should not be modified at the 5'-terminal nucleotides (compare 82A82B with the reverse orientated 81A81B). This was also confirmed by the results obtained having the duplex consisting of the strands 86A and 86B which is both active and stabilised in serum. It is noteworthy that molecules with unmodified blocks at the terminal 5' of the antisense strand are more active whereby the 5'terminal OH group is preferably not derivatized.

Further experiments were carried out using different modification patterns of 2'-O-methyl modification of the nucleotides. The results thereof are shown in FIG. 12A to 12C and further discussed herein in example 9.

Example 9: The Impact of Alternating Internal 2'-O-Alkyl Modification on Serum Stability of RNAi Molecules The experimental set-up for performing this kind of study was the same as used in connection with the studies reported in Example 1 and Example 8, respectively, with the targeted nucleic acid being again PTEN mRNA, HeLa cells were transfected with the different RNAi molecules depicted in FIG. 12B and RNA knockdown was demonstrated using real time RT-PCR on PTEN RNA in a dose-dependent manner (FIG. 12A). The stability of the various RNAi molecules after 15 min and two hours in serum at 37° C. is depicted in FIG. 12C and a Western Blot for p110 and PTEN as the target-protein of the various RNAi molecules is depicted in FIG. 12D with the RNAi molecules tested being the same in both the experiments underlying FIG. 12C and FIG. 12D.

Figure 12A:
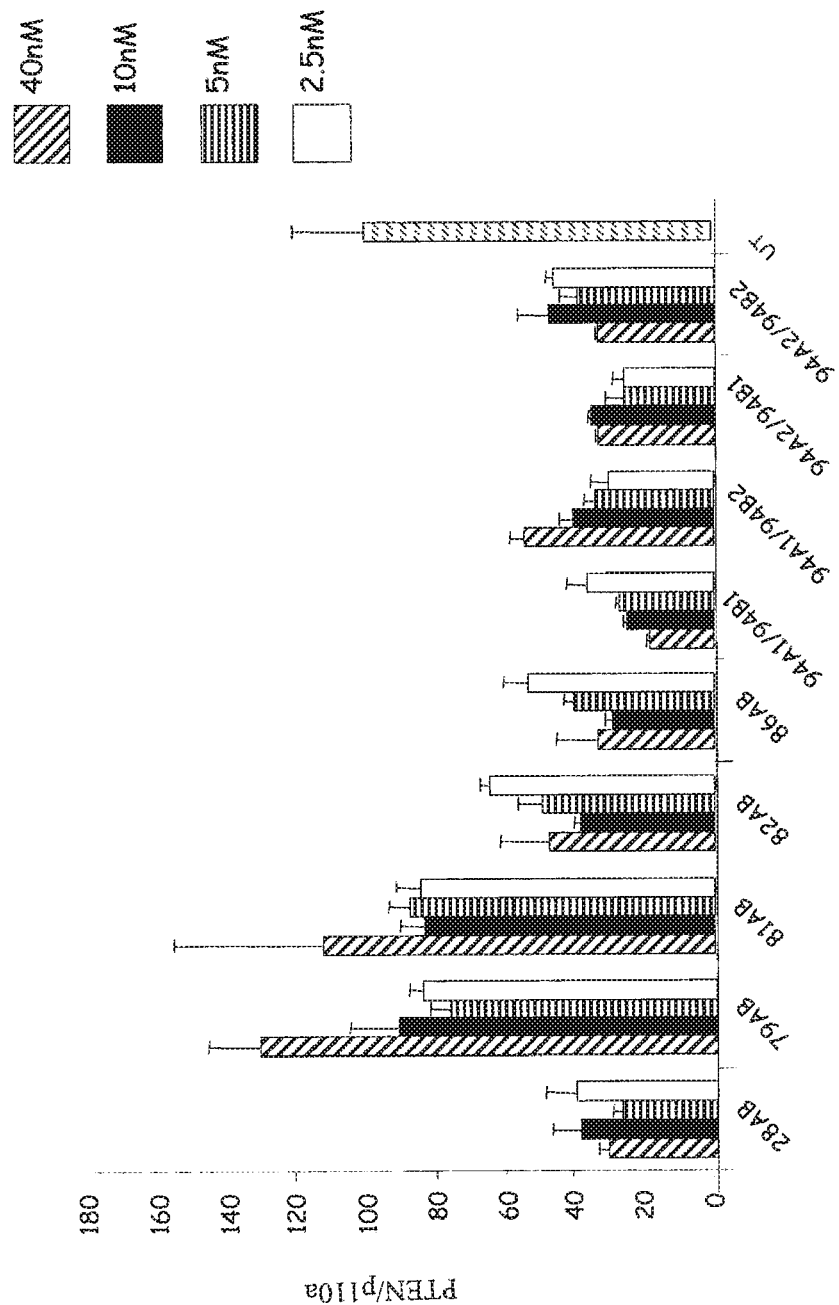
Figure 12C:
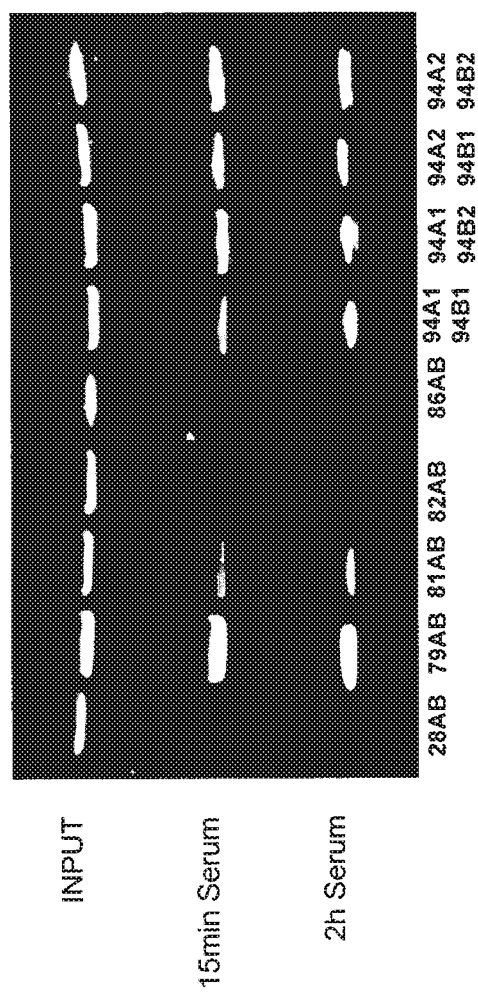

As illustrated in FIG. 12A and FIG. 12C nucleotides modified with 2'-O-methyl groups alternating with unmodified nucleotides rendered RNAi molecules stable in serum while still allowing them to be active in the sense of interfering with the target mRNA. It was shown that incubation of RNAi duplex molecules for 15 min and two hours in serum degraded the unmodified duplex and the duplex where the 10 most 5'-positioned nucleotides were unmodified.

In the RNAi molecules represented in FIG. 12B various patterns of modified and unmodified nucleotides were prepared. The RNAi molecule 94A1/94B1 comprises a structure wherein a modified nucleotide is flanked by an unmodified nucleotide with the unmodified nucleotide being located at the 5' end of the first strand. The RNAi molecule comprised of strands 94A2 and 94B2 was another example where the modified nucleotides and the unmodified nucleotides of the first and the second strand were located at opposing sites. In contrast to this the RNAi molecule comprised of strands 94A1 and 94B2 had the same pattern of modified and unmodified nucleotides. However, there was a phase shift such that the modified nucleotide base paired with an unmodified nucleotide. The two RNAi molecules comprised of strands 94A1 and 94B1 and strands 94A2 and 94B2 differed from each other such that in the first case the first strand starts with an unmodified nucleotide and the corresponding first nucleotide of the second strand, i.e. the nucleotide at the 3' end of the second strand, starts with an unmodified nucleotide with the arrangement being opposite to this in the RNAi molecule comprised of 94A2 and 94B2.

Figure 12D:
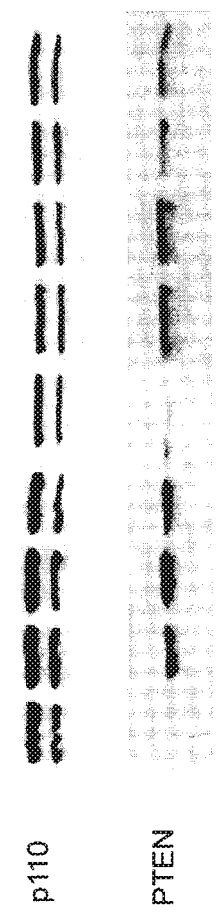
FIG. 12D shows an immunoblot for PTEN protein upon application of different RNAi molecules to HeLa cells. As may be taken therefrom RNAi molecules with alternating modifications are stabilized against endonuclease degradation and active in mediating a PTEN protein knock down.

Additionally, alternatingly modified RNAi molecules as depicted in FIG. 12B were functional in mediating a PTEN protein knock down as shown in FIG. 12D but only when the second 5' and second 3' terminal nucleotide was not modified (see 94A294B1 and 94A294B2). Taken together these data show that the most stable and most active RNAi molecules have alternating 2' alkyl modified and unmodified nucleotide residues. It should be noted that these molecules do show a very similar mRNA reduction when compared to unmodified siRNA molecules while being stable in serum and therefore allowing increased or easier handling.

Example 10: Functional Protein Knockdown Mediated by Internally Modified RNAi Molecules The experimental approach was similar to the one outlined in connection with example 1.

Western Blots were performed on HeLa cells harvested at various time points following transfection (48, 72, 96 and 120 hours) with alternatingly modified RNAi molecules as depicted in FIG. 12B. For experimental reasons it is noteworthy that at the 96 hour time point cells were split and half the population was replated. A total of 40 nM of the various RNAi molecules were applied to the cells. Cells were continuously transfected for 72 h with cationic lipids as described in example 1; then replated in the absence of transfection reagents.

Transfections were carried out in 96 well or 10-cm plates (at 30% to 50% confluency) by using various cationic lipids such as Oligofectamine, Lipofectamine (Life Technologies), NC388, L8 (Atugen, Berlin), RNAi were transfected by adding pre-formed 5× concentrated complex of siRNAs and lipid in serum-free medium to cells in complete medium. The total transfection volume was 100 µl for cells plated in 96-wells and 10 ml for cells in 10 cm plates. The final lipid concentration was 0.8 to 1.2 µg/ml depending on cell density; the siRNA concentration is indicated in each experiment.

Figure 13:
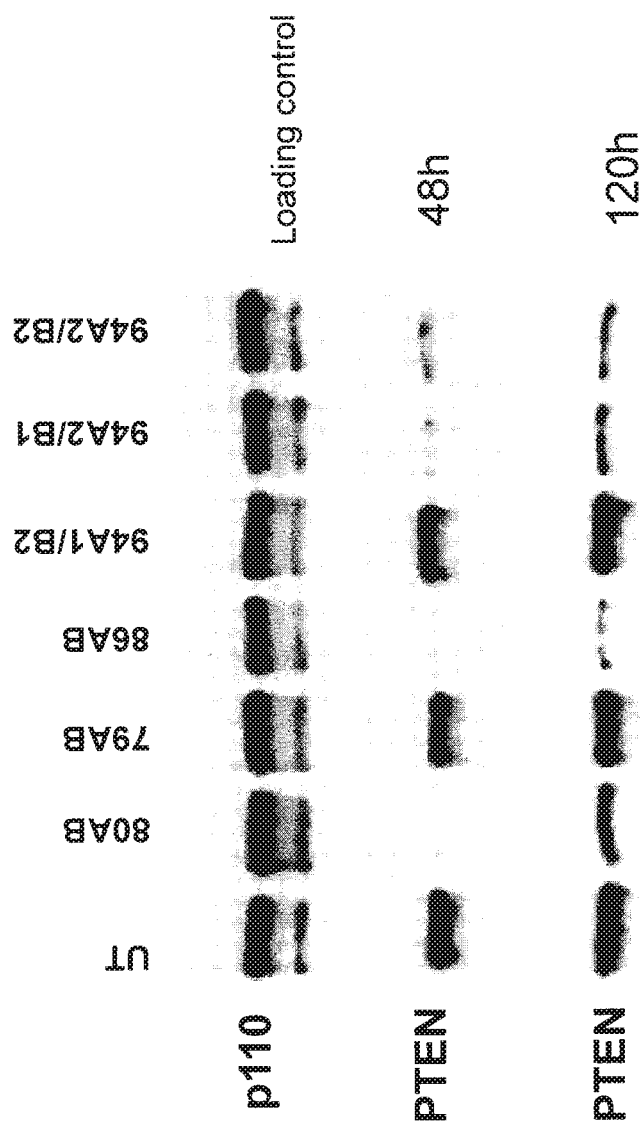
FIG. 13 shows the result of a Western Blot analysis to determine the time course of PTEN protein knock down. Cells were continuously transfected with 2'-O-methyl modified versus unmodified RNAi molecules using cationic lipids for 72 h. Protein lysates were prepared and analysed by immunoblot after 48 and 120 h. For the 96 h and 120 h timepoints the cells were split, replated and incubated in the absence of RNAi molecules for an additional 24 and 48 h.

The result of the Western Blot analysis is depicted in FIG. 13. As can be taken from this Figure, modified RNAi molecules of the 94A2B1 and 94A2B2 version yielded a longer lasting PTEN protein knock down as unmodified molecules. The lack of protein knock down also seen in FIG. 12 with molecules of the 94A1B1 and 94A1B2 version was confirmed in this experiment. Unmodified molecules (80AB) were not as potent in supporting long lasting protein knock down when the cells were not continuously transfected.

Figure 14:
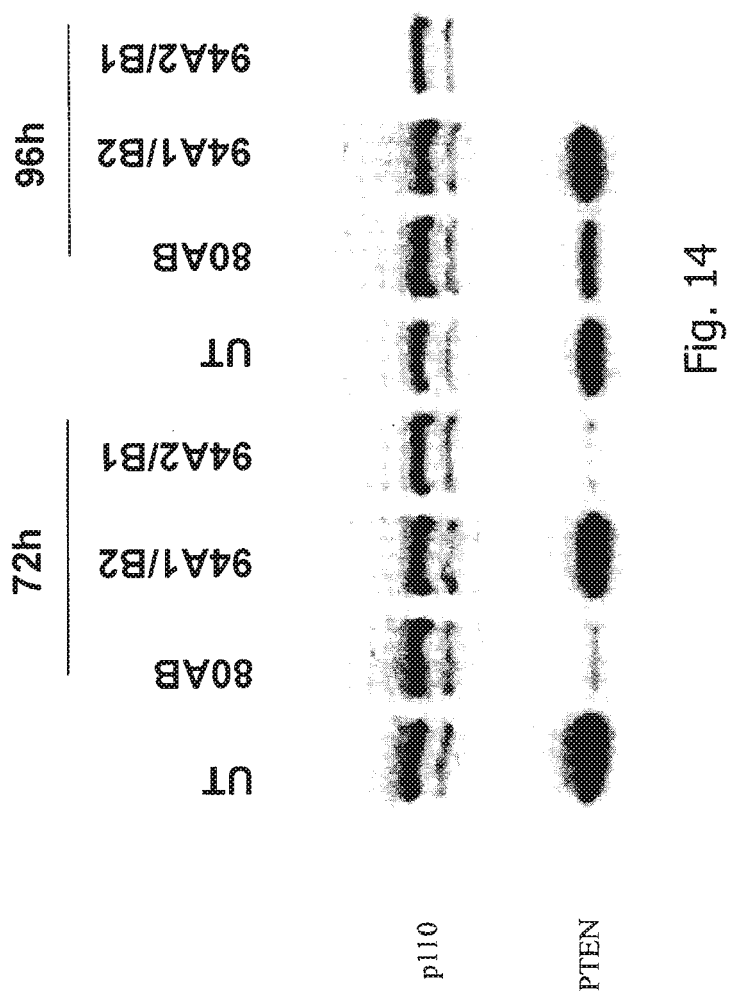
FIG. 14 shows a Western Blot depicting the protein knock down of PTEN being persistent using alternating modified RNAi molecules versus unmodified RNAi molecules. Transfections were performed for only 5 h and new medium without transfection reagents was added. Lysates were analysed by immunoblot 72 h and 96 h post transfection with the indicated RNAi molecules.

Example 11: Persistent PTEN Protein Knock Down with Alternating 2'-O-methyl Modifications of RNAi Molecules The experimental approach was similar to the one outlined in connection with example 10 with the exception that the transfection was terminated after 5 h by replacing the transfection medium with new medium. The protocol was slightly modified such that for each of the RNAi molecules a 40 nM concentration was realized using a stock solution of 1 g RNAi/ml cationic lipid as described in connection with example 1.5 hours after transfection the medium was withdrawn and fresh EMEM added. The cells were split after 72 h, with half of the cells being lysed and the other half newly plated and lysed 24 h later (96 h post transfection). The result of a Western Blot analysis using 3 different RNAi molecules (80AB, 94A1/B2, 94A2/B1 are depicted in FIG. 14. As a positive control untreated cells were used. FIG. 14 shows the expression of PTEN after 72 h and 96 h, respectively. Taken the structural particularities of the various RNAi molecules it can be taken from FIG. 14 that protein knockdown is persistent with alternating molecules of the 94A2B1 kind even over 96 h after splitting and replating cells compared to unmodified RNAi molecules (such as 80AB) and RNAi molecule 94A1B2.

A further experiment was carried out using the siRNA constructs as depicted in FIG. 15A (left panel). From the results as depicted as ratio of PTEN/p110α mRNA degradation at the various concentrations of siRNA constructs administered to the test system, it can be taken that siRNA molecules with either one or both strands consisting of 2'-O-methyl residues were not able to induce RNA interference in the mammalian system (FIG. 15A, molecules V2, V5, V6). However, the decrease in activity was less pronounced when only parts of the strands were modified. Interestingly, a molecule having an unmodified antisense strand (which is the upper strand in the representation throughout this specification if not indicated otherwise) and a completely modified sense strand was significantly more active when compared to the reversed version (FIG. 5A, molecules V5 and V6). This result suggests that the antisense strand of the siRNA seems to be more critical and sensitive to modification. The most efficient molecules inducing PTEN mRNA had only stretches of modifications leaving the 5' end unmodified or were modified on alternating positions on both strands (FIG. 15A, molecules V10, V12).

To test the nuclease resistance the different siRNA versions were incubated in serum followed by PAA gel electrophoresis. The result is shown in FIG. 15B (right panel with the various sequences indicated on the left panel of FIG. 15B) As shown earlier, blunt ended siRNA molecules with unmodified ribonucleotides were very rapidly degraded whereas a complete substitution with 2'-O-methyl nucleotides mediated resistance against serum-derived nucleases (FIG. 15B, compare molecule AB with V1). siRNA molecules with partial 2'-O-methyl modification also showed an increased stability when compared to unmodified siRNAs. In particular, molecules with alternating modifications on both strands showed a significant improvement in instability (FIG. 15B, molecules V13, V14, V15 and V12). More importantly, transfection of three of these molecules into HeLa cells resulted in a significant down regulation of PTEN protein expression as depicted in FIG. 15C, length 6, 9 and 10). In this RNA interference activity assay an unexpected preference for molecules was observed which were modified at every second nucleotide beginning with the most 5' terminal nucleotide of the antisense strand (molecules V15 and V12). Molecules which contained modifications beginning with the second nucleotide at the 5' end of the antisense strand were more stable but had a strongly reduced activity in gene silencing (molecules V13, V14). This result points towards highly specific interactions between the involved enzymes and precise nucleotides in the siRNA duplex. Taken together the data shown herein demonstrate that 2'-O-methyl modifications at particularly selected positions in the siRNA duplex can increase nuclease resistance and do not necessarily abolish RNAi completely.

Although an increased stability of synthetic siRNA has primarily implication for in vivo application, it was also analysed whether the particular modification can also lead to an extended protein knock-down in cell culture systems. Accordingly, HeLa cells were transiently transfected for six hours using different versions of PTEN specific siRNAs. The lipid siRNA complex was then washed away and the PTEN protein knock-down was analysed 48 hours and 120 hours later. Although knock-down experiments without continued transfection of siRNAs were complicated due to rapid growth of untransfected cells in this time period resulting in a very transient knock-down, the present inventors were able to demonstrate a prolonged PTEN protein knock-down with siRNA molecules stabilised by the described 2'-O-methyl modification. At 48 hours post transfection the unmodified siRNA (AB) showed the biggest reduction in PTEN protein levels, however, at 120 hours post transfection the reduction in PTEN protein expression was superior with the siRNA stabilised by alternating 2'-O-methyl modifications (FIG. 15D, compare lane 2 with lanes 4, 6 and 7).

From the results it can also be surmised that the starting nucleotide position of the alternating modification can affect the activity of the duplex. To test this preference in more detail two additional series of siRNAs were synthesized, one specific for the kinase Akt1 and the other one specific for p110β which is one of the two catalytic subunits of PI(3-) kinase. The particular constructs are shown in FIG. 16A. Only 19 nt long siRNA duplexes either without any or with 2'-O-methyl modification on every second other nucleotide were used. Using Akt1 as a target an efficient protein knock-down as well as a dramatic reduction in phospho-Akt levels were observed with blunt, unmodified siRNAs (FIG. 16A, right panel). From the different versions of molecules with modifications on every second other nucleotide only one was efficiently mediating RNAi (FIG. 16A, molecule V5). This siRNA molecule contained an antisense strand which was modified at the most terminal 5' and 3' nucleotides. The sense strand started with the unmodified nucleotides at the most terminal position, resulting in a structure in which the modified and unmodified ribonucleotides of both strands face each other. As expected, this molecule was also protected against serum-derived nucleases as depicted in FIG. 16B (molecule V5).

Figure 16C:
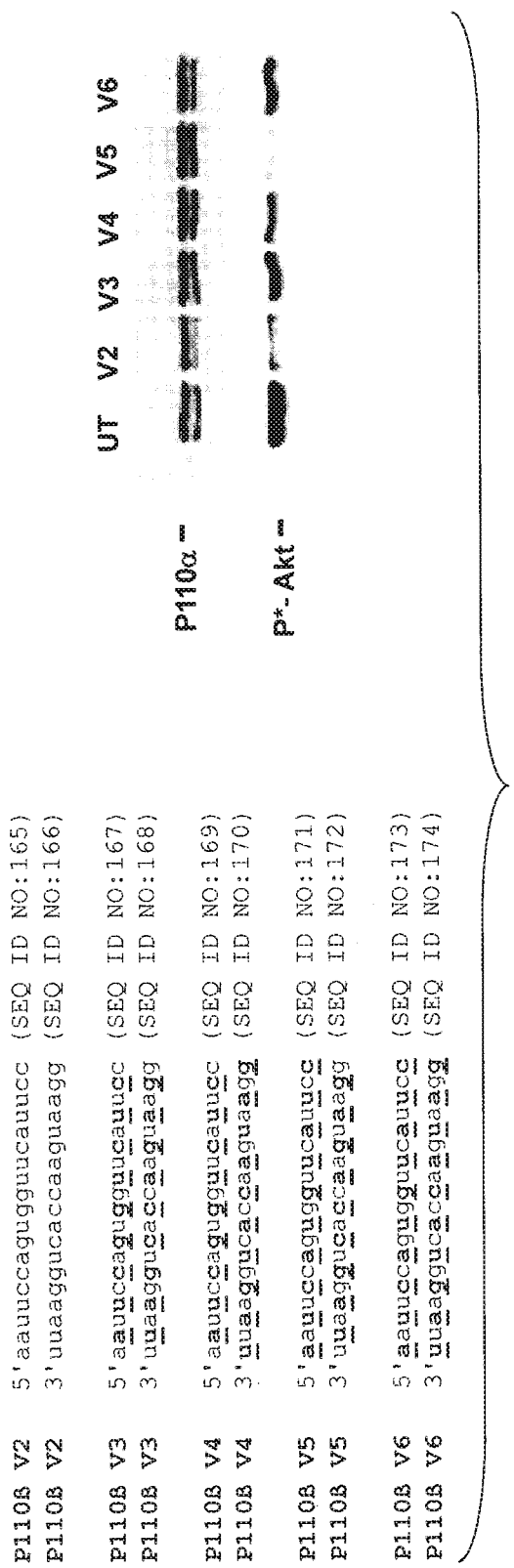

Interestingly, a very similar 19 nt long siRNA molecule (V4) with modifications beginning at the second nucleotide of the antisense strand showed no RNA interference activation in the particular assay used. The version V6 in which the modified nucleotides of the antisense strand face modified nucleotides on the sense strand, was also inactive in this experiment. An identical series of 19 nt long siRNA molecules specific for p110β confirmed these observations as depicted in FIG. 16C. Again the similarly modified siRNA molecule (V5) was the most active, as indicated by reducing Akt phosphorylation, which is indicative for a reduced P (I)-3 kinase activity due to reduced p110β levels. The reduced activity of the molecules V6 might be explained by reduced duplex stability since the same structure was active in the PTEN knock-down experiment with 21mer siRNAs. Although it is known that 2'-O-methyl modification on both strands facing each other reduces the stability of nucleic acid duplexes, the difference between the activity of siRNA molecules V4 and V5 (FIGS. 16B and C) probably is not due to differences in duplex stability since the number of base pairing of modified and unmodified nucleotides is identical. This difference in activity might be due to specific requirements in the interacting proteins involved in the degradation of the target mRNA. Also it can be taken from these experiments that the most terminal nucleotides of the antisense strand can be modified at the 2'-OH-group with significant loss of silencing activity.

Example 12: Different Loop Structures are Functional in Mediating RNA Interference To test whether RNAi molecules, preferably synthetic RNAi molecules with self complementary structures, can inhibit gene expression as efficiently as standard double stranded siRNA molecules, HeLa cells were transfected with p110β specific synthetic siRNAs. Transfections were carried out in 96 well or 10-cm plates (at 30% to 50% confluency) by using various cationic lipids such as Oligofectamine, Lipofectamine (Life Technologies), GeneBlocs were transfected by adding pre-formed Si concentrated complex of GB and lipid in serum-free medium to cells in complete medium. The total transfection volume was 100 µl for cells plated in 96-wells and 10 ml for cells in 10 cm plates. The final lipid concentration was 0.8 to 1.2 µg/ml depending on cell density; the RNAi molecule concentration is indicated in each experiment.

A dose dependent titration showed no significant difference in efficiency of mRNA knock-down achieved by the standard bimolecular double strand 21mer and the corresponding monomolecular molecules as analysed by realtime PCR (Taqman) (FIG. 17A) Two different loop structures a $(A)_{12}$ loop (SEQ ID NO: 175) and a HIV derived pA-loop were tested in parallel with similar results. A comparison of the relative position of the antisense sequence and the loop structure revealed an improved knock-down efficiency with the antisense sequence being located 3' to the loop (FIG. 17B; compare construct 3A, 3B and 4A, 4B).

Example 13: Studies on the Efficacy of Different Intramolecular Hairpin Loops and Intermolecular "Bubbles"

The influence of different loop structures on inhibition of mRNA and protein expression was tested. For these experiments Akt1 and Akt2 were chosen as targets. The experimental approach was similar to the one described in example 12.

Figure 18C:
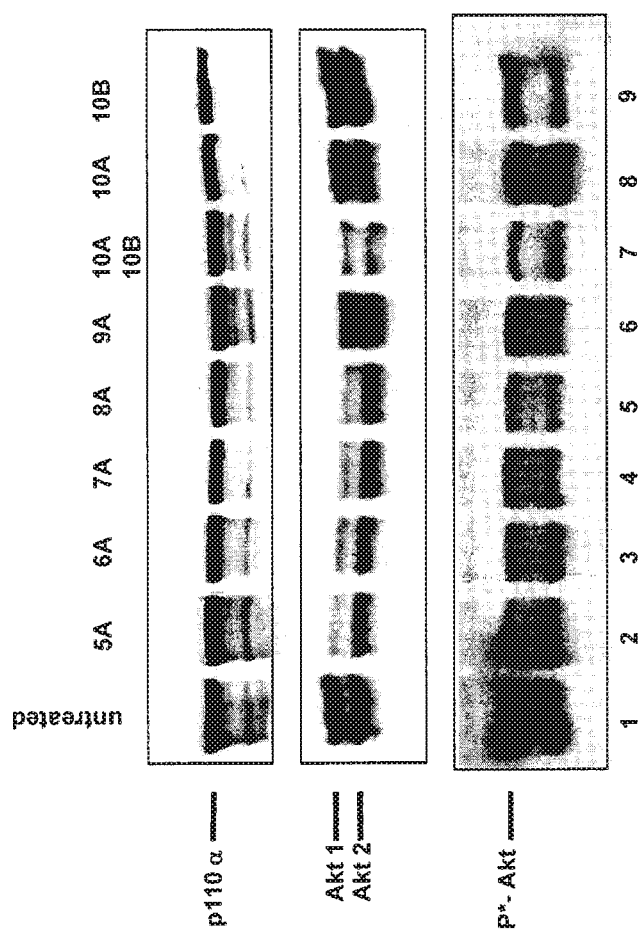

Significantly, the reduction in Akt1 mRNA as depicted in FIG. 18A and FIG. 18B as well as Akt1 protein levels as depicted in FIG. 18C was completely independent of the loop structure tested (compare molecules 5A, 6A, 7A, 8A) (the structure of the RNAi molecule tested is always depicted underneath the bar diagram). Even a molecule containing a rather unphysiological structure such as a polyethyleneglycol linker (PEG) as a loop efficiently reduced Akt1 expression indicating that size and nucleotide sequence of the loop is not crucial (FIG. 18A; molecule 8A). A synthetic siRNA molecule specific for Akt2 (9A) was used to control for specificity, and had no effect on Akt1 levels as shown in FIG. 15A. This molecule, however, efficiently silenced Akt2 expression (FIG. 18B; FIG. 18C). Self-complementary RNA molecules with loop structures have the possibility to anneal as double strands in monomolecular or bimolecular structures under physiological hybridization conditions (FIG. 18B, loop or bubble structure). To address the question of whether the siRNA molecules exert their function via adapting an intra-molecular loop or an inter-molecular "bubble" (schematically shown in FIG. 18B) two molecules not capable of folding back on themselves were transfected. These constructs contained Akt1- and Akt2-specific sequences within the same molecule (FIG. 18B, constructs 10A, 10B) and were designed so as to prevent formation of an intramolecular duplex (i.e. a bimolecular duplex or "bubble" was formed). Surprisingly, this molecule efficiently mediated both Akt and Akt2 mRNA knock-down as well as protein knock-down when transfected after annealing of both strands.

Whether loop and bubble structures are indeed substrates for RNA processing enzymes, e.g. Dicer, is not clear at this point. A recent study by Paddison and coworkers suggests that hairpin containing siRNAs are more dependent on Dicer activity than double stranded siRNAs. However, these data demonstrating RNA interference activity using a PEG linker molecule indicate that the linker sequence is likely to be irrelevant.

The features of the present invention disclosed in the specification, the claims and/or the drawings may both separately and in any combination thereof be material for realizing the invention in various forms thereof.

The invention claimed is:

1. A double stranded siRNA molecule against a target nucleic acid, wherein the double stranded siRNA molecule comprises a first strand and a second strand, wherein the first strand comprises a first stretch that is complementary to the target nucleic acid, wherein the second strand comprises a second stretch that has the same length as the first stretch and is complementary to the first stretch, wherein the first strand and the second strand form a double-stranded structure comprising the first stretch and the second stretch,
   wherein the first stretch and the second stretch each has the length of 17-21 nucleotides, wherein the first stretch and the second stretch each comprises a plurality of groups of 2'-O-methyl ribonucleotides flanked on one or both sides by a flanking group of unmodified ribonucleotides or modified ribonucleotides different from 2'-O-methyl ribonucleotides, and
   wherein at least one of the two strands has an overhang of at least one nucleotide at the 3'-end.

2. The double stranded siRNA molecule of claim 1, wherein the number of 2'-O'methyl ribonucleotides in each of the plurality of groups of 2'-O-methyl ribonucleotides is one to ten.

3. The double stranded siRNA molecule of claim 1, wherein the number of unmodified ribonucleotides or modified ribonucleotides different from 2'-O-methyl ribonucleotides in each of the flanking groups is one to ten.

4. The double stranded siRNA molecule of claim 1, wherein the first stretch and the second stretch each has the length of 18-19 nucleotides.

5. The double stranded siRNA molecule of claim 1, wherein the plurality of groups of 2'-O-methyl ribonucleotides are flanked on one or both sides by a flanking group of modified ribonucleotides different from 2'-O-methyl ribonucleotides.

6. The double stranded siRNA molecule of claim 5, wherein the modified ribonucleotides different from 2'-O-methyl ribonucleotides are 2'-fluoro ribonucleotides.

7. The double stranded siRNA molecule of claim 6, wherein each 2'-fluoro ribonucleotide on the first stretch corresponds to a 2'-O-methyl ribonucleotide on the second stretch.

8. The double stranded siRNA molecule of claim 6, wherein each 2'-fluoro ribonucleotide on the second stretch corresponds to a 2'-O-methyl ribonucleotide on the first stretch.

9. The double stranded siRNA molecule of claim 1, wherein the plurality of groups of 2'-O-methyl ribonucleotides are flanked on one or both sides by a flanking group of unmodified ribonucleotides.

10. The double stranded siRNA molecule of claim 9, wherein each 2'-O-methyl ribonucleotide on the first stretch corresponds to an unmodified ribonucleotide on the second stretch.

11. The double stranded siRNA molecule of claim 9, wherein each 2'-O-methyl ribonucleotide on the second stretch corresponds to an unmodified ribonucleotide on the first stretch.

12. The double stranded siRNA molecule of claim 9, wherein the first stretch comprises single 2'-O-methyl ribonucleotides flanked on one or both sides by unmodified ribonucleotides.

13. The double stranded siRNA molecule of claim 9, wherein the second stretch comprises groups of one to ten 2'-O-methyl ribonucleotides flanked on one or both sides by unmodified ribonucleotides.

14. The double stranded siRNA molecule of claim 1, wherein the 3'-end of the first strand has an overhang.

15. The double stranded siRNA molecule of claim 14, wherein the overhang has one to eight nucleotides.

16. The double stranded siRNA molecule of claim 1, wherein the 3'-end of the second strand has an overhang.

17. The double stranded siRNA molecule of claim 16, wherein the overhang has one to eight nucleotides.

18. The double stranded siRNA molecule of claim 1, wherein one end of the double stranded siRNA molecule is blunt ended.

19. The double stranded siRNA molecule of claim 1, wherein the blunt end is at the 5'-end of the first strand and 3'-end of the second strand.

20. The double stranded siRNA molecule of claim 1, wherein the first stretch and the second stretch each has the length of 21 nucleotides.

21. The double stranded siRNA molecule of claim 1, wherein the target nucleic acid is selected from the group comprising structural genes, housekeeping genes, transcription factors, motility factors, cell cycle factors, cell cycle inhibitors, enzymes, growth factors, cytokines, and tumor suppressors.

22. A composition comprising the double stranded siRNA molecule of claim 1.

23. The composition of claim 11, wherein the composition is a pharmaceutical composition.

* * * * *